US012622915B2

(12) United States Patent
Koprivica

(10) Patent No.: US 12,622,915 B2
(45) Date of Patent: May 12, 2026

(54) METHODS OF TREATING PDE IV-MEDIATED DISEASES OR CONDITIONS

(71) Applicant: Vanda Pharmaceuticals Inc., Washington, DC (US)

(72) Inventor: Vuk Koprivica, Bethesda, MD (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 448 days.

(21) Appl. No.: 18/044,805

(22) PCT Filed: Sep. 10, 2021

(86) PCT No.: PCT/US2021/049870

§ 371 (c)(1),
(2) Date: Mar. 10, 2023

(87) PCT Pub. No.: WO2022/056265

PCT Pub. Date: Mar. 17, 2022

(65) Prior Publication Data

US 2023/0364100 A1 Nov. 16, 2023

Related U.S. Application Data

(60) Provisional application No. 63/076,774, filed on Sep. 10, 2020.

(51) Int. Cl.
*A61K 31/53* (2006.01)

(52) U.S. Cl.
CPC .................................... *A61K 31/53* (2013.01)

(58) Field of Classification Search
CPC ....... A61K 31/53; A61K 9/0048; A61P 17/00; A61P 27/02
See application file for complete search history.

(56) References Cited

U.S. PATENT DOCUMENTS

| | | | |
|---|---|---|---|
| 7,153,854 | B2 | 12/2006 | Abe et al. |
| 10,604,492 | B2 | 3/2020 | Verkman et al. |
| 11,839,616 | B2 | 12/2023 | Verkman et al. |
| 2006/0089375 | A1 | 4/2006 | Allen et al. |
| 2008/0027112 | A1 | 1/2008 | Govek et al. |

FOREIGN PATENT DOCUMENTS

| | | | |
|---|---|---|---|
| CN | 101495454 | A | 7/2009 |
| JP | 2019-505502 | A | 2/2019 |
| JP | 2020-531511 | A | 11/2020 |
| RU | 2328499 | C2 | 7/2008 |
| WO | 2004024728 | A2 | 3/2004 |
| WO | 2007142929 | A2 | 12/2007 |
| WO | 2017112951 | A1 | 6/2017 |
| WO | 2019040919 | A1 | 2/2019 |
| WO | 2021113580 | A1 | 6/2021 |

OTHER PUBLICATIONS

Harkevich, Farmakologija, [English: "Pharmacology"], 10th edition, Moscow, GJeOTAR-Media, pp. 73-74, 2010.

(Continued)

*Primary Examiner* — San Ming R Hui
(74) *Attorney, Agent, or Firm* — BakerHostetler

(57) ABSTRACT

The disclosure provides methods and compositions for the treatment of PDE IV-mediated diseases or conditions, including inflammatory diseases or conditions, using a compound of Formula (I) or a pharmaceutically acceptable salt thereof:

23 Claims, 43 Drawing Sheets

(56) References Cited

OTHER PUBLICATIONS

Olisova et al., Ingibitor fosfodijesterazy-4 v lechenii, [English "Phosphodiesterase-4 inhibitor in treatment"], Vestnik Dermatologii i Venerologii, 95(2):74-80, 2019. (English Abstract Submitted).
Sadrai Z. et al., PDE4 inhibition suppresses IL-17-associated immunity in dry eye disease, Investigative ophthalmology & visual science, 53(7):3584-3591, 2012.
Zhulenko et al., Farmakologija, [English: "Pharmacology"], Moscow, KolosS, pp. 34-35, 2008.
Edelson et al., Poster: 303, Cilomilast (Ariflo®), A Potent, Selective Inhibitor Of Phosphodiesterase 4, Improves Lung Function In COPD Patients: Results of a 6-Month Trial, ATS 98th International Conference, May 17-23, 2002, Atlanta, GA.
Abelson, Md, Mark B., et al., "Conjunctival Allergen Challenge", Arch Ophthalmol, Jan. 1990, vol. 108, pp. 84-88.
Abelson, Md, Mark B., et al., "Conjunctival Allergen Challenge: Models in the Investigation of Ocular Allergy", Current Allergy and Asthma Reports, (2003), vol. 3, pp. 363-368.
Banner, Katharine H., et al., "PDE4 Inhibition: a Novel Approach for the Treatment of Inflammatory Bowel Disease", Trends in Pharmalogical Sciences, Aug. 2004, vol. 25, No. 8, pp. 430-436.
Barnes, Peter J., "New Drugs for Asthma", Nature Reviews, Drug Discovery, Oct. 2004, vol. 3, pp. 831-844.
Bäumer, Wolfgang et al., "Effects of the Phosphodiesterase 4 Inhibitors SB 207499 and AWD 12-281 on the Inflammatory Reaction in a Model of Allergic Dermatitis", European Journal of Pharmacology, 2002, vol. 446, pp. 195-200.
Bender, Andrew T., et al., "Cyclic Nucleotide Phosphodiesterases: Molecular Regulation to Clinical Use", Pharmacological Reviews, 2006, vol. 58, No. 3, pp. 488-520.
Borker, Rohit D., et al., Effect of Cilomilast on Quality of Life Improvement/Deterioration and Non-Drug Costs in Patients with Chronic Obstructive Pulmonary Disease, Chest, 2003, vol. 124, No. 4, p. 170S.
Burnouf, Catherine et al., Recent Advances of PDE4 Inhibitors as Immunoregulators and Anti-Inflammatory Drugs, Current Pharmaceutical Design, 2002, vol. 8, 1255-1296.
Doherty, Annette M., "Phosphodiesterase 4 Inhibitors as Novel Anti-Inflammatory Agents", Current Opinion in Chemical Biology, 1999, vol. 3, pp. 466-473.
Dyke, Hazel, J., et al., "Update on the Therapeutic Potential of PDE4 Inhibitors," Expert Opinion Investigation on Drugs, 2002, 11, No. 1, pp. 1-13.
Gamanuma, Michiko et al., "Comparison of Enzymatic Characterization and Gene Organization of Cyclic Nucleotide Phosphodiesterase 8 Family in Humans", Cellular Signalling, 2003, vol. 15, pp. 565-574.
Giembycz, Mark A., "Phosphodiesterase 4 Inhibitors and the Treatment of Asthma", Drugs, Feb. 2000, vol. 59, No. 2, pp. 193-212.
Gillespie, Peter G., et al., "Inhibition and Stimulation of Photoreceptor Phosphodiesterases by Dipyridamole and M&B 22,948", Molecular Pharmacology, vol. 36, pp. 773-781.
Govek, Steven P., et al., "Water-soluble PDE4 Inhibitors for the Treatment of Dry Eye," Bioorganic & Medicinal Chemistry Letters, 2010, vol. 20, No. 9, pp. 2928-2932.
Griffiths, C.E.M., et al., "Randomized comparison of the type 4 phosphodiesterase inhibitor cipamfylline cream, cream vehicle and hydrocortisone 17-butyrate cream for treatment of atopic dermatitis", Br. J. Dermatol., 2002, 147(2), 299-307.
Huang, Zheng et al., "The Next Generation of PDE4 Inhibitors", Current Opinion of Chemical Biology, 2001, vol. 5, pp. 432-438.
Krishna, Ganesh et al., "New Therapies for Chronic Obstructive Pulmonary Disease," Expert Opinion on Investigational Drugs, 2004, vol. 13, No. 3, pp. 255-267.
Kumar, Anil, et al., "Analgesic and Anti-Inflammatory Effects of Phosphodiesterase Inhibitors", Indian Journal of Experimental Biology, Jan. 2000, vol. 38, pp. 26-30.
Lee, Sujin et al., "Nanomolar-Potency Aminophenyl-1,3,5-triazine Activators of the Cystic Fibrosis Transmembrane Conductance Regulator (CFTR) Chloride Channel for Prosecretory Therapy of Dry Eye Diseases11;" J. Med. Chem., Jan. 31, 2017, vol. 60, No. 3, pp. 1210-1218.
Li, Heng et al., "Phosphodiesterase-4 Inhibitors for the Treatment of Inflammatory Diseases," Frontiers in Pharmacology, vol. 9, Article 1048, Oct. 17, 2018, pp. 1-21.
Lipworth, Brian J., "Phosphodiesterase-4 Inhibitors for Asthma and Chronic Obstructive Pulmonary Disease", New Drug Classes, Lancet, 2005, vol. 365, pp. 167-175.
O'Donnell, James M., et al. Antidepressant Effects of Inhibitors of CAMP Phosphodiesterase (PDE4), Trends in Pharmacological Sciences, Mar. 2004, vol. 25, No. 3, pp. 158-163.
O'Donnell, James M., "William Harvey Research Conference on PDE Inhibitors: Drugs with an Expanding Range of Therapeutic Uses," Expert Opinion Investigation in Drugs, 2000, vol. 9, No. 3, pp. 621-625.
Press, Neil J., et al., "2 PDE4 Inhibitors—A Review of the Current Field", Progress in Medicinal Chemistry, 2009, vol. 47, pp. 37-74.
Renau, Thomas E., "The Potential of Phosphodiesterase 4 Inhibitors for the Treatment of Depression: Opportunities and Challenges", Current Opinion in Investigational Drugs, 2004, vol. 5, No. 1, pp. 34-39.
Richter, Wito et al., "Identification of Inhibitor Binding Sites of the cAMP-Specific Phosphodiesterase 4", Cellular Signalling, 2001, vol. 13, pp. 287-297.
Roos, Thomas C., et al., "Recent Advances in Treatment Strategies for Atopic Dermatitis", Drugs, 2004, vol. 64, No. 23, pp. 2639-2666.
Rotella, D. P., "Phosphodiesterases", Comprehensive Medicinal Chemistry II, 2007, pp. 919-957.
Sasaki, Takashi et al., "Identification of Human PDE7B, a cAMP-Specific Phosphodiesterase", Biochemical and Biophysical Research Communications, 2000, vol. 271, No. 3, pp. 575-583.
Spina, Domenico, "Phosphodiesterase-4 Inhibitors in the Treatment of Inflammatory Lung Disease," Drugs, 2003, vol. 63, No. 23, pp. 2575-2594.
Wolda, Sharon L., "PDE4 Inhibitors and Chronic Obstructive Pulmonary Disease", Emerging Drugs, 2000, vol. 5, No. 3, pp. 309-319.
Zhang, Han-Ting et al., "Effects of Rolipram on Scopolamine-Induced Impairment of Working and Reference Memory in the Radial-Arm Maze Tests in Rats", Psychopharmacology, 2000, vol. 150, pp. 311-316.
"Kratkij kurs molekuljarnoj farmakologii" in Russian, [English: "A Short Course of Molecular Pharmacology"] edited by P.V. Sergeev, Moscow, 1975, p. 10. (English Translation provided).
"Klinicheskaja farmakokinetika" in Russian, [English: "Clinical Pharmacokinetics"], L.E. Kholodov et al., Moscow, "Medicine", 1985, pp. 83-98, 134-138, 160, 378-380. (Machine Translation provided).

Fig, 24

Fig. 26
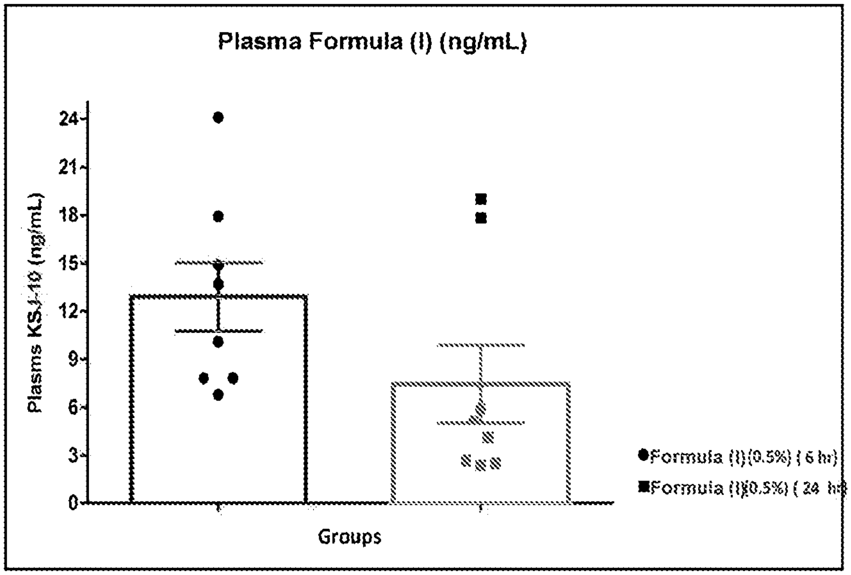
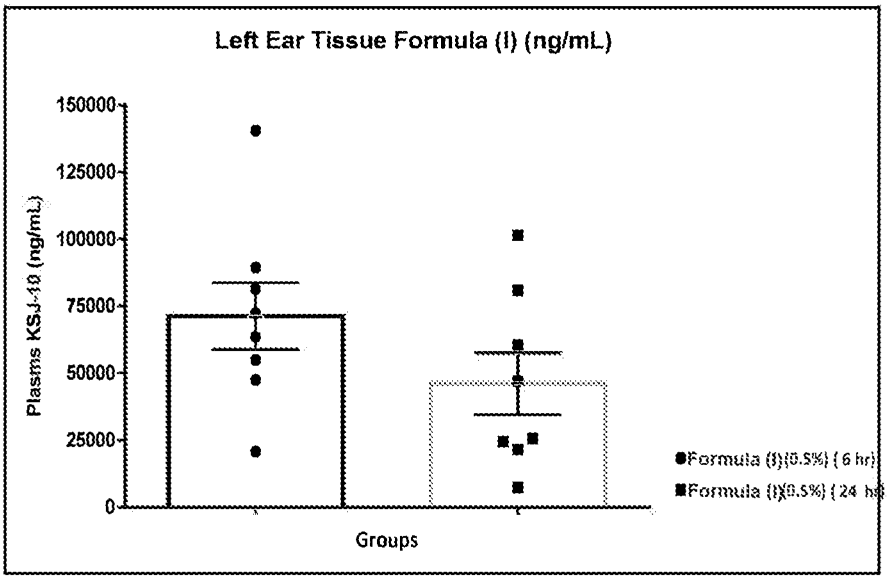

*p<0.05, **p<0.01 vs. Imiquimod control (Two way ANOVA followed by Dunnett's multiple comparisons test

*p<0.001, **p<0.0001 vs. IMQ control (Two- way ANOVA followed by Dunnett's multiple comparisons test)

p<0.05, p<0.01 *p<0.001, **p<0.0001 vs. Imiquimod control (Two way ANOVA followed by Dunnett's multiple comparisons test)*

*p<0.05, p<0.01, *p<0.001, ****p<0.0001 vs. IMQ control (One-way Anova followed by Dunnett's multiple comparisons test)

*p<0.05, p<0.01, *p<0.001, ****p<0.0001 vs. IMQ control (One-way Anova followed by Dunnett's multiple comparisons test)

*p<0.05, p<0.01, *p<0.001, ****p<0.0001 vs. IMQ control (One-way Anova followed by Dunnett's multiple comparisons test)

*p<0.05, p<0.01, *p<0.001, ****p<0.0001 vs. IMQ control (One-way Anova followed by Dunnett's multiple comparisons test)

*p<0.05, p<0.01, *p<0.001, ****p<0.0001 vs. IMQ control (One-way Anova followed by Dunnett's multiple comparisons test)

METHODS OF TREATING PDE IV-MEDIATED DISEASES OR CONDITIONS

CROSS-REFERENCE TO RELATED APPLICATION

This application is the U.S. National Phase Application under 35 U.S.C. § 371 of International Application No. PCT/US2021/049870, filed on Sep. 10, 2021, which claims the benefit of U.S. Provisional Application No. 63/076,774, filed on Sep. 10, 2020, the entireties of which incorporated by reference herein.

TECHNICAL FIELD

The disclosure is directed to methods and compositions for the treatment of PDE IV-mediated diseases or conditions.

BACKGROUND

Phosphodiesterase IV (PDEIV) is a family of cAMP-specific phosphodiesterase enzymes comprised of four distinct gene products, A-D. See D P Rotella, Phosphodiesterases, Comprehensive Medicinal Chemistry II, 2007, 919-957. PDE4 enzymes are expressed in the CNS and other nervous system tissues, smooth muscle, inflammatory and endothelial cells, and in the heart.

PDEIV is responsible for cAMP catabolism and regulation of inflammation in many types of cells. Some small molecule inhibitors of PDEIV have demonstrated anti-inflammatory properties. See. e.g., Sekut, L., et al., (1995), *Anti-inflammatory activity of phosphodiesterase (PDE)-IV inhibitors in acute and chronic models of inflammation.* Clinical & Experimental Immunology, 100:126-132. Inflammatory diseases or disorders, and other diseases and disorders having an inflammatory component, represent a significant portion of the conditions afflicting modern populations.

Given the large number of conditions in which inflammation is an undesireable aspect, there exists a need for methods of treating patients suffering from inflammation related disorders.

SUMMARY

The disclosure is directed to, among other things, methods for treatment of a patient with a phosphodiesterase IV (PDEIV)-mediated disease or condition comprising administering to said patient an amount of a compound of Formula (I):

(I)

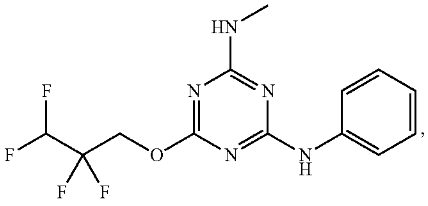, or a pharmaceutically acceptable salt thereof, effective to treat the disease or condition.

In other aspects, the disclosure is directed to methods of inhibiting release of an inflammatory cytokine from mammalian inflammatory cell by contacting the mammalian inflammatory cells with an amount of a compound of Formula (I):

(I)

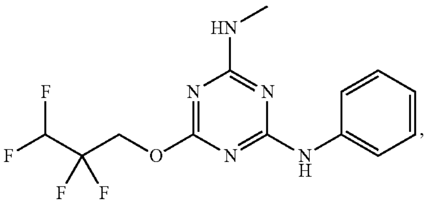, or a pharmaceutically acceptable salt thereof, effective to inhibit the release of an inflammatory cytokine from mammalian inflammatory cells.

In yet other aspects, the disclosure is directed to methods of inhibiting PDE IV activity in mammalian inflammatory cells by contacting the mammalian inflammatory cells with an amount of a compound of Formula (I):

(I)

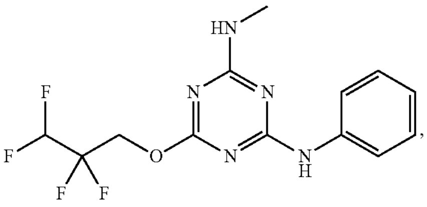, or a pharmaceutically acceptable salt thereof, that is effective to inhibit the PDE IV activity.

BRIEF DESCRIPTION OF THE DRAWINGS

FIG. 26 shows plasma and ear tissue concentrations of the compound of Formula (I) in Example 1

DETAILED DESCRIPTION OF ILLUSTRATIVE EMBODIMENTS

Figure 1:
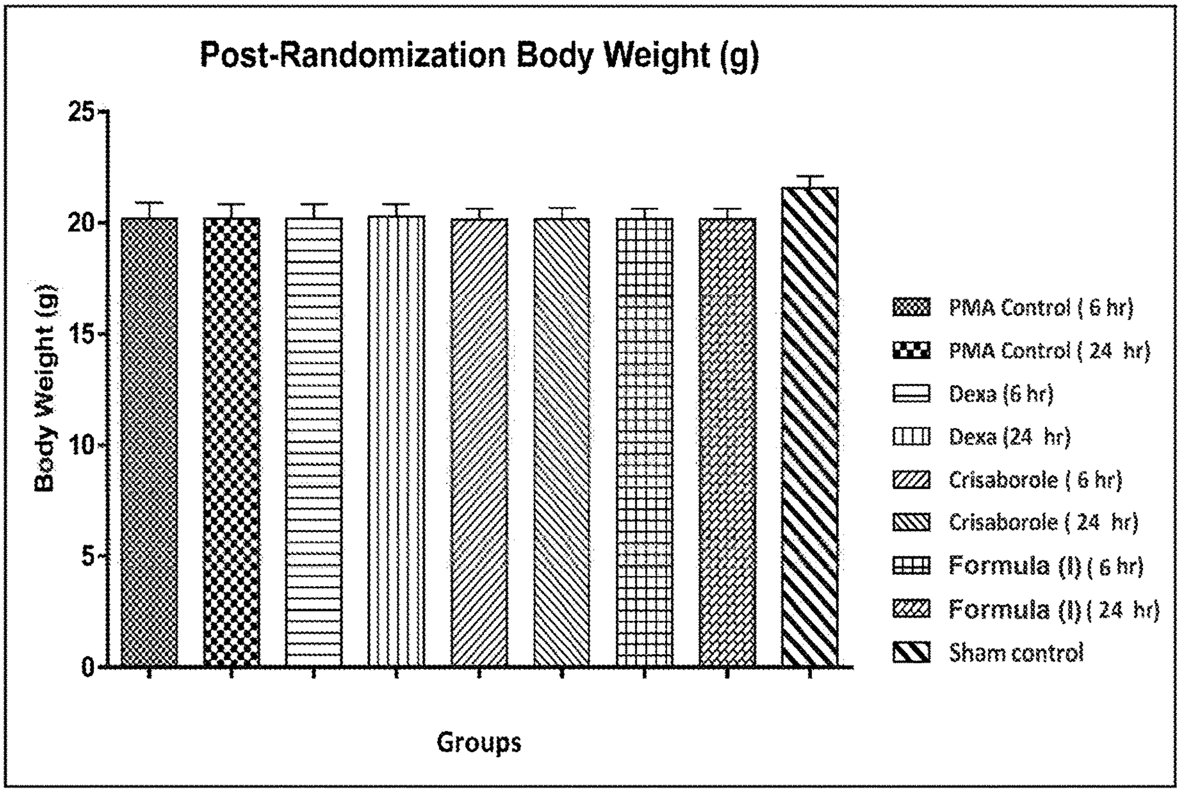
FIG. 1 shows the post randomization body weight by group in Example 1.
Figure 2:
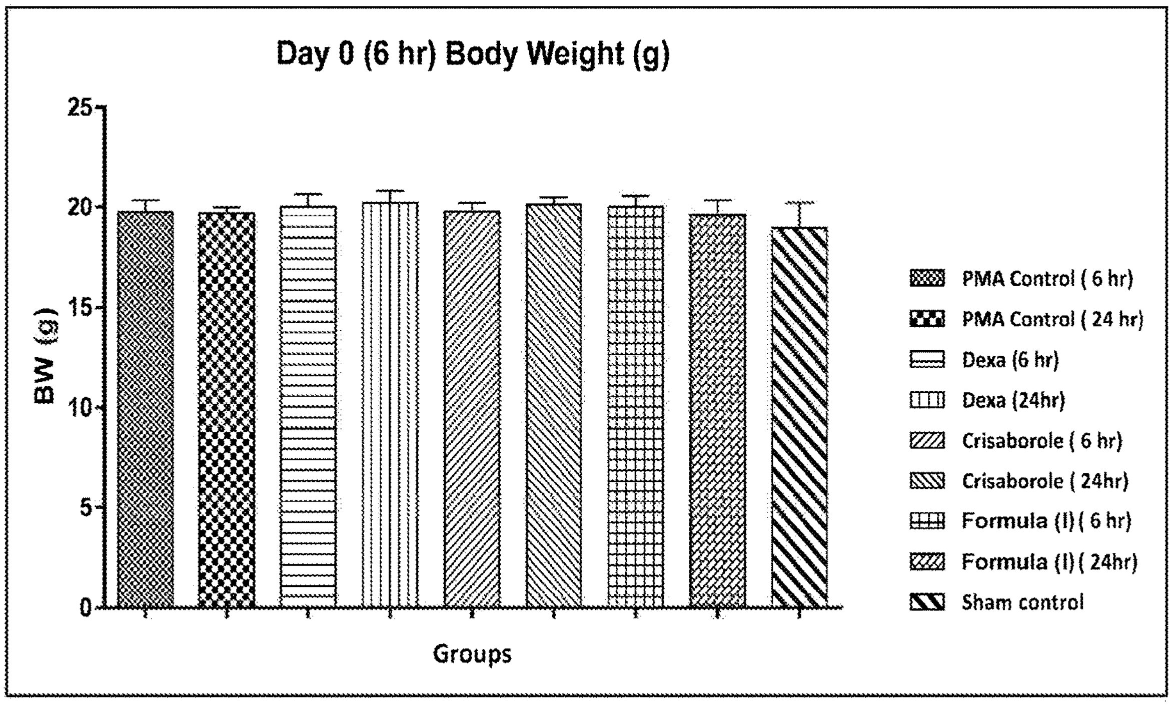
FIG. 2 shows body weight by group at 6 hours in Example 1.
Figure 3:
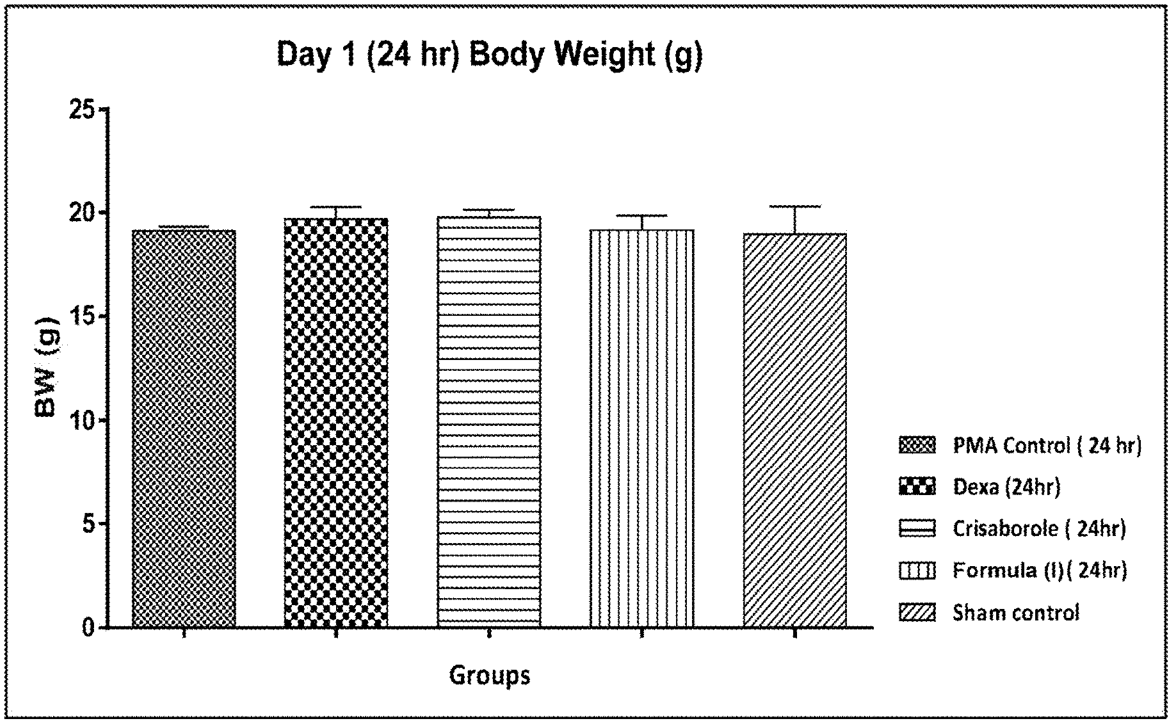
FIG. 3 shows body weight by group at 24 hours in Example 1.
Figure 4:
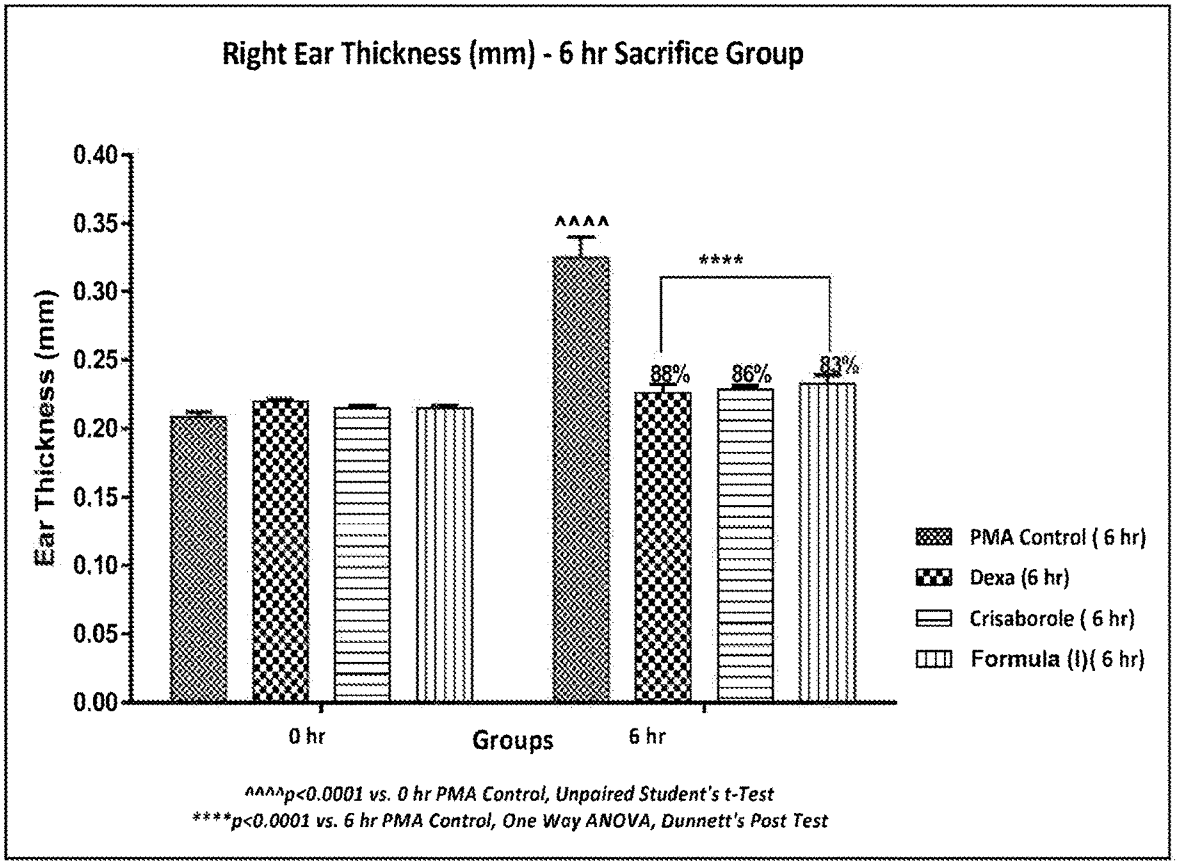
FIG. 4 shows the right ear thickness by group at 6 hours in Example 1.
Figure 5:
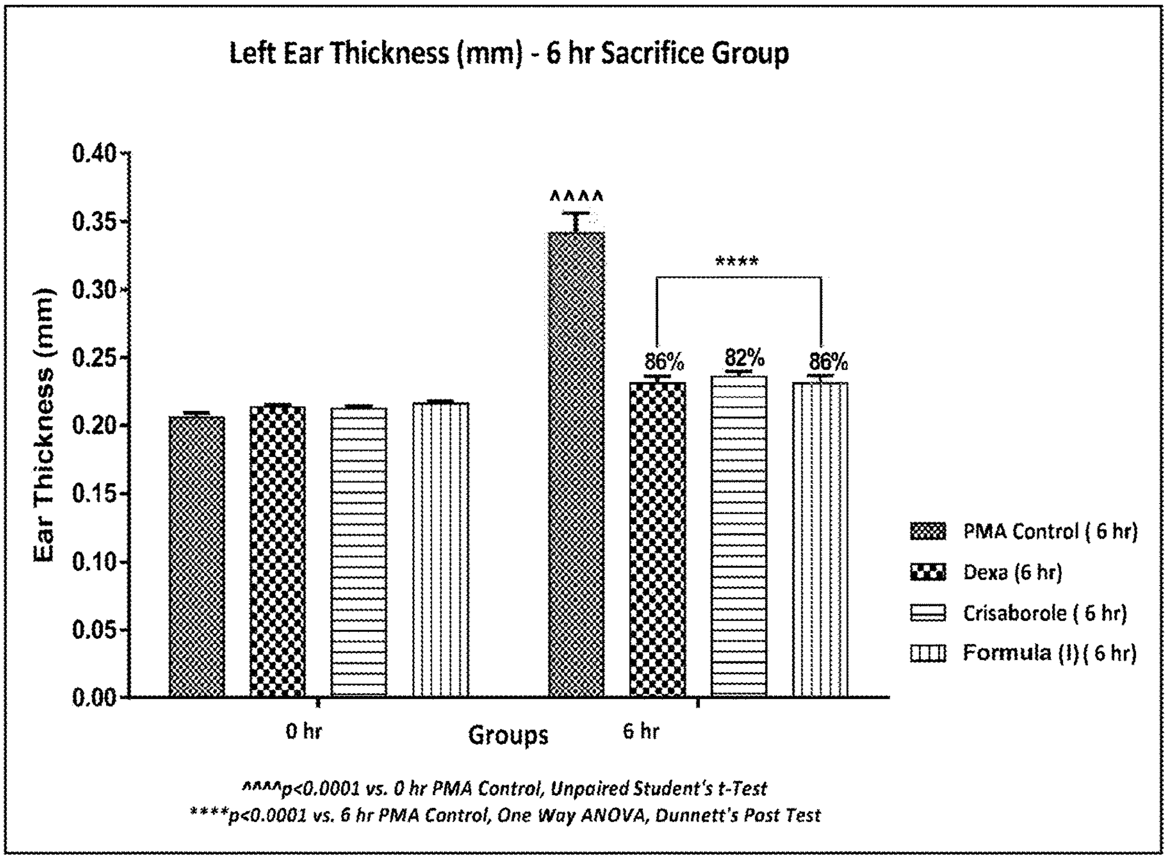
FIG. 5 shows the left ear thickness by group at 6 hours in Example 1.
Figure 6:
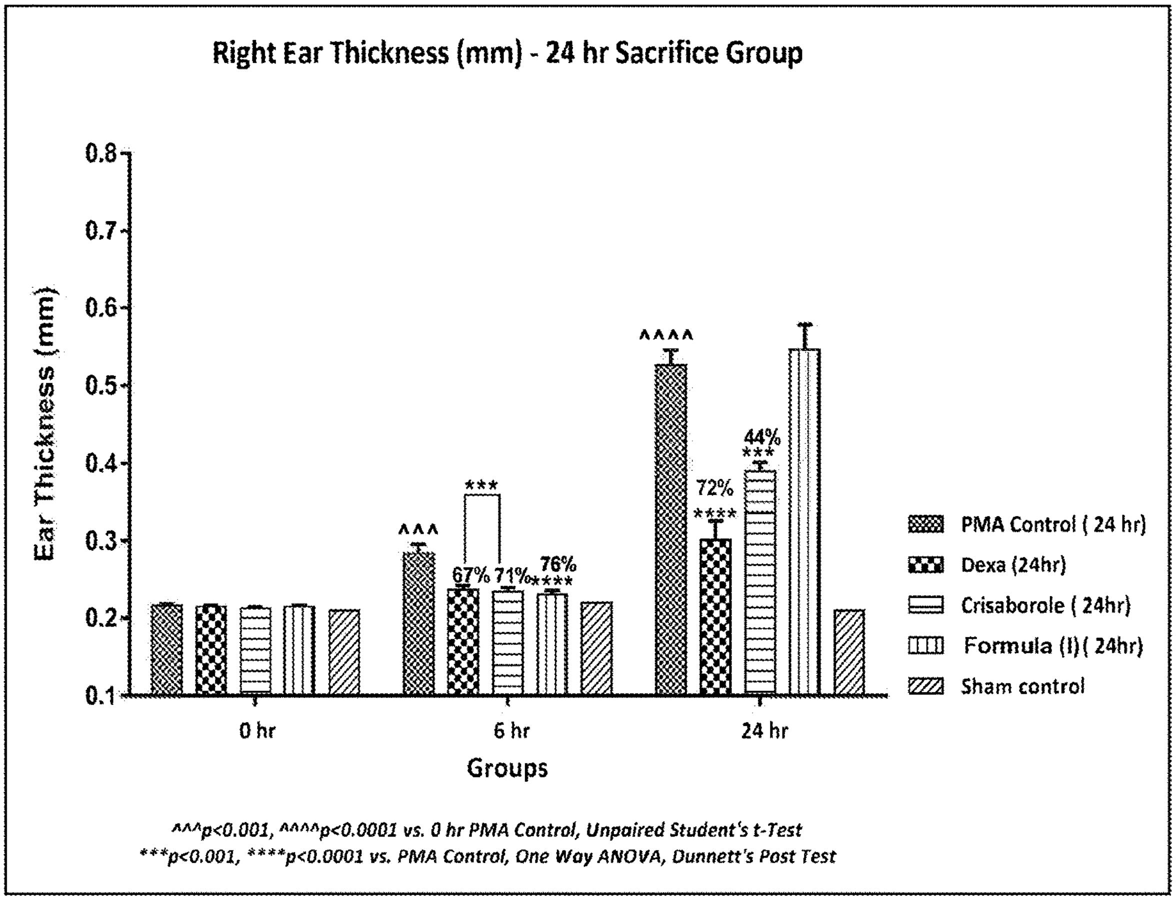
FIG. 6 shows the right ear thickness by group at 24 hours in Example 1.
Figure 7:
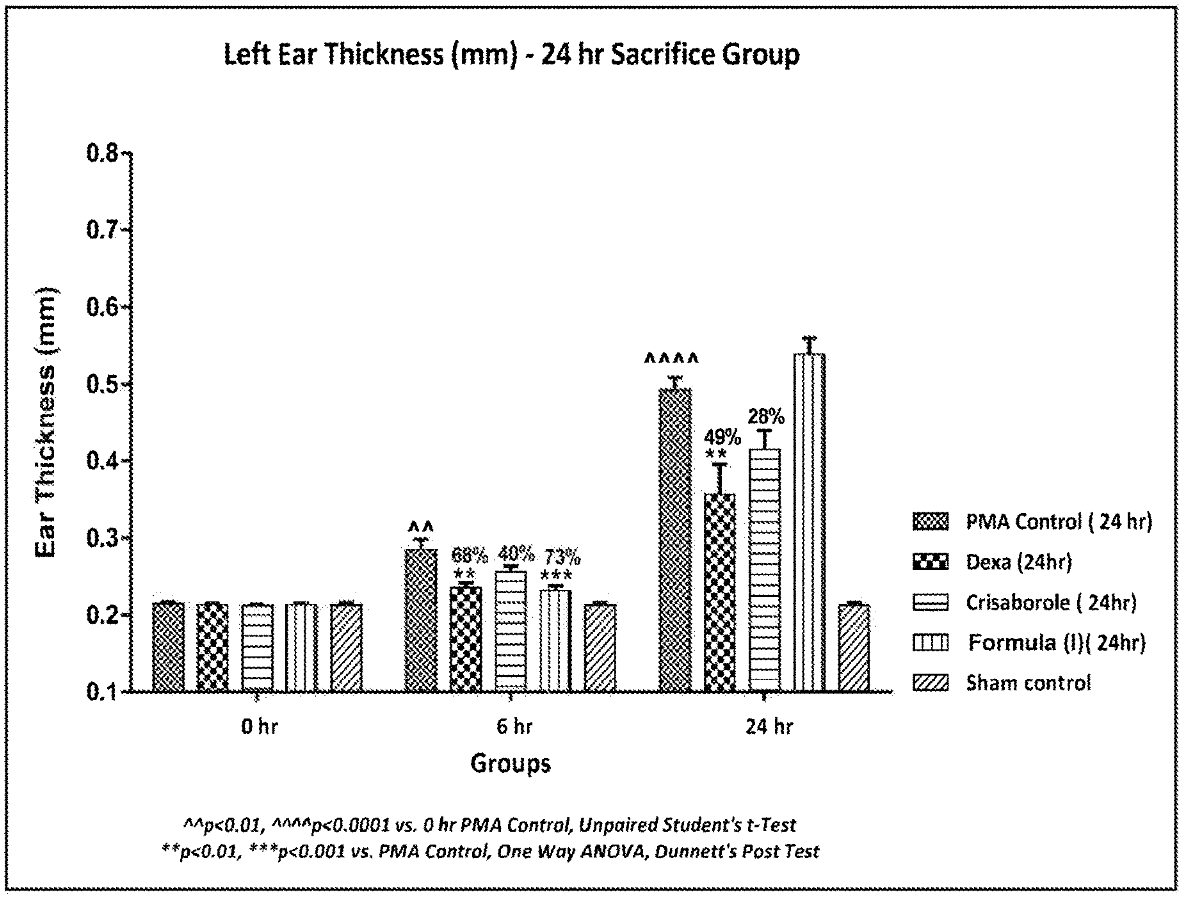
FIG. 7 shows the left ear thickness by group at 24 hours in Example 1.
Figure 8:
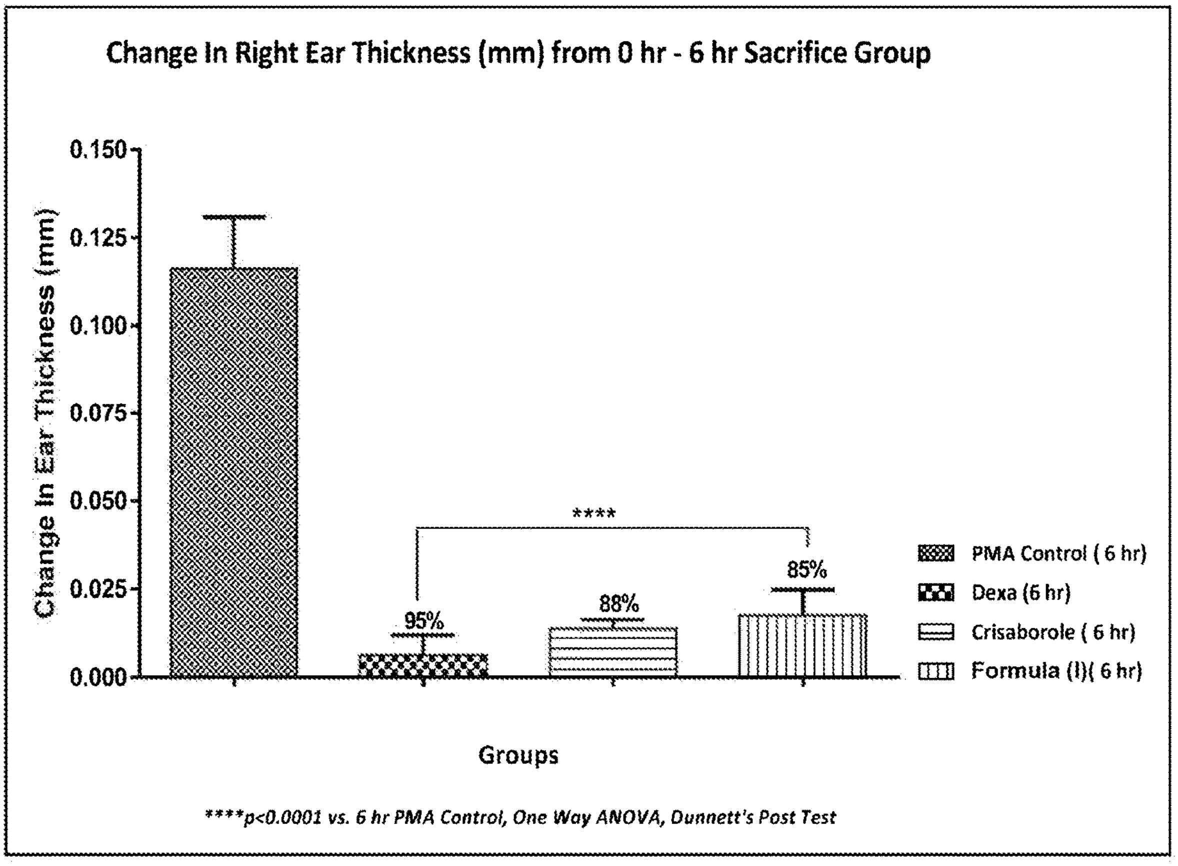
FIG. 8 shows the change in right ear thickness by group from 0-6 hours in Example 1.
Figure 9:
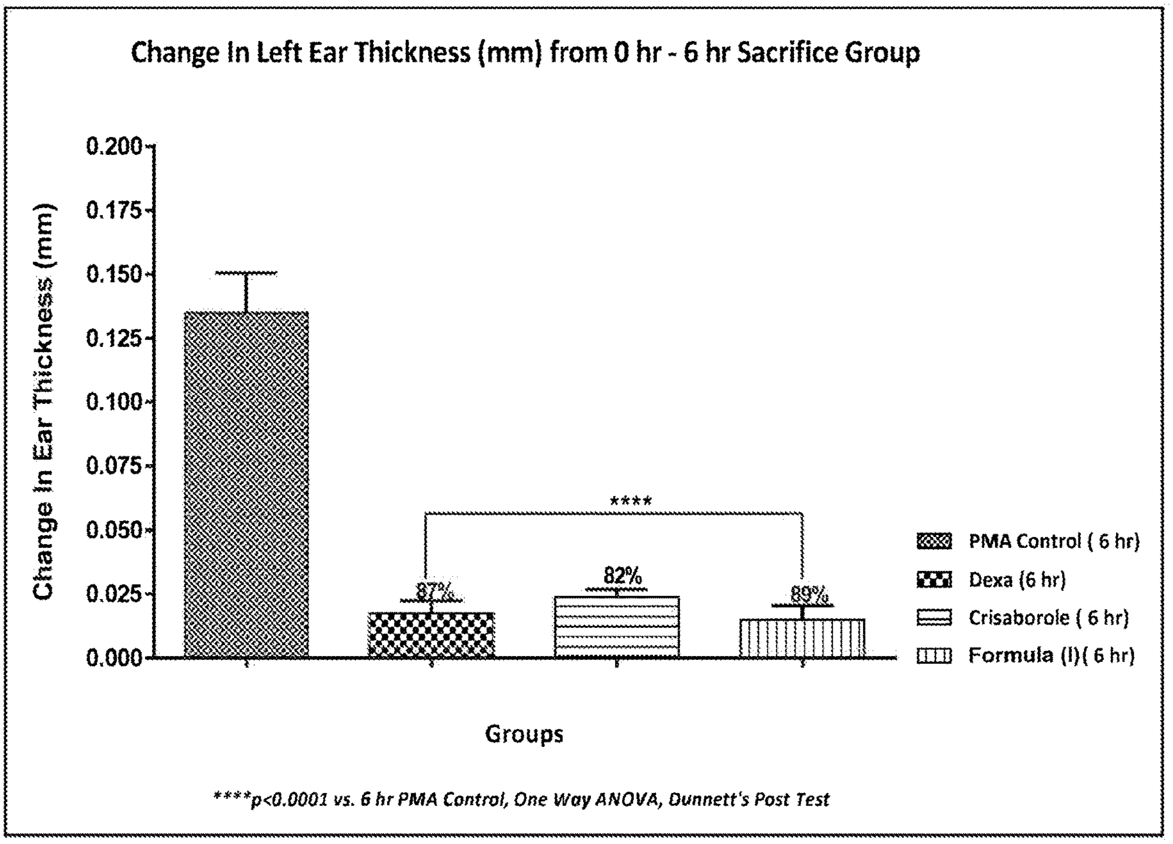
FIG. 9 shows the change in left ear thickness by group from 0-6 hours in Example 1.
Figure 10:
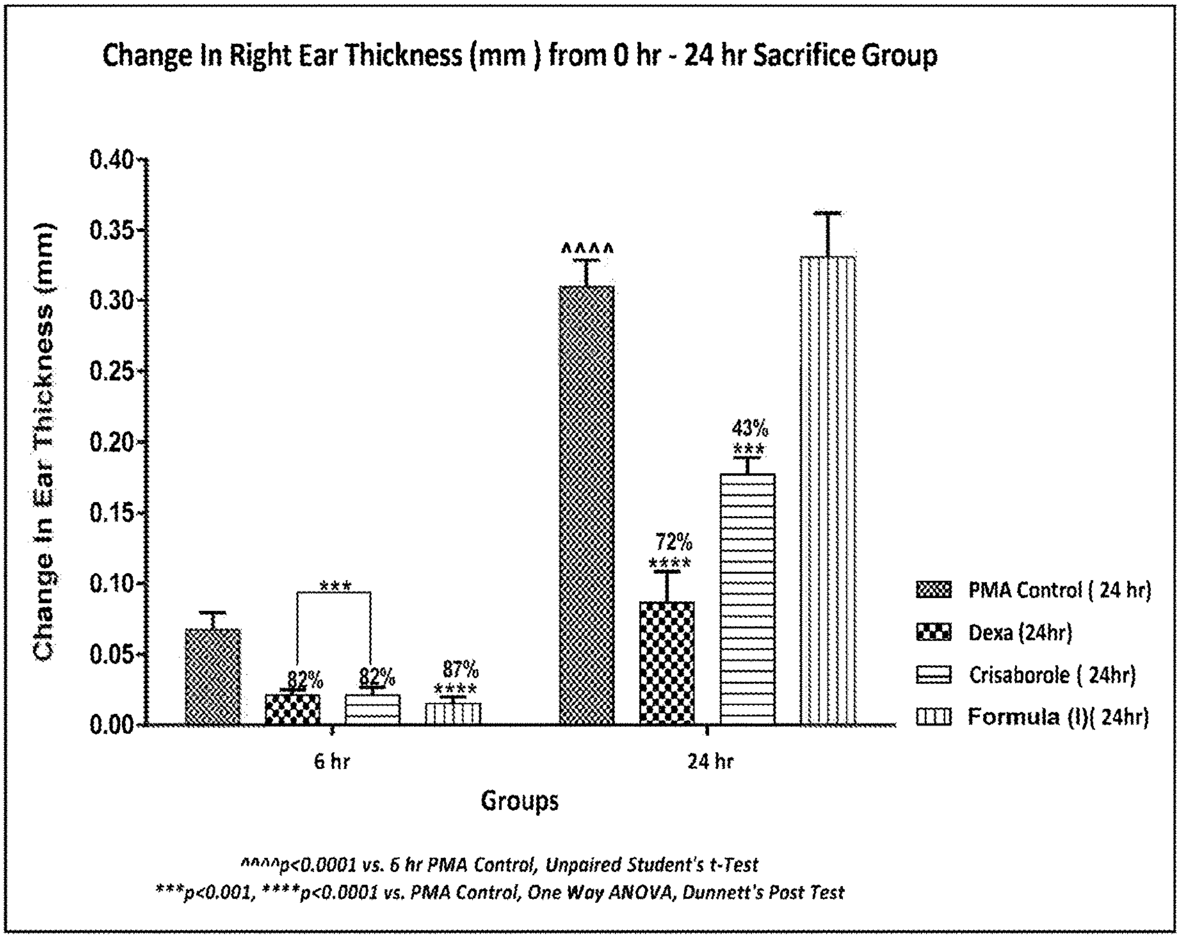
FIG. 10 shows the change in right ear thickness by group from 0-24 hours in Example 1.
Figure 11:
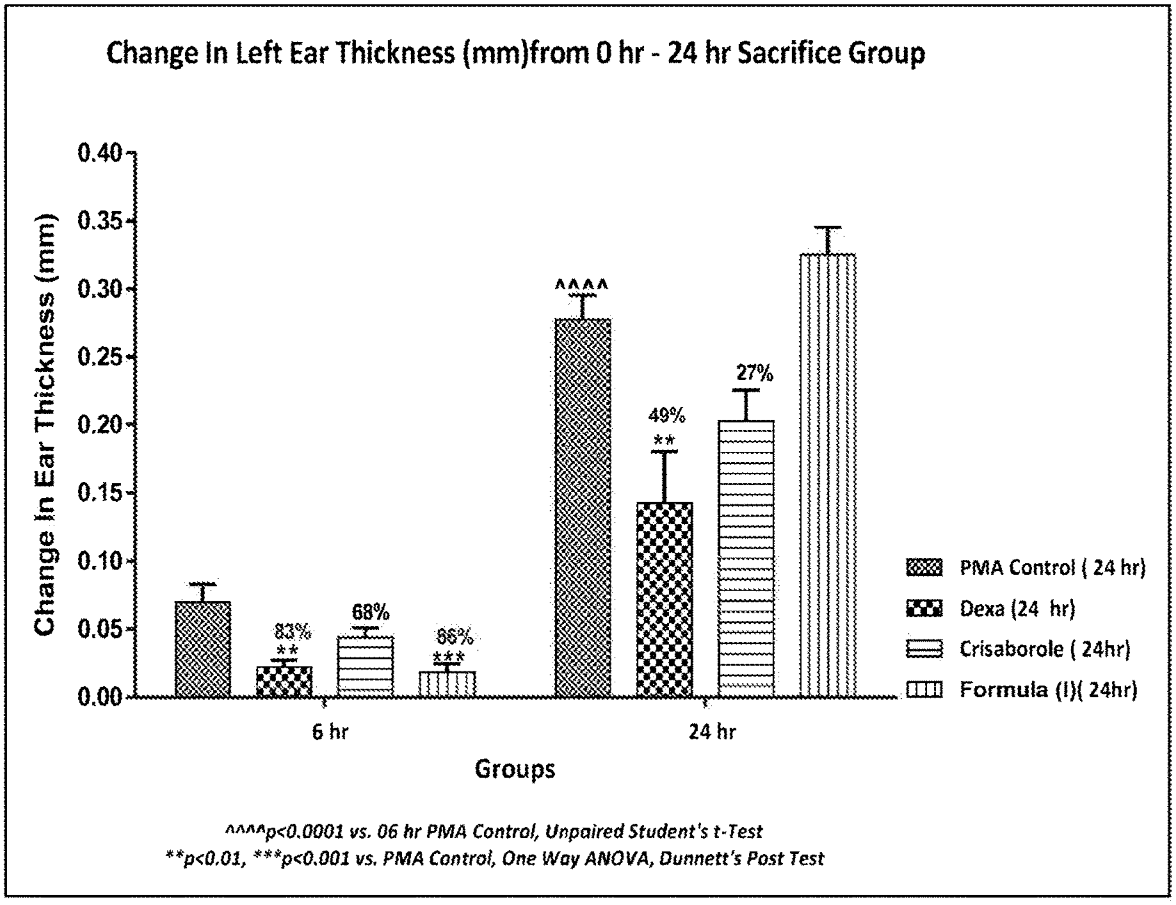
FIG. 11 shows the change in left ear thickness by group from 0-24 hours in Example 1.
Figure 12:
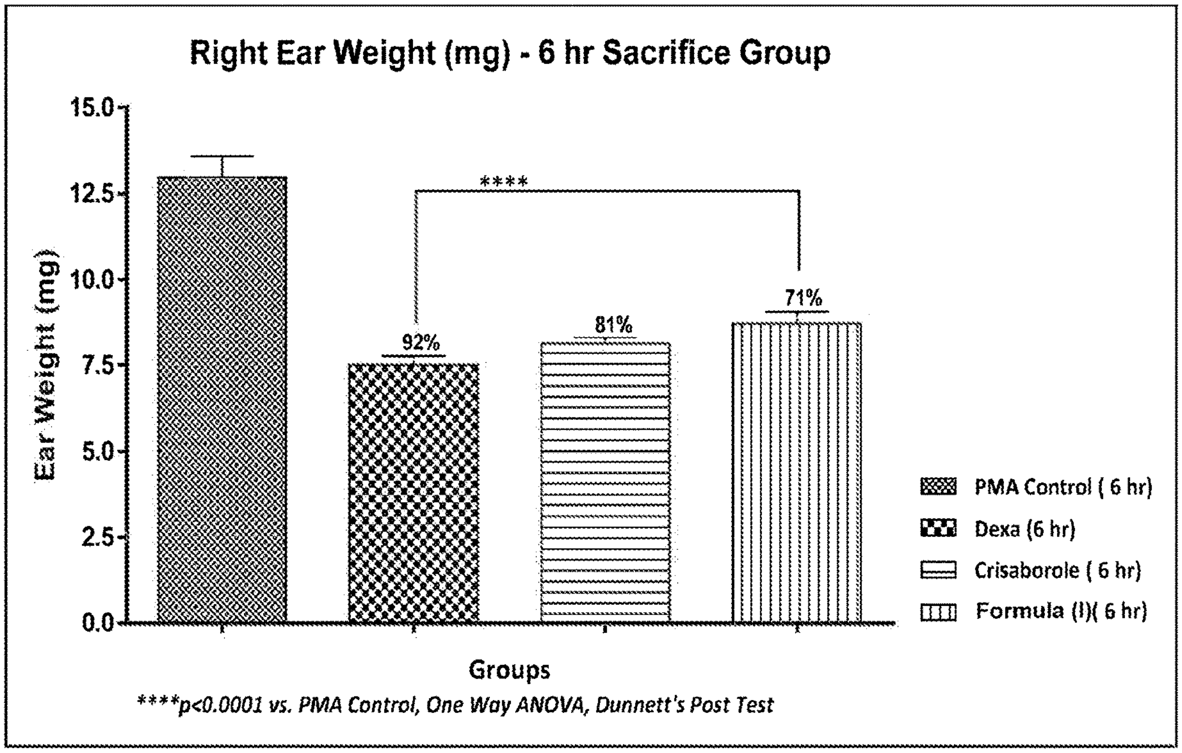
FIG. 12 shows the right ear weight by group at 6 hrs in Example 1.
Figure 13:
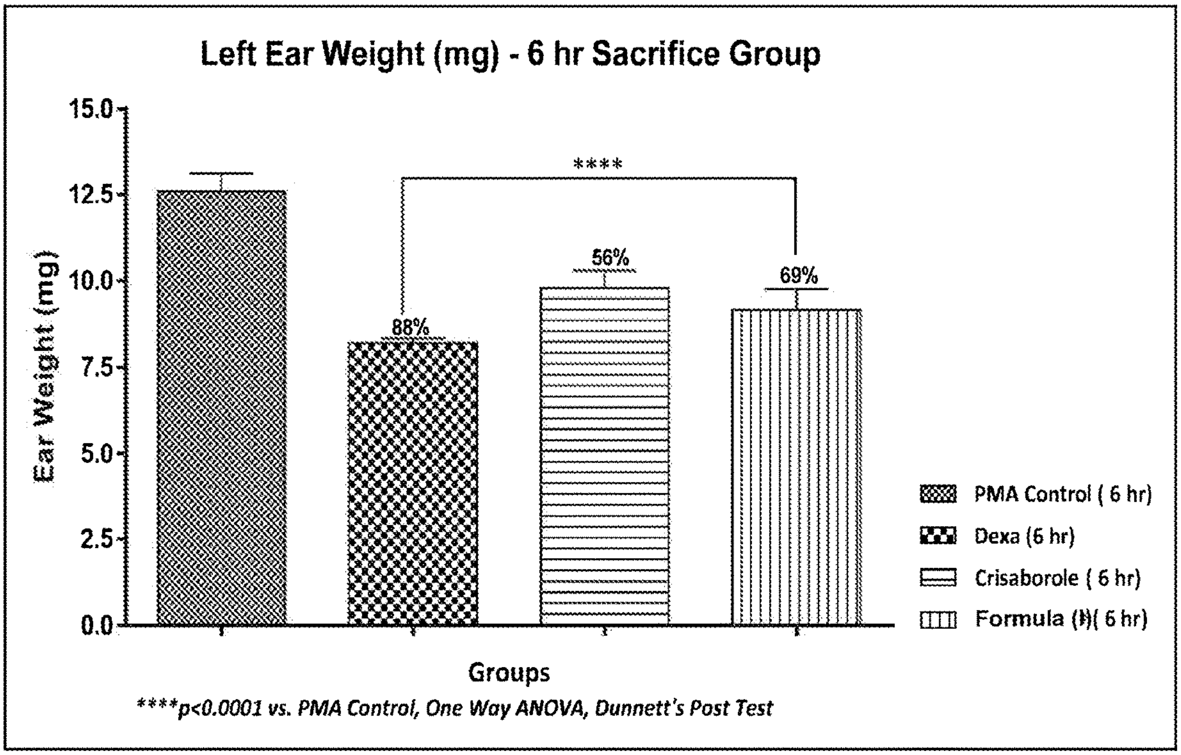
FIG. 13 shows the left ear weight by group at 6 hrs in Example 1.
Figure 14:
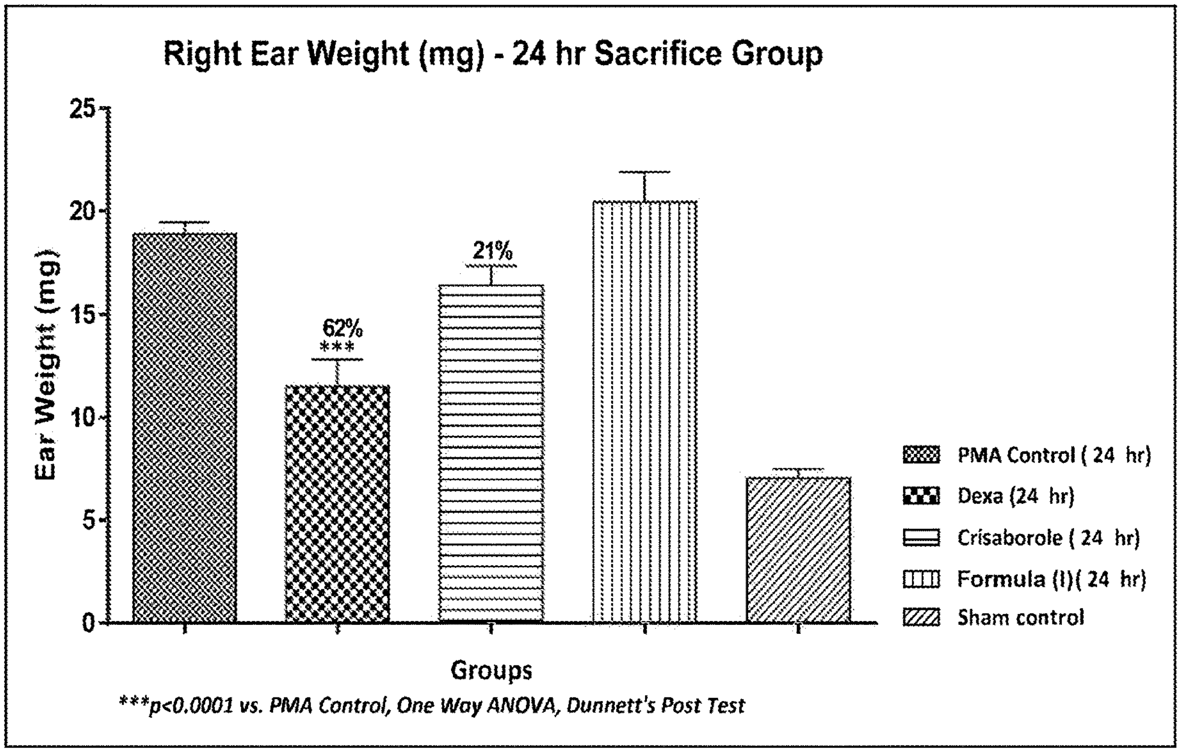
FIG. 14 shows the right ear weight by group at 24 hrs in Example 1.
Figure 15:
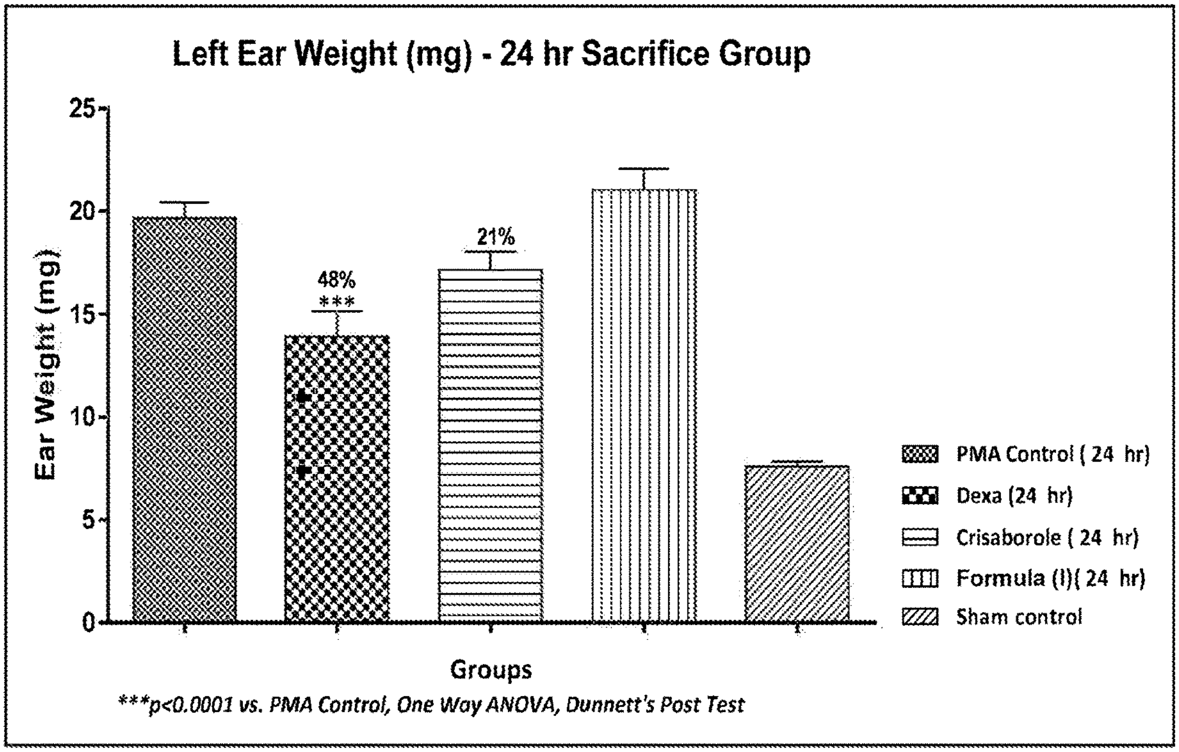
FIG. 15 shows the left ear weight by group at 24 hrs in Example 1.
Figure 16:
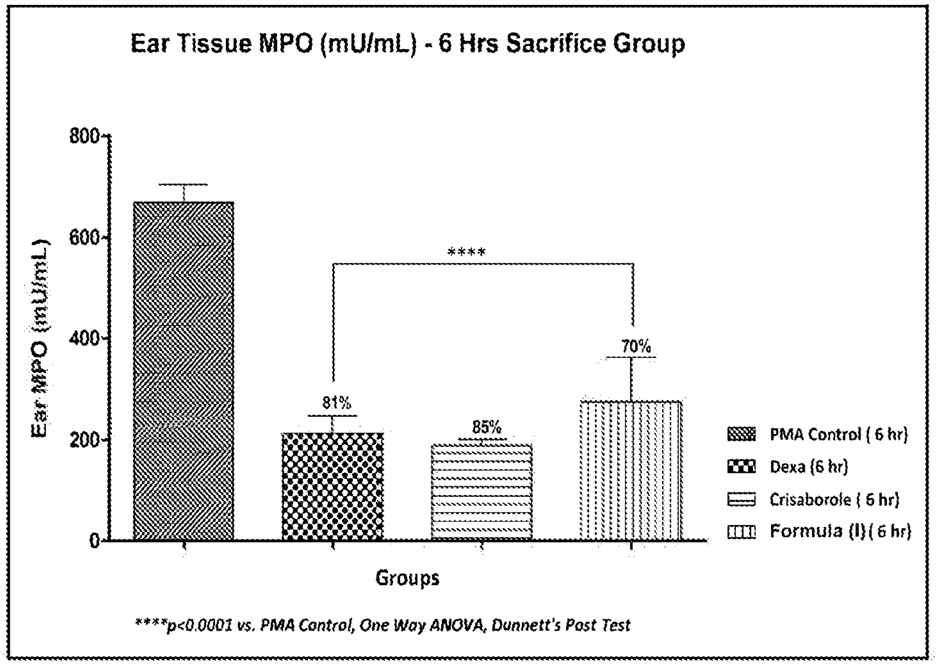
FIG. 16 shows the ear tissue MPO by group at 6 hrs in Example 1.
Figure 17:
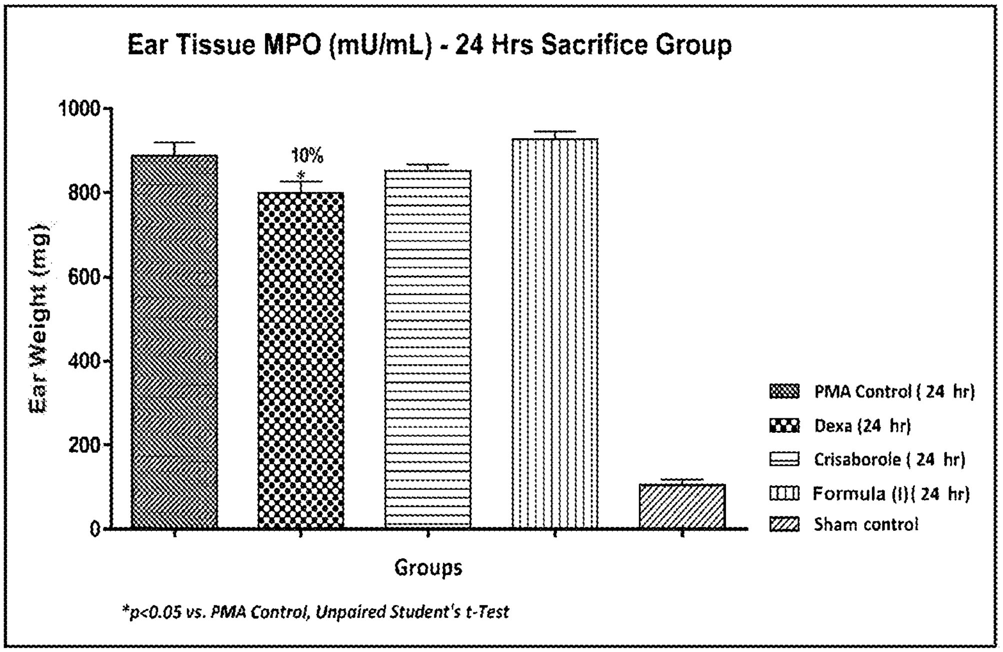
FIG. 17 shows the ear tissue MPO by group at 24 hrs in Example 1.
Figure 18:
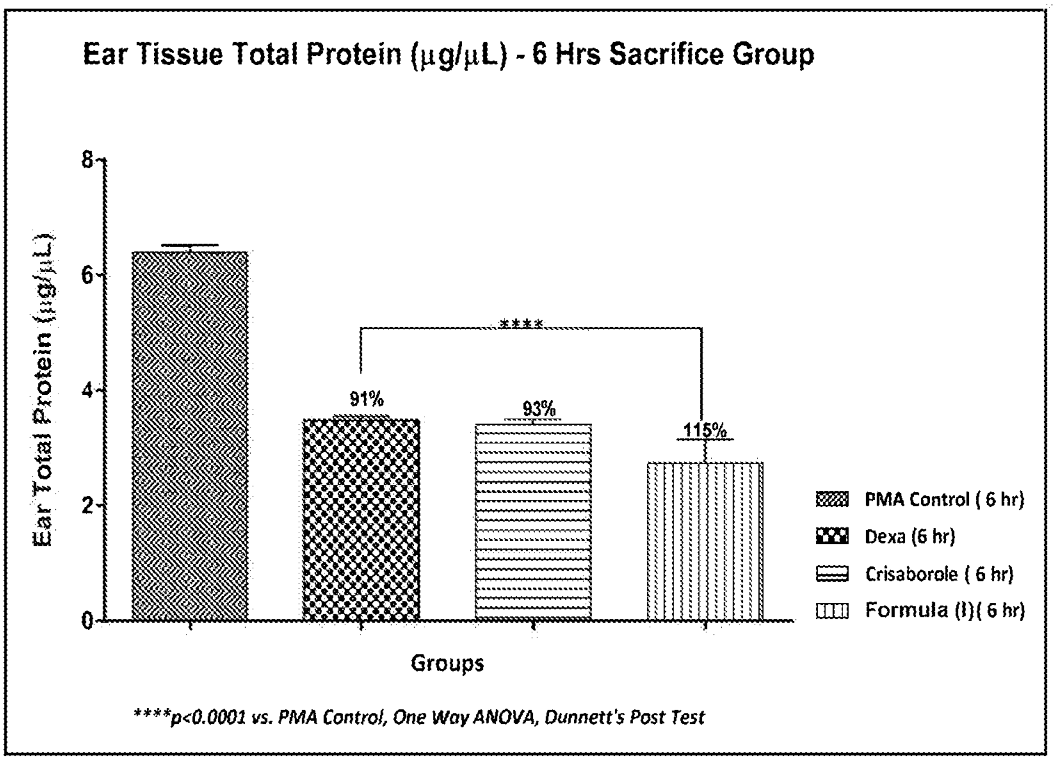
FIG. 18 shows the ear tissue total protein by group at 6 hours in Example 1.
Figure 19:
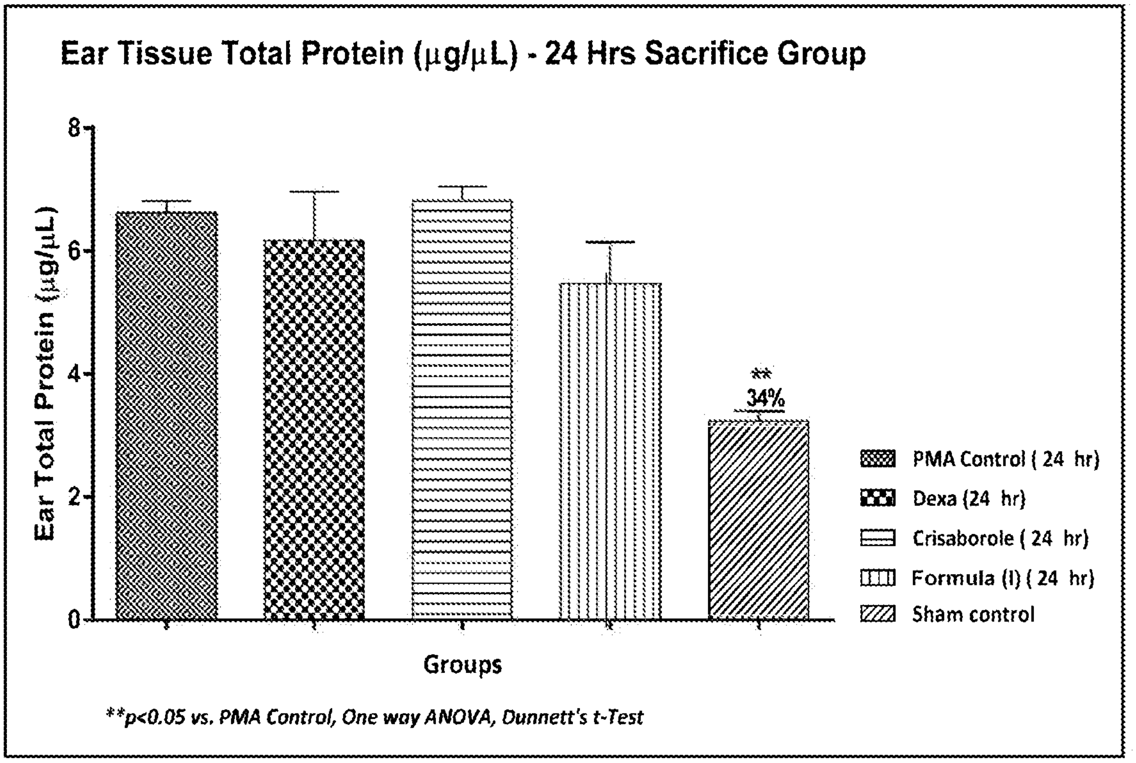
FIG. 19 shows the ear tissue total protein by group at 24 hours in Example 1.
Figure 20:
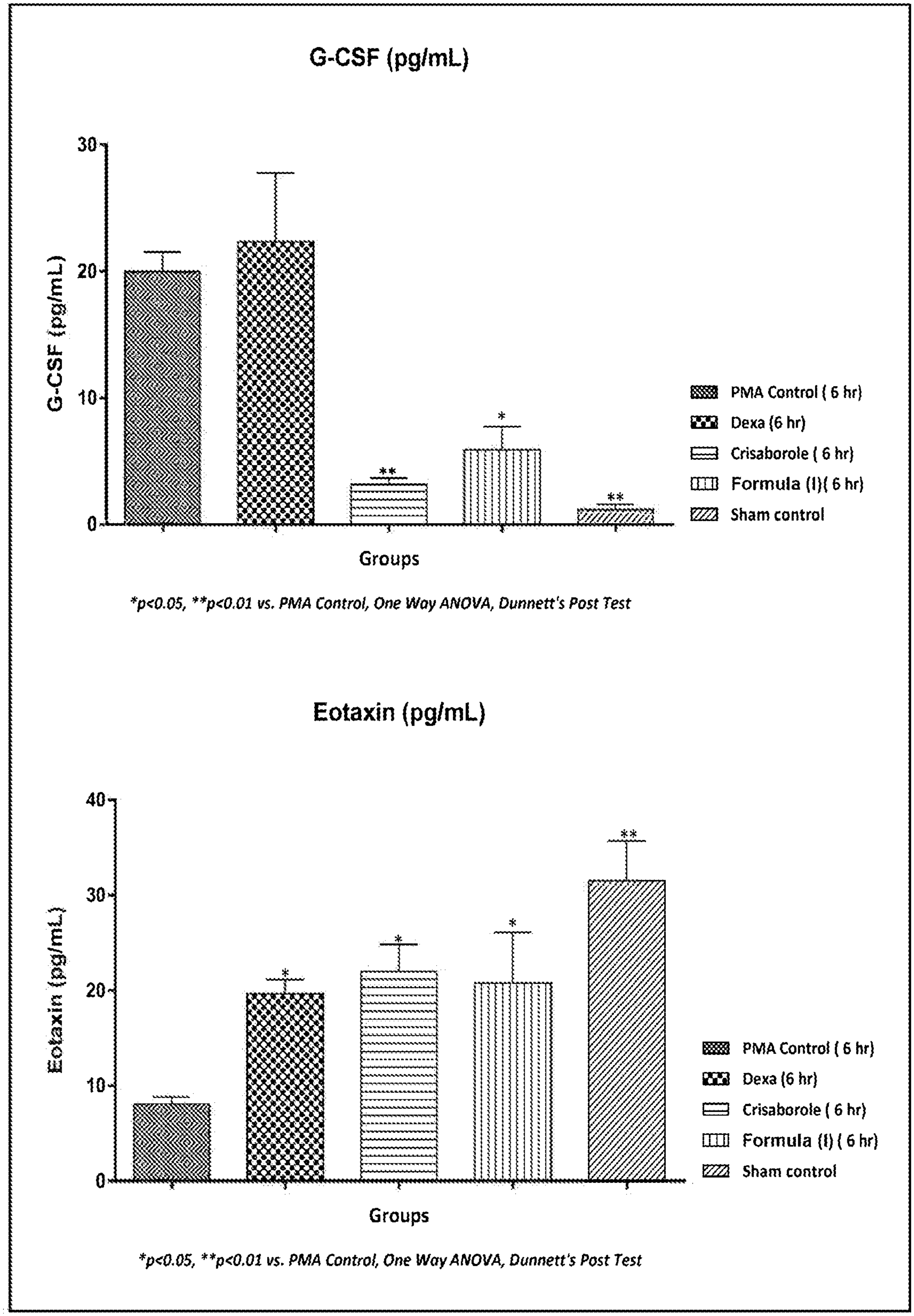
FIG. 20 shows G-CSF and eotaxin in ear tissue homogenate by group in Example 1.
Figure 21:
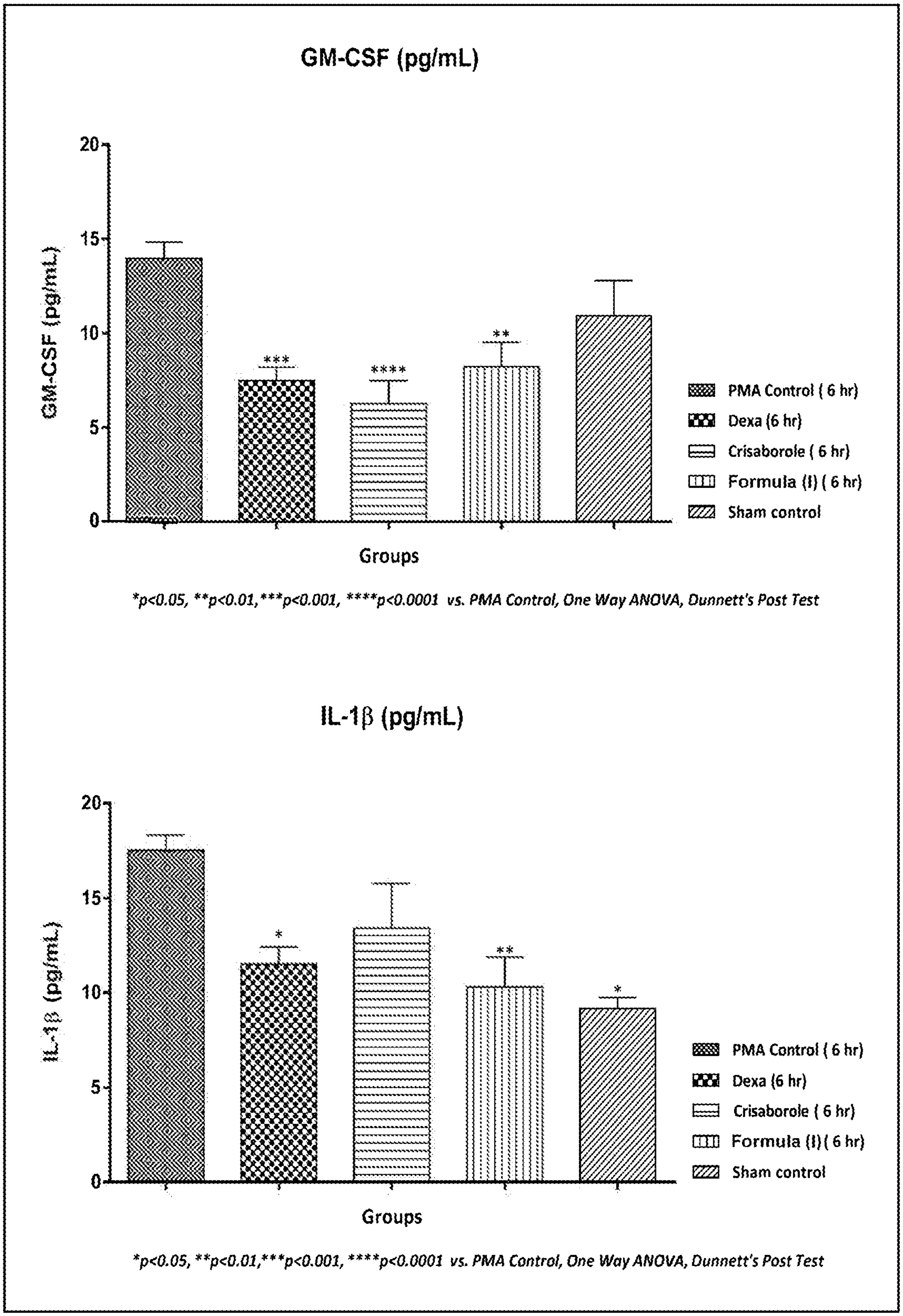
FIG. 21 shows GM-CSF and IL-1ß in ear tissue homogenate by group in Example 1.
Figure 22:
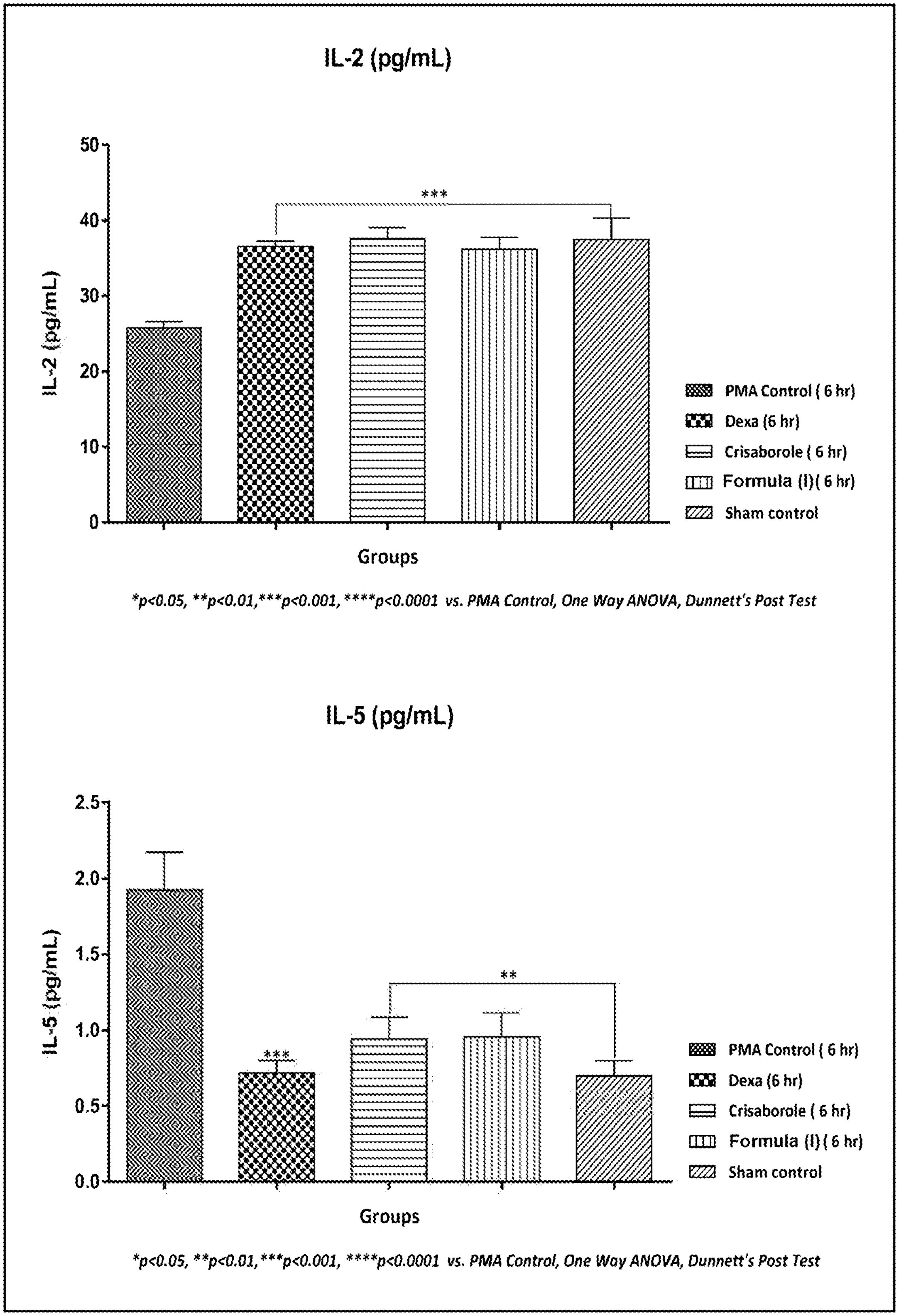
FIG. 22 shows IL-2 and IL-5 in ear tissue homogenate by group in Example 1.
Figure 23:
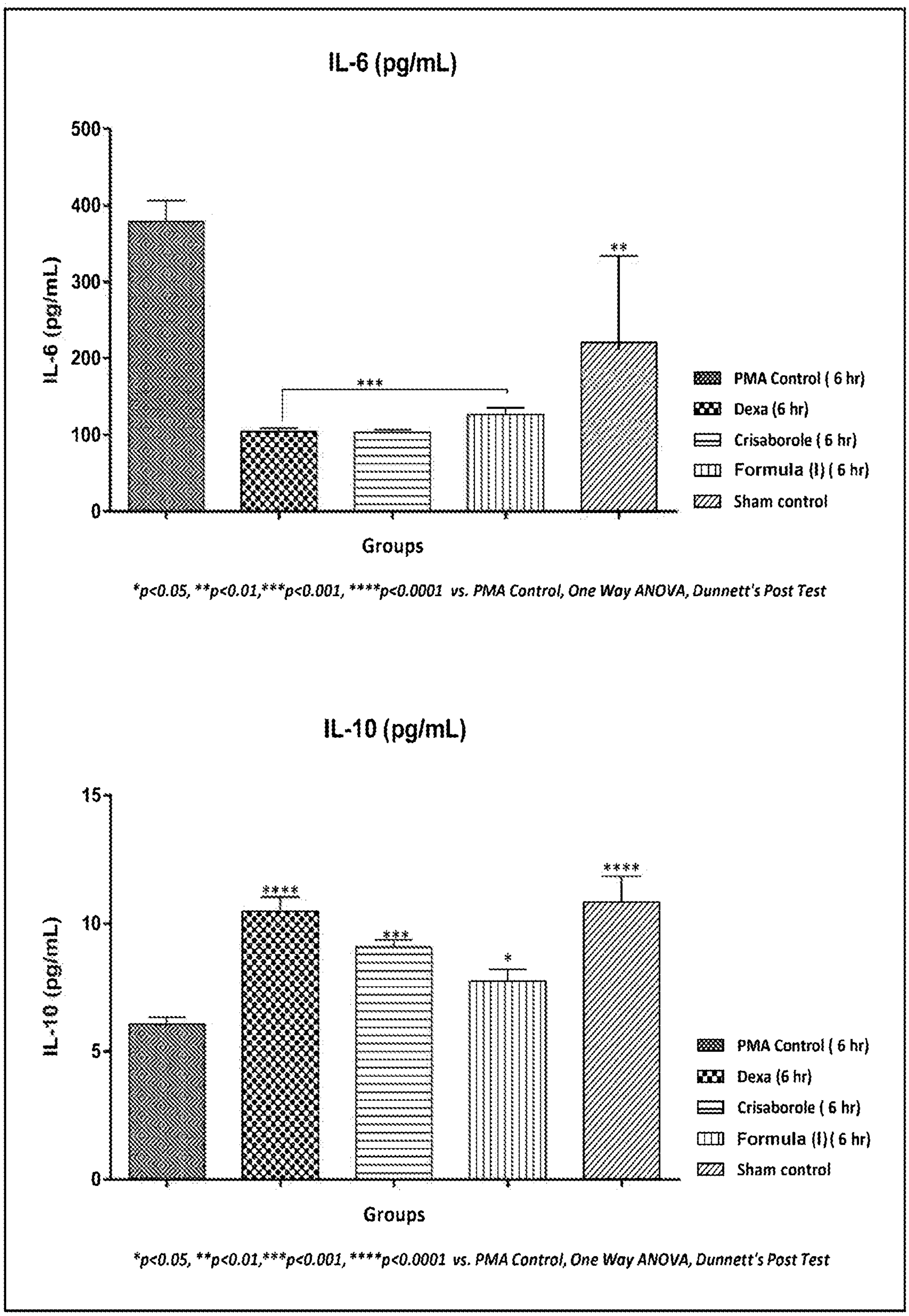
FIG. 23 shows IL-6 and IL-10 in ear tissue homogenate by group in Example
1.
Figure 24:
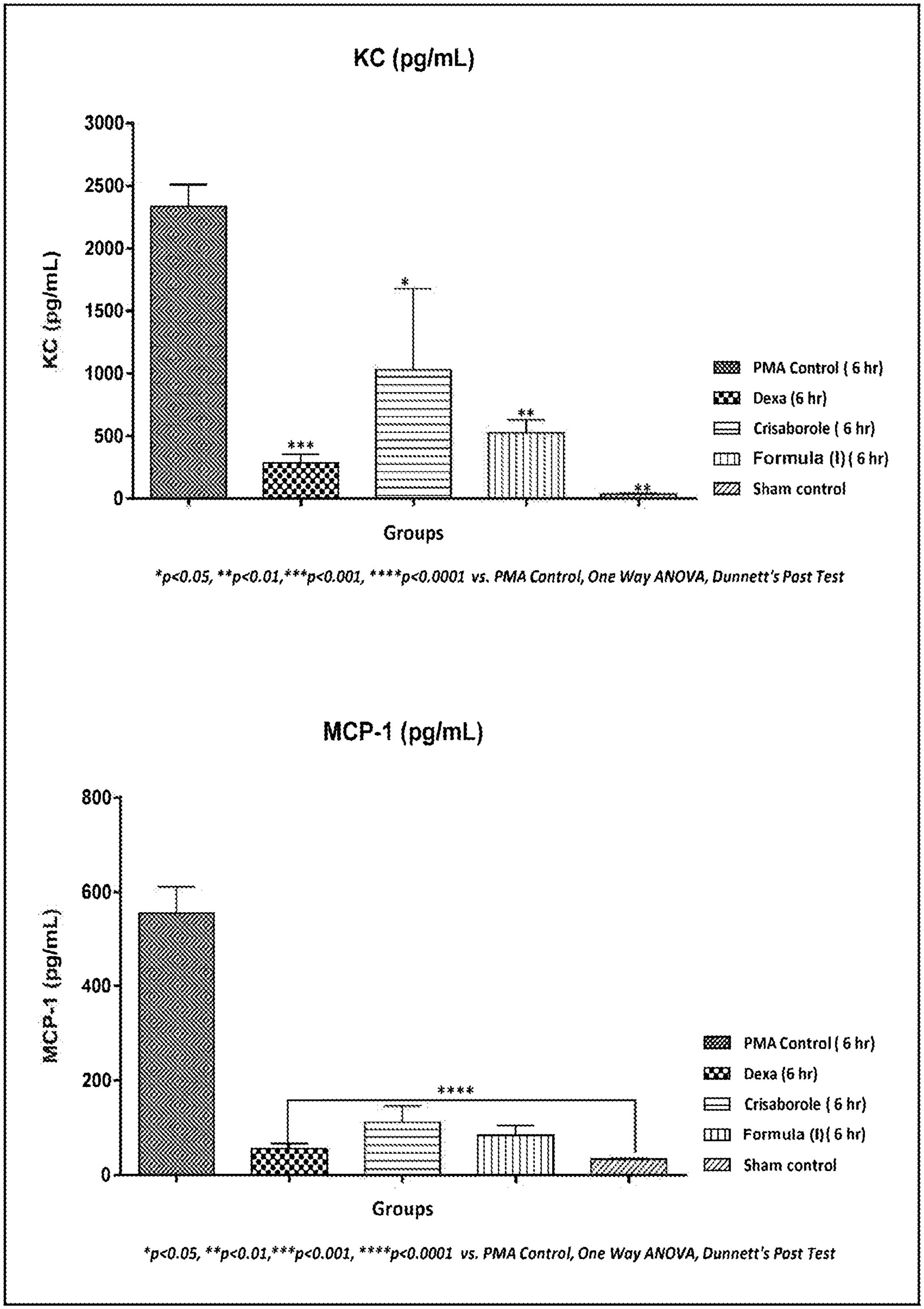
FIG. 24 shows KC (keratinocyte chemotactic-like) and MCP-1 (Monocyte Chemotactic Protein-1) in ear tissue homogenate by group in Example 1.
Figure 25:
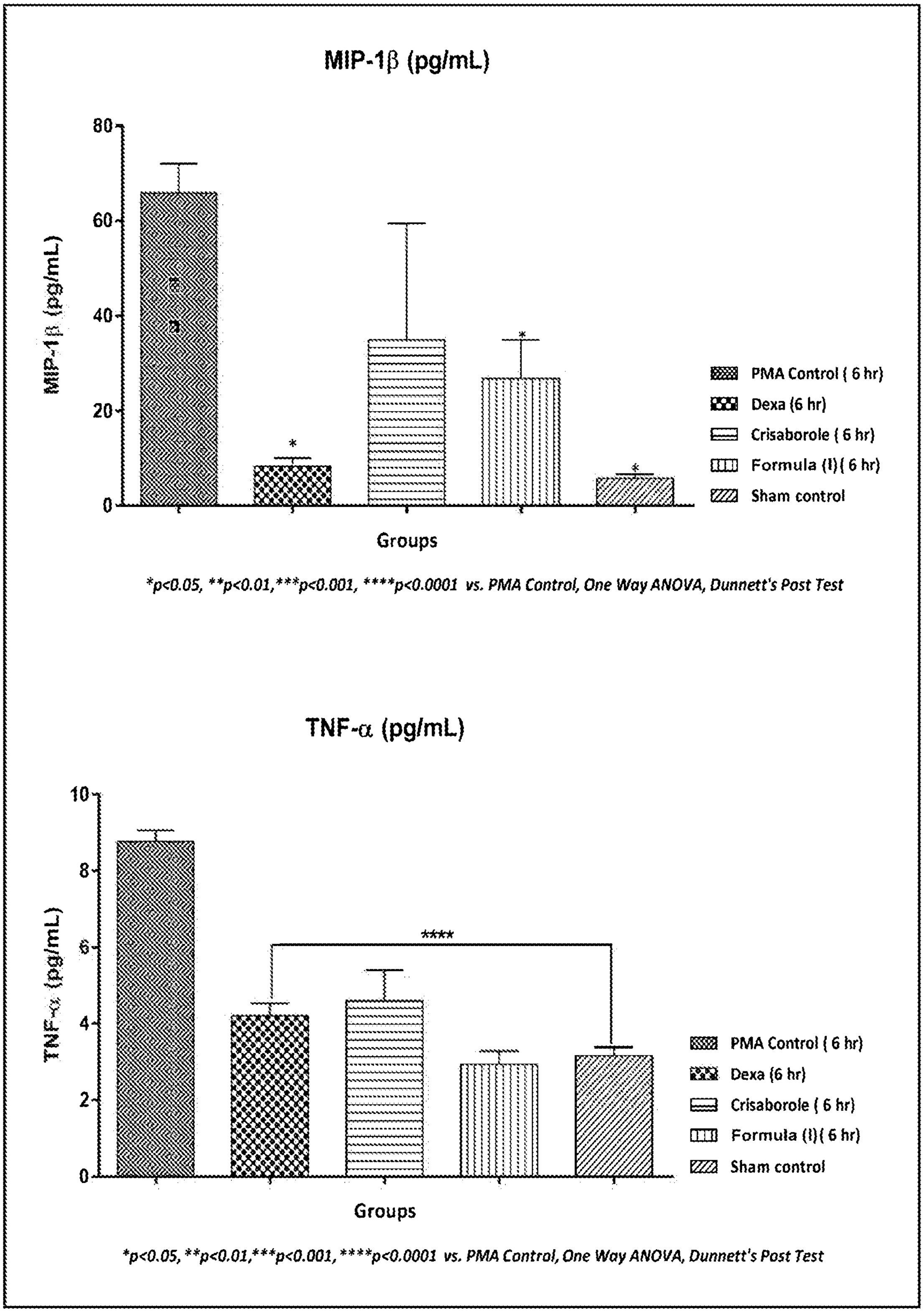
FIG. 25 shows MIP-1β and TNF-α in ear tissue homogenate by group in Example 1.

The present invention may be understood by reference to the following detailed description which forms a part of this disclosure. The invention is not limited to the specific methods, conditions or parameters described and/or shown herein, and the terminology used herein is for the purpose of describing particular embodiments by way of example only and is not intended to be limiting of the claimed invention.

Scientific and technical terms used in connection with the present application shall have the meanings that are commonly understood by those of ordinary skill in the art, unless otherwise defined herein.

In some aspects, the disclosure is directed to a method for treatment of a patient with a phosphodiesterase IV (PDEIV)-mediated disease or condition comprising administering to the patient an amount of a compound of Formula (I)

(I)

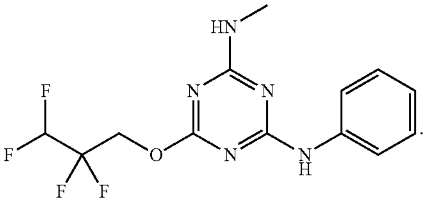

or a pharmaceutically acceptable salt thereof, effective to treat the disease or condition.

As used herein, the term "treatment" refers to any indicia of success in the treatment or amelioration of the PDEIV-mediated disease or conditions, e.g., an inflammatory disease or condition, including any objective or subjective parameter such as abatement: remission: reduction of symptoms or making the disease or condition more tolerable to the patient: slowing in the rate of degeneration or decline: making the final point of degeneration less debilitating: or improving a patient's physical or mental well-being. The treatment or amelioration of symptoms can be based on objective or subjective parameters, including the results of a physical examination, neuropsychiatric exams, and/or a psychiatric evaluation. The term "treatment" and conjugations thereof, include prevention of the disease or condition.

As used herein, the terms "patient," or "subject," are used interchangeably and refer to a living organism suffering from or prone to a disease or condition that can be treated by administration of the compound of Formula (I). Non-limiting examples include humans, other mammals, bovines, rats, mice, dogs, monkeys, goat, sheep, cows, deer, and other non-mammalian animals.

In some embodiments, the patient is a human.

As used herein, the phrase "phosphodiesterase IV (PDEIV)-mediated disease or condition" refers to any disease or condition characterized by, or resulting from, PDEIV activity. PDEIV-mediated diseases or conditions include, for example, a variety of inflammatory disorders, allergic disorders, immunological disorders, CNS disorders, atherosclerosis, and vascular inflammation. Such disorders include asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder), depression, or pain. See, e.g., WO 2004/024728 A2. Use of PDEIV inhibitors in treatment of inflammatory diseases generally, is described in, for example. Press, Neil J, and Katharine H. Banner. "2 PDE4 Inhibitors—A Review of the Current Field." Progress in Medicinal Chemistry (2009): 37: Dastidar. Sunanda G., Deepa Rajagopal, and Abhijit Ray "Therapeutic benefit of PDE4 inhibitors in inflammatory diseases." *Current Opinion in Investigational Drugs* 8.5 (2007): 364; Schafer, P. H., et al. "Apremilast is a selective PDE4 inhibitor with regulatory effects on innate immunity." *Cellular signalling* 26.9 (2014): 2016-2029; Li, Heng, Jianping Zuo, and Wei Tang. "Phosphodiesterase-4 inhibitors for the treatment of inflammatory diseases." *Frontiers in pharmacology* 9 (2018): 1048.

Use of PDEIV inhibitors in treatment of inflammatory skin disorders is described in, for example, Makins, Caitlyn, Ravina Sanghera, and Parbeer S. Grewal. "Off-Label Therapeutic Potential of Crisaborole." *Journal of Cutaneous Medicine and Surgery* (2020): 1203475420909794; Kitzen, Jan M., et al. "Crisaborole and Apremilast: PDE4 Inhibitors with Similar Mechanism of Action, Different Indications for Management of Inflammatory Skin Conditions." (2018); Dastidar, Sunanda G., Deepa Rajagopal, and Abhijit Ray. "Therapeutic benefit of PDE4 inhibitors in inflammatory diseases." *Current Opinion in Investigational Drugs* 8.5 (2007): 364; J. M. Hanifin et al., "Type 4 phosphodiesterase inhibitors have clinical and in vitro anti-inflammatory effects in atopic dermatitis", *J. Invest. Dermatol.,* 1996, 107(1), 51-56 (atopic dermatitis); C. E. M. Griffiths et al., "Randomized comparison of the type 4 phosphodiesterase inhibitor cipamfylline cream, cream vehicle and hydrocortisone 17-butyrate cream for the treatment of atopic dermatitis," *Br. J. Dermatol.,* 2002, 147(2), 299-307 (atopic dermatitis); T. C. Roos et al., "Recent advances in treatment strategies for atopic dermatitis," *Drugs.* 2004, 64(23), 2639-2666 (atopic dermatitis, see e.g. page 2657 and refs. 201-209 therein); A. M. Doherty, *Current Opinion Chem. Biol.,* 1999, 3(4), 466-473 (atopic dermatitis; e.g. see p. 470); and H. J. Dyke et al., *Expert Opinion Invest. Drugs.* 2002, 11(1), 1-13 (atopic dermatitis; e.g. see p. 7 and refs. 74, 75 and 76 cited therein); W. Bäumer et al., *Eur. J. Pharmacol.,* 2002, 446, 195-200 and W. Bäumer et al., *J. Pharmacy Pharmacol.,* 2003, 55, 1107-1114 (allergic dermatitis).

Use of PDEIV inhibitors in COPD is described in S. L. Wolda, *Emerging Drugs.* 2000, 5(3), 309-319; Z. Huang et al., *Current Opinion in Chemical Biology,* 2001, 5: 432-438; H. J. Dyke et al., *Expert Opinion on Investigational Drugs, January* 2002, 11(1), 1-13; C. Burnouf et al., *Current Pharmaceutical Design,* 2002, 8(14), 1255-1296; A. M. Doherty, *Current Opinion Chem. Biol.,* 1999, 3(4), 466-473; A. M. Vignola, Respiratory *Medicine,* 2004, 98, 495-503; D. Spina, Drugs. 2003, 63(23), 2575-2594; and references cited in the aforementioned publications; and G. Krishna et al., *Expert Opinion on Investigational Drugs.* 2004, 13(3), 255-267 (see especially pp. 259-261 and refs. 102-111 and 201 therein); C. H. Compton et al., *The Lancet,* 2001, vol. 358, 265-270), E. Gamble et al., *Am. J. Respir. Crit. Care Med.,* 2003, 168, 976-982); R. D. Border et al., *Chest.* 2003, vol. 124 Suppl. 4, p. 170S (abstract) and J. D. Eddleston et al., *Am. J. Respir. Crit. Care Med.,* 2001, 163, A277 (abstract); B. J. Lipworth, *The Lancet,* 2005, 365, 167-175, and refs 49-50 therein); S. L. Wolda, *Emerging Drugs.* 2000, 5(3), 309-319).

Use of PDEIV inhibitors in asthma is described in M. A. Giembycz, *Drugs. February* 2000, 59(2), 193-212; Z. Huang et al., *Current Opinion in Chemical Biology,* 2001, 5: 432-438; H. J. Dyke et al., *Expert Opinion on Investigational Drugs*, January 2002, 11(1), 1-13; C. Burnouf et al., *Current Pharmaceutical Design,* 2002, 8(14), 1255-1296; A. M. Doherty, *Current Opinion Chem. Biol.,* 1999, 3(4), 466-473; P. J. Barnes, *Nature Reviews—Drug Discovery*, October 2004, 831-844; and references cited in the aforementioned publications).

Use of PDEIV inhibitors in allergic rhinitis is described in B. M. Schmidt et al., *J. Allergy & Clinical Immunology,* 108(4), 2001, 530-536).

Use of PDEIV inhibitors in rheumatoid arthritis and multiple sclerosis is described in H. J. Dyke et al., *Expert Opinion on Investigational Drugs, January* 2002, 11(1), 1-13; C. Burnouf et al., *Current Pharmaceutical Design,* 2002, 8(14), 1255-1296; and A. M. Doherty, *Current Opinion Chem. Biol.,* 1999, 3(4), 466-473; and references cited in these publications.

Use of PDEIV inhibitors in treatment of pain is described in A. Kumar et al., *Indian J. Exp. Biol.,* 2000, 38(1), 26-30).

Use of PDEIV inhibitors in treatment of cognitive impairment (e.g. cognitive impairment in a neurological disorder such as Alzheimer's disease) is described in H. T. Zhang et al. in: *Psychopharmacology, June* 2000, 150(3), 311-316; *Neuropsychopharmacology,* 2000, 23(2), 198-204; and T. Egawa et al., *Japanese J. Pharmacol.,* 1997, 75(3), 275-81.

Use of PDEIV inhibitors as an antidepressant is described in J. Zhu et al., *CNS Drug Reviews,* 2001, 7(4), 387-398; O'Donnell, *Expert Opinion on Investigational Drugs.* 2000, 9(3), 621-625; H. T. Zhang et al., *Neuropsychopharmacology*, October 2002, 27(4), 587-595; J. M. O'Donnell and H.-T. Zhang, *Trends Pharmacol. Sci*., March 2004, 25(3), 158-163; and T. E. Renau, *Curr. Opinion Invest. Drugs.* 2004, 5(1), 34-39).

Use of PDEIV inhibitors in treatment of inflammatory bowel disease (e.g. ulcerative colitis and/or Crohn's disease) has been described in K. H. Banner and M. A. Trevethick, *Trends Pharmacol. Sci*., August 2004, 25(8), 430-436.

In some embodiments, the phosphodiesterase IV (PDEIV)-mediated disease or condition is an inflammatory disease or condition. Such diseases and conditions include inflammatory diseases and disorders, as well as diseases and disorders having an inflammatory component. Such conditions are known to those of skill in the art, and include rheumatoid arthritis, Crohn's disease, inflammatory bowel disease (IBD), colitis, cachexia, Adult Respiratory Distress Syndrome, asthma, hyperoxic alveolar injury, allergic rhinitis, chronic pulmonary inflammatory disease including COPD, depression, psoriatic arthropathies such as psoriatic arthritis, systemic lupus erythrematosus, arthritis and related arthritic conditions (e.g., osteoarthritis and rheumatoid arthritis), rheumatoid spondylitis, inflammation associated with infection (e.g., HIV, hepatitis, etc.), cystic fibrosis, sepsis and sepsis syndrome, endotoxemia, septic shock, toxic shock, endotoxic shock, and hemodynamic shock, post ischemic reperfusion injury, meningitis, fibrotic disease, graft rejection, osteoporosis, multiple sclerosis, ENL in leprosy, radiation damage, bone resorption diseases, periodontitis, psoriasis, atopic dermatitis, contact dermatitis, Behçet's Syndrome, lupus, alopecia, frontal fibrosing alopecia, vitiligo, acne, lichen planus, uveitis, Prurigo nodularis, and discoid lupus erythematosus.

In some embodiments, the PDEIV-mediated disease or condition is an inflammatory skin disease or condition.

In some embodiments, the inflammatory skin disease is psoriasis, plaque psoriasis, atopic dermatitis, contact dermatitis, seborrheic dermatitis, stasis dermatitis, morphea, Behçet's Syndrome, lupus, alopecia, frontal fibrosing alopecia, vitiligo, acne, lichen planus, uveitis, Prurigo nodularis, or discoid lupus erythematosus.

In some embodiments, the inflammatory skin disease is psoriasis.

In some embodiments, the inflammatory skin disease is plaque psoriasis.

In other embodiments, the inflammatory skin disease is atopic dermatitis.

In other embodiments, the inflammatory skin disease is contact dermatitis.

In other embodiments, the inflammatory skin disease is seborrheic dermatitis.

In other embodiments, the inflammatory skin disease is stasis dermatitis.

In other embodiments, the inflammatory skin disease is morphea.

In some embodiments, the inflammatory disease or condition is psoriatic arthritis, plaque psoriasis, atopic dermatitis, or COPD.

In some aspects, the phosphodiesterase IV (PDEIV)-mediated disease or condition is an immune disorder.

In some embodiments, the immune disorder is a chronic inflammatory disorder, asthma, rheumatoid arthritis, or Behçet's syndrome.

In some aspects, the phosphodiesterase IV (PDEIV)-mediated disease or condition is a disease mediated by cytokines.

In some embodiments, the disease mediated by cytokines is periodontitis, dry eye disease, rheumatoid arthritis, osteoarthritis, Crohn's disease, ulcerative colitis, psoriatic arthritis, traumatic arthritis, rubella arthritis, inflammatory bowel disease, multiple sclerosis, psoriasis, graft versus host disease, systemic lupus erythematosus, toxic shock syndrome, irritable bowel syndrome, muscle degeneration, allograft rejections, pancreatitis, insulitis, glomerulonephritis, diabetic nephropathy, renal fibrosis, chronic renal failure, gout, leprosy, acute synovitis, Reiter's syndrome, gouty arthritis, Behcet's disease, spondylitis, endometriosis, non-articular inflammatory conditions, such as intervertebral disk syndrome conditions, bursitis, tendonitis, tenosynovitis or fibromyalgic syndrome, acute or chronic pain, including but not limited to neurological pain, neuropathies, polyneuropathies, diabetes-related polyneuropathies, trauma, migraine, tension and cluster headache, Horton's disease, varicose ulcers, neuralgias, musculo-skeletal pain, osteo-traumatic pain, fractures, algodystrophy, spondyloarthritis, fibromyalgia, phantom limb pain, back pain, vertebral pain, post-surgery pain, herniated intervertebral disc-induced sciatica, cancer-related pain, vascular pain, visceral pain, childbirth, HIV-related pain, allergy, metabolic disease, a chemotherapy/radiation related complication, diabetes type I, diabetes type II, a liver disease, a gastrointestinal disorder, an ophthamological disease, allergic conjunctivitis, diabetic retinopathy, Sjogren's syndrome, uvetitis, a pulmonary disorder, a renal disease, dermatitis, HIV-related cachexia, cerebral malaria, ankylosing spondolytis, leprosy, anemia, fibromyalgia, kidney failure, stroke, chronic heart failure, endotoxemia, reperfusion injury, ischemia reperfusion, myocardial ischemia, restenosis, thrombosis, angiogenesis, Coronary Heart Disease, Coronary Artery Disease, acute coronary syndrome, Takayasu arteritis, cardiac failure such as heart failure, aortic valve stenosis, cardiomyopathy, myocarditis, vasculitis, vascular restenosis, valvular disease, coronary artery bypass, hypercholesterolemia, diseases or conditions related to blood coagulation or fibrinolysis, such as for example, acute venous thrombosis, pulmonary embolism, thrombosis during pregnancy, hemorrhagic skin necrosis, acute or chronic disseminated intravascular coagulation (DIC), clot formation from surgery, long bed rest or long periods of immobilization, venous thrombosis, fulminant meningococcemia, acute thrombotic strokes, acute coronary occlusion, acute peripheral arterial occlusion, massive pulmonary embolism, axillary vein thrombosis, massive iliofemoral vein thrombosis, occluded arterial or venous cannulae, cardiomyopathy, venoocclusive disease of the liver, hypotension, decreased cardiac output, decreased vascular resistance, pulmonary hypertension, diminished lung compliance, leukopenia or thrombocytopenia; atherosclerosis, uveitis, glaucoma, optic neuritis, retinal ischemia, diabetic retinopathy, laser induced optic damage, or surgery or trauma-induced proliferative vitreoretinopathy, allergic rhinitis, asthma, adult respiratory distress syndrome, chronic pulmonary inflammation, chronic obstructive pulmonary disease, emphysema, bronchitis, mucus hypersecretion, silicosis, SARS infection and respiratory tract inflammation, psoriasis, eczema, atopic dermatitis, contact dermatitis, acne, Guillain-Barre syndrome, Parkinson's disease, Huntington's disease, Alzheimer's disease, amyotrophic lateral sclerosis, multiple sclerosis and other demyelinating diseases, viral and bacterial meningitis, CNS trauma, spinal cord injury, seizures, convulsions, olivopontocerebellar atrophy, AIDS dementia complex, MERRF and MELAS syndromes, Leber's disease, Wemicke's encephalopathy, Rett syndrome, homocystinuria, hyperprolinemia, hyperhomocysteinemia, nonketotic hyperglycinemia, hydroxybutyric aminoaciduria, sulfite oxidase deficiency, combined systems disease, lead encephalopathy, Tourette's syndrome, hepatic encephalopathy, drug addiction, drug tolerance, drug dependency, depression, anxiety and schizophrenia, aneurism, epilepsy, bone resorption diseases, osteopetrosis, osteoporosis, or osteoarthritis, diabetes, systemic cachexia, cachexia secondary to infection or malignancy, cachexia secondary to acquired immune deficiency syndrome (AIDS), obesity, anorexia or bulimia nervosa, sepsis, HIV, HCV, malaria, infectious arthritis, leishmaniasis, Lyme disease, cancer, including but not limited to breast cancer, colon cancer, lung cancer, prostate cancer, multiple myeloma, acute myelogenous leukemia, myelodysplastic syndrome, non-Hodgkins lymphoma, follicular lymphoma, Castleman's disease, or drug resistance.

In some embodiments, the phosphodiesterase IV (PDEIV)-mediated disease or condition is allergic conjunctivitis.

In some embodiments, the disclosure is directed to methods of treatment of a patient with allergic conjunctivitis comprising administering to the patient an amount of a compound of Formula (I) or a pharmaceutically acceptable salt thereof effective to treat allergic conjunctivitis.

In some embodiments, the amount of a compound of Formula (I) or a pharmaceutically acceptable salt thereof is effective to reduce a sign or symptom of allergic conjunctivitis.

In some embodiments, the sign or symptom of allergic conjunctivitis is ocular itching, conjunctivital redness, ciliary redness, episcleral redness, chemosis, eyelid swelling, tearing, rhinorrhea, nasal pruritus, ear or palate pruritus, or nasal congestion. In other embodiments, the sign or symptom of allergic conjunctivitis is ocular itching. In yet other embodiments, the sign or symptom of allergic conjunctivitis is conjunctivital redness.

A person of ordinary skill in the art would understand how to devise methods for determining whether a reduction (i.e., an improvement) in a sign or symptom of allergic conjunctivitis has occurred. Indeed, such methods are known to those of skill in the art, and include for example, objective methods and subjective measures. The signs of allergic conjunctivitis, as well as their severity, can be assessed by ophthalmologic examination, and may include the use of instruments such as the slit-lamp microscope. Patient self-assessment scales, such as visual analog scales, numerical scales, and severity indexes, may be used for subjective assessments of symptoms and their severity. See. e.g., A. Leonardi, *Diagnostic tools in ocular allergy*, Allergy. 2017; 72:1485-1498.

In some embodiments, the reduction in a sign or symptom of allergic conjunctivitis is measured using a numerical scale ranging from no sign or symptom at one extreme to severe sign or symptom at the other extreme. For example, a numerical scale to assess ocular itching may range from 0 to 5, or 0 to 10, or 0 to 20, with 0 representing no itching, and the highest number representing severe itching. Similar scales can be employed to measure objective signs of allergy, such as conjunctival redness.

In some aspects, the phosphodiesterase IV (PDEIV)-mediated disease or condition is a neutrophil-mediated disease.

In some embodiments, the neutorphil-mediated disease is bronchial asthma, rhinitis, influenza, stroke, myocardial infarction, thermal injury, adult respiratory distress syndrome (ARDS), multiple organ injury secondary to trauma, acute glomerulonephritis, dermatoses with acute inflammatory components, acute purulent meningitis, hemodialysis, leukopheresis, granulocyte transfusion associated syndromes, or necrotizing enterocolitis.

In some aspects, the phosphodiesterase IV (PDEIV)-mediated disease or condition is a neurodegenerative disorder.

In some embodiments, the neurodegenerative disorder is Alzheimer's disease, Parkinson disease, an inflammatory bowel disease selected from the group consisting of: Crohn's disease and ulcerative colitis, diarrhea a liver disease selected from the group consisting of: an autoimmune hepatitis, hepatitis C, primary biliary cirrhosis, primary sclerosing cholangitis, or fulminant liver failure, a gastrointestinal disorder selected from the group consisting of: celiac disease and non-specific colitis, a bone disease such as osteoporosis, a pulmonary disorder selected from the group consisting of: allergic rhinitis, asthma, chronic obstructive pulmonary disease, chronic granulomatous inflammation, cystic fibrosis, and sarcoidosis, a cardiovascular disease selected from the group consisting of: atheroscleotic cardiac disease, congestive heart failure, and restenosis, and a renal disease is selected from the group consisting of: glomerulonephritis and vasculitis.

In some aspects, the phosphodiesterase IV (PDEIV)-mediated disease or condition is acute and chronic (in particular inflammatory and allergen-induced) airway disorders of varying origin (bronchitis, allergic bronchitis, bronchial asthma); dermatoses (especially of proliferative, inflammatory and allergic type), such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous ache, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS), types of shock [septic shock, endotoxin shock, gram-negative sepsis, toxic shock syndrome and adult respiratory distress syndrome (ARDS) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as colics of the kidneys and of the ureters in connection with kidney stones.

The methods of the invention comprise administering a compound of Formula (I), or a pharmaceutically acceptable salt thereof. The compound of Formula (I), $N^2$-methyl-$N^4$-phenyl-6-(2,2,3,3-tetrafluoropropoxy)-1,3,5-triazine-2,4-diamine, has been described in, for example, WO2017112951. See also. S. Lee, et al., *J. Med. Chem.* 2017; 60, 3, 1210-1218.

In some embodiments of the methods of the invention, a compound of Formula (I) is administered.

In other embodiments of the methods of the invention, a pharmaceutically acceptable salt of the compound of Formula (I) is administered. The term "pharmaceutically acceptable salt" refers to acid addition salts of the compound of Formula (I) that are prepared with relatively nontoxic acids. Acid addition salts can be obtained by contacting the neutral form of the compound of Formula (I) in a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Thus, the compound of Formula (I) may exist as salt including the hydrochloride, hydrobromide, sulfate, methanesulfonate, nitrate, maleate, acetate, citrate, fumarate, tartrate (e.g., (+)-tartrate, (−)-tartrate, or mixtures thereof including racemic mixtures), succinate, benzoate, and salts with amino acids such as glutamic acid. These salts may be prepared by methods known to those skilled in the art.

In some embodiments, the compound of Formula (I) may also contain unnatural proportions of atomic isotopes at one or more of the atoms that constitute such compounds. For example, the compound of Formula (I) may be radiolabeled with isotopes, such as for example, deuterium ($^2H$), tritium ($^3H$), fluoride ($^{18}F$), iodine-125 ($^{125}I$), or carbon-14 ($^{14}C$). All isotopic variations of the compound of Formula (I), whether radioactive or not, are encompassed within the scope of the present invention.

In the methods of the disclosure, the amount of the compound of Formula (I) or a pharmaceutically acceptable salt thereof is effective to treat the PDEIV-mediated disease or condition.

As used herein, the phrase "an amount effective to treat" refers to an amount sufficient to accomplish a stated purpose (e.g. achieve the effect for which it is administered, treat a disease, reduce one or more symptoms of a disease or condition). An example of an "an amount effective to treat" is an amount sufficient to contribute to the treatment, prevention, or reduction of a sign(s) or symptom(s) of a disease or condition. A "reduction" of a sign(s) or symptom(s) (and grammatical equivalents of this phrase) means decreasing of the severity or frequency of the sign(s) or symptom(s), or elimination of the sign(s) or symptom(s). Such a reduction in a sign or symptom can be determined using a numerical scale for signs and/or symptoms as outlined above.

In some embodiments, an "amount . . . effective to treat" is an amount that has a prophylactic effect, e.g., preventing or delaying the onset (or reoccurrence) of a disease or condition, or reducing the likelihood of the onset (or reoccurrence) of a disease or condition, or the symptoms thereof.

Administration of an "amount effective to treat" may comprise administering the amount in a single dose, or in multiple doses. The exact amounts depend on the purpose of the treatment, and are ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The "amount effective to treat" may be estimated from assays and animal models, such as those disclosed herein. Such information can be used by those of skill in the art to determine useful doses in humans.

For systemic administration, dosage amount and interval can be adjusted individually to provide suitable plasma levels of the active moiety. In some embodiments, dosages for systemic administration range from about 0.1 mg/day to about 1000 mg/day, for example, 1-500 mg/day, 10-200 mg/day, or 100-200 mg/day.

In embodiments in which the compound of Formula (I) is administered topically, the "amount . . . effective to treat" can range from about 0.01 $mg/cm^2$ to about 10 $mg/cm^2$, for example, from about 0.1 $mg/cm^2$ to about 10 $mg/cm^2$, or from about 0.1 $mg/cm^2$ to about 2 $mg/cm^2$.

The dosage and frequency (single or multiple doses) administered to a mammal can vary depending upon a variety of factors, including for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Adjustment and manipulation of established dosages (e.g., frequency and duration) are well within the ability of those skilled in the art.

In some aspects, the disclosure is directed to methods of inhibiting release of an inflammatory cytokine from mammalian inflammatory cells by contacting the mammalian inflammatory cells with an amount of a compound of Formula (I), or a pharmaceutically acceptable salt thereof, effective to inhibit the release of an inflammatory cytokine from mammalian inflammatory cells.

In some embodiments of these methods, the inflammatory cytokine is tumor necrosis factor alpha (TNFa); interleukins (ILs), including IL-1, IL-2, IL-3, IL-4, IL-5, IL-6, IL-7, IL-8, IL-9, IL-10, IL-11, and IL-12; interferons, including alpha-interferon, beta-interferon, or gamma-interferon.

As used herein, the term "inhibiting release" means preventing or reducing the amount of inflammatory cytokine released by inflammatory cells relative to the amount that would be released by the cells in the absence of the compound of Formula (I). Methods of measuring cytokine levels are known to those of skill in the art.

As used herein, the term "contacting" refers to bringing the compound of Formula (I) into proximity with the mammalian inflammatory cells such that they are able to make physical contact.

In some aspects, the disclosure is directed to methods of inhibiting PDE IV activity in mammalian inflammatory cells, said method comprising contacting the mammalian inflammatory cells with an amount of a compound of Formula (I), or a pharmaceutically acceptable salt thereof, effective to inhibit said PDE IV activity.

As used herein, the term "inhibiting PDE IV activity" means preventing or reducing the enzymatic activity of the PDE IV enzyme relative to the activity of the PDE IV enzyme in the absence of the compound of Formula (I). Methods of measuring PDE IV activity are known to those of skill in the art.

In the methods of the disclosure, the compound of Formula (I) or pharmaceutically acceptable salt thereof can be administered in a pharmaceutical composition comprising the compound of Formula (I), or a pharmaceutically acceptable salt thereof, and a pharmaceutically acceptable excipient.

"Pharmaceutically acceptable excipient" refers to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

Pharmaceutical compositions suitable for use in the methods of the present invention include any dosage form suitable for administration to the patient. Such dosage forms include, without limitation, tablets, powders, capsules, pills, cachets, lozenges, applicator sticks, solutions, suspensions, emulsions, gels, creams, ointments, pastes, jellies, paints, powders, aerosols, dragees, liquids, syrups, slurries, suspensions, suppositories, microspheres, liposomes, and dispersible granules.

As used herein, the term "administering" means applying the compound of Formula (I) or a pharmaceutically acceptable salt thereof (including as a pharmaceutical composition) to the patient's body in a manner that results in the presence of the compound of Formula (I) at the site of inflammation. Administration includes oral administration, administration as a suppository, topical contact, transdermal, intravenous, parenteral, intraperitoneal, intramuscular, intralesional, intrathecal, intranasal or subcutaneous administration, the implantation of a slow-release device, e.g., a mini-osmotic pump, to a subject, transmucosal (e.g., buccal, sublingual, palatal, gingival, nasal, vaginal, rectal, or transdermal), parenteral (e.g., intravenous, intramuscular, intra-arteriole, intradermal, subcutaneous, intraperitoneal, intraventricular, and intracranial). Other modes of delivery include, but are not limited to, the use of liposomal formulations, intravenous infusion, transdermal patches, and the like.

In some embodiments of the disclosed methods, the compound of Formula (I), or a pharmaceutically acceptable salt thereof, is administered topically, orally, perorally, as a suppository, intravenously, parenterally, intraperitoneally, intramuscularly, intralesionally, intrathecally, intranasally, or subcutaneously.

In other embodiments of the disclosed methods, the compound of Formula (I), or a pharmaceutically acceptable salt thereof, is administered topically.

In some embodiments of the disclosed methods, the compound of Formula (I), or a pharmaceutically acceptable salt thereof, is administered orally.

In the methods of the disclosure, the compound of Formula (I) or pharmaceutically acceptable salt thereof can be administered in combination with other active drugs known to be useful in treating a given disease or condition, or in combination with adjunctive agents that may not be effective alone, but may contribute to the efficacy of the compound of Formula (I). In such embodiments, a compound of Formula (I) is administered at the same time as, prior to, or after the administration of one or more additional agents.

The following examples further illustrate aspects of the methods of the disclosure, and are not intended to be limiting.

EXAMPLES

Example 1

Animals

Animals are housed individually in IVC cages and autoclaved corncob is used as the bedding material. Animals are maintained in a controlled environment with 22±3° C. temperature, 50±20% humidity, a light/dark cycle of 12 hours each and 15-20 fresh air changes per hour. The animals are fed ad libitum. with certified Irradiated Laboratory Rodent Diet (Nutrilab brand, Tetragon Chemie Pvt. Ltd., Bangalore).

Animal Acclimatization

Animals are kept under acclimatization for a period of about 5-7 days before initiation of the study. On the day of the study, animals are randomized based on bodyweight.

Randomization

Animals are randomized based on bodyweight such that there is less than 10% intergroup variation. Immediately after randomization, the animals are assigned a permanent number by ear notching. Cages are identified by cage cards indicating the study code, group number, sex, dose, cage number, number of animals and animal number details.

| Test System | |
|---|---|
| Species/Strain | BALB/c |
| Sex | Male |
| Age at the start of experiment | 7-8 weeks |
| Body weight range | ~19-23 g |
| Source | Taconic or other vendor |
| Total number of animals | 67 |
| Temperature | 23 ± 2° c. |
| Humidity | 60 ± 20% |
| Food | ad libitum |
| Water | ad libitum |
| Light cycle | Normal 7AM-7PM light cycle |

Test Item Details

1. Dexamethasone Cat. or Batch no.: BCBM4557V (sigma)
   Vehicle for dexamethasone (Veh.1): acetone:ethanol (1:1), 20 μL/ear
   Dose: 0.1 mg/ear
   Dose volume: 20 μL/ear
2. Crisaborole: PZ0037 (Sigma)
   Vehicle (Veh.1): acetone:ethanol (1:1), 20 μL/ear
   Dose: 0.1 mg/ear
   Dose volume: 20 μL/ear
3. Compound of Formula (I)
   Vehicle (Veh.1): acetone:ethanol (1:1), 20 μL/ear
   Dose: 0.1 mg/ear
   Dose volume: 20 μL/ear Study Groups Dexamethasone and Test Item Preparation and Application:

Strength of working solution=5 mg/ml

On day 0, Group 1 are topically applied with vehicle alone (Ethanol: Acetone=1:1).

Animals in group 2, 3, and 4 receive dexamethasone, Crisaborole and the compound of Formula (I), respectively (as a solution in acetone and ethanol by 1:1 ratio), 30 min before PMA challenge, on both ears.

Study Procedure

Timeline:

−24 hr—Randomization (body weight based)
−30 min—Treatment Topical
0 min—Disease Induction PMA application
15 min—Treatment Topical
6 hr—Skin Thickness, Skin Collection (Cohort 1)
24 hr—Skin Thickness, Skin Collection (Cohort 2)

| Group | Group Title | Challenge (right and left Ear) | Treatment Regimen | N^ |
|---|---|---|---|---|
| 1 | PMA control | PMA-5 μg/20 μL on right and left ear | Acetone:ethanol (1:1)-Topical 20 μl right and left ear, 30 min before PMA and 15 min after PMA challenge | 8 + 8 |
| 2 | Dexamethasone (0.5% w/v) | PMA-5 μg/20 μL on right and left ear | Dexamethasone-Topical 0.1 mg/right and left ear, 30 min before PMA challenge and 15 min after PMS challenge | 8 + 8 |
| 3 | Crisaborole (0.5% w/v) | PMA-5 μg/20 μL on right and left ear | Crisaborole-Topical 0.1 mg/right and left ear, 30 min before PMA and 15 min after PMA challenge | 8 + 8 |
| 4 | The compound of Formula (I) (0.5% w/v) | PMA-5 μg/20 μL on right and left ear | The compound of Formula (I)-Topical 0.2 mg/right and left ear, 30 min before PMA and 15 min after PMA challenge | 8 + 8 |
| 5 | Sham | Acetone-20 μL on right and left ear | Acetone:ethanol (1:1)-Topical 20 μl right and left ear, 30 min before acetone and 15 min after acetone challenge | 3 |

Disease Induction:

5 μg/20 μl/right ear and 5 μg/20 μl/left ear (2.5 μg/10 μl in anterior and posterior surface of both ears)

Phorbol 12-myristate 13-acetate (PMA) is formulated in acetone at a concentration of 250 μg/ml. This working solution is applied topically to the anterior and posterior surface of both the ear (10 μl each side).

Observations:

Ear thickness (both right and left ear): at −1 hr (before PMA challenge), 6 hr and 24 hrs post PMA challenge.

Ear Collection:

At 6 hr and 24 hrs, respective cohort of animals are euthanized, and ear tissues are collected. Right ears are collected, flash frozen in liquid nitrogen, and stored at −80° C. until homogenization for cytokine estimation (3 sham control animals are used for comparison). Left ears are collected and preserved in 10% NBF for Histopathology. Half of the left ear is used for drug concentration measurement, and the other half of the left ear is used for Histopathology.

Blood Collection:

Blood is collected by retro-orbital bleeding into K2-EDTA tubes just before the euthanasia; plasma is separated and stored at −80° C. for further analysis (for test item concentration).

Results:

As shown in FIGS. 4, 5, 8, 9, 12, and 13, the compound of Formula (I) prevents or reduces PMA-induced ear thickening and ear weight gain (i.e., indicia of hyperplasia) at 6 hours to an extent comparable to dexamethasone and crisaborole.

Example 2

Housing and Feeding of Animals:

Animals are housed individually in IVC cages and autoclaved corncob is used as the bedding material. Animals are maintained in a controlled environment with 22±3° C. temperature, 50t 20% humidity, a light/dark cycle of 12 hours each and 15-20 fresh air changes per hour. The animals are fed ad libitum. with certified Irradiated Laboratory Rodent Diet (Nutrilab brand, Tetragon Chemie Pvt. Ltd., Bangalore).

Animal Acclimatization:

On receipt, the animals are assigned a temporary number at the base of tail using an indelible marker pen. All the animals are kept under acclimatization for a period of about 5-7 days before initiation of the study. On the day of the study, animals are randomized based on bodyweight.

Randomization:

Animals are randomized based on bodyweight such that there is less than 10% intergroup variation. Immediately after randomization, the animals are assigned a permanent number by ear notching. Cages are identified by cage cards indicating the study code, group number, sex, dose, cage number, number of animals and animal number details.

| Test System | |
|---|---|
| Species/Strain | BALB/c |
| Sex | Male |
| Age at the start of experiment | 7-8 weeks |
| Body weight range | 20-24 g |
| Source | Hylasco |
| Total number of animals | 31 |
| Temperature | 22 ± 3° C. |
| Humidity | 50 ± 20% |
| Food | ad libitum |
| Water | ad libitum |
| Light cycle | Normal 7AM-7PM light cycle |

Test Item Details

1. Dexamethasone Cat. or Batch no.: BCBM4557V (sigma)
   Vehicle for dexamethasone (Veh.1): acetone:ethanol (1:1)
   Dose: 0.1 mg/ear & 0.25 mg in back skin
   Dose volume: 20 μL/ear & 50 μL on back skin
2. Crisaborole: PZ0037 (Sigma)
   Vehicle (Veh.1): acetone:ethanol (1:1)
   Dose: 0.1 mg/ear & 0.25 mg in back skin
   Dose volume: 20 μL/ear, 50 μL on back skin
3. Compound of Formula (I)
   Vehicle (Veh.1): acetone:ethanol (1:1)
   Dose: 0.1 mg/ear & 0.25 mg in back skin
   Dose volume: 20 μL/ear, 50 μL on back skin Dexamethasone and Test Item Preparation and Application:

Strength=5 mg/ml

Application=100 μg/20 pit per each ear+250 μg/50 μL on the back G2 to G4 receive Dexamethasone, Crisaborole or test item: Daily topical treatment (D0-D6): 0.1 mg in 20 μl per ear x both the ears+0.25 mg in 50 μl (on the back) 6-8 hrs after IMQ application.

Study Procedure

Timeline:

Disease Induction: Application of 5% IMQ cream 40 mg (back) and 5 mg (per ear—Inner surface) daily from day 0-6.

Treatment: 0.5% Dexamethasone solution: 0.25 mg (back) and 0.1 mg (per ear) 8 hrs post IMQ.

Day −2—Depilation on back region

Day 0—Observations (Body weight; ear thickness using digital microcaliper)

Day 2—Observations (Body weight; ear thickness using digital microcaliper)

Day 4—Observations (Body weight; ear thickness using digital microcaliper)

Day 6—Observations (Body weight; ear thickness using digital microcaliper); Blood collection (PK) and Termination {2 hrs after last dose) • Ear collection: PK, Cytokine, MPO, Thickness • Back skin collection, scoring and thickness measurement • Histopathology (optional)

Study Groups

| Group | Group Title | Induction | Treatment Daily Dose L ear + R ear + back | Treatment Route | No. of mice |
|---|---|---|---|---|---|
| 1 | IMQ control (Acetone + ethanol vehicle) | IMQ (Ear and Back) | | Topical | 7 |
| 2 | Dexamethasone (0.5% w/v) | IMQ (Ear and Back) | 0.1 mg + 0.1 mg + 0.25 mg | Topical | 7 |
| 3 | Crisaborole (0.5% w/v) | IMQ (Ear and Back) | 0.1 mg + 0.1 mg + 0.25 mg | Topical | 7 |
| 4 | The compound of Formula (I) (0.5% w/v) | IMQ (Ear and Back) | 0.1 mg + 0.1 mg + 0.25 mg | Topical | 7 |
| 5 | Sham | vaseline | | Topical | 3 |

Animals in group 2-4: As mentioned table above.

Animals in group 1: receive acetone and ethanol vehicle (1:1) topically, once daily.

Diseases Induction:

Disease Induction: Imiquimod 5% Cream

The dorsal posterior area (2 cm×2 cm) of animals is depilated using a hair trimmer. 5% Imiquimod cream: 50 mg/animal (40 mg on the shaved back+5 mg each on the inner part of right and left ear) QD is applied on days 0 to 5 (Groups 1-4).

Vaseline: 50 mg/animal (40 mg on the shaved back+5 mg each on the inner part of right and left ear is applied QD on days 0 to 5 to sham control mice. They do not receive any additional treatment (Group 5).

Observation:

The body weight is recorded individually for all animals at receipt, day of randomization, prior to treatment, and once in two days thereafter. The animals are observed for mortality at regular intervals.

Blood Collection:

On day 6, blood is collected by retro-orbital bleeding under isoflurane anesthesia prior to euthanasia. Blood is collected in K2-EDTA tubes and plasma is separated and stored at −80° C. for further analysis (for test item concentration).

Ear Collection:

2 hrs post compound treatment on day 6, all the animals are euthanized, and ear tissues are collected. The right ear is flash frozen in liquid nitrogen and stored at −80° C. until homogenization for MPO and cytokine estimation.

The half of the left ear is used for drug concentration measurement. The other half of the left ear tissue is used for histopathology. The back skin is collected for visual assessment (scoring) and histopathology.

MPO analysis: Snap frozen ear tissue samples are homogenized in 1× assay buffer provided in the kit. The homogenates are centrifuged at 8000 g for 10 minutes in a refrigerated centrifuge. The supernatants are discarded, and the pellet is resuspended in solubilisation buffer (1× assay buffer containing 0.5% HTABr). The samples are homogenized and subjected to three rounds of freeze thaw followed by brief sonication for 10s. The samples are centrifuged at 12,000 g for 10 minutes in a refrigerated centrifuge and the resulting supernatants are analysed for MPO levels based on a fluorometric detection kit. The Kit utilizes a non-fluorescent detection reagent, which is oxidized in the presence of hydrogen peroxide and MPO to produce its fluorescent analogue. (Enzo Life Sciences; ADI-907-029).

Histopathology: At study termination, posterior dorsal skin and ear skin samples are collected. Skin samples are processed using routine histopathological methods and 4-5 μm paraffin sections are prepared. Tissue sections (3 serial sections/animal) are stained with Hematoxylin and eosin (H&E) to evaluate acanthosis, hyper/parakeratosis and inflammatory cellular infiltration in dermis. Severity of lesions are assessed semi quantitatively on a scale of 0-4 by two independent pathologists (0—normal, 1—mild degree, 2—moderate degree, 3—severe degree and 4—extensive or multiple locations) for each parameter in a blinded manner. The percentage of lesioned area involved are taken into consideration while evaluating the scores. The scores (for each parameter) are averaged per group. Cumulative lesion scores are calculated by adding the scores of Acanthosis, Hyperkeratosis, Parakeratosis & Cellular infiltration (Hence maximum score=16). All treatment groups are compared with pathological control group.

Results:

See van der Fits et al., Imiquimod-Induced Psoriasis-Like Skin Inflammation in Mice Is Mediated via the IL-23/IL-17 Axis. *The Journal of Immunology*. 2009, 182: 5836-5845.

Figure 27:
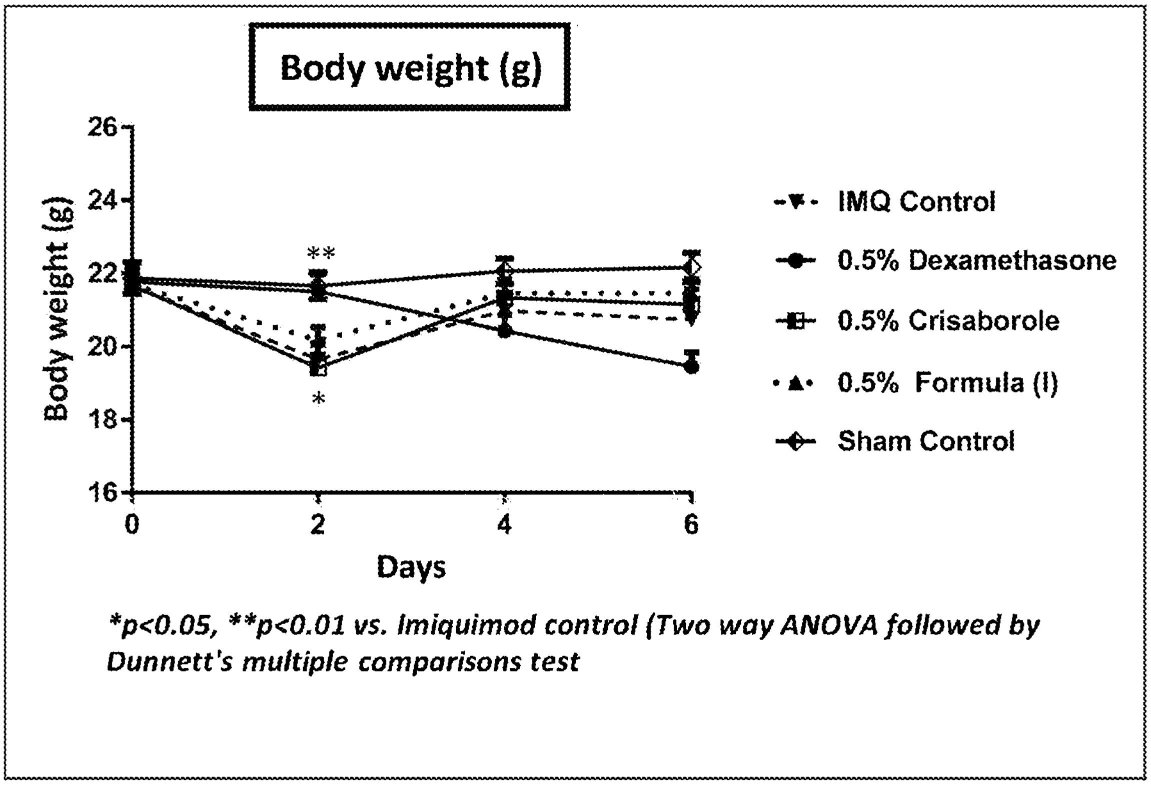
FIG. 27 shows the body weight by group in Example 2.
Figure 28:
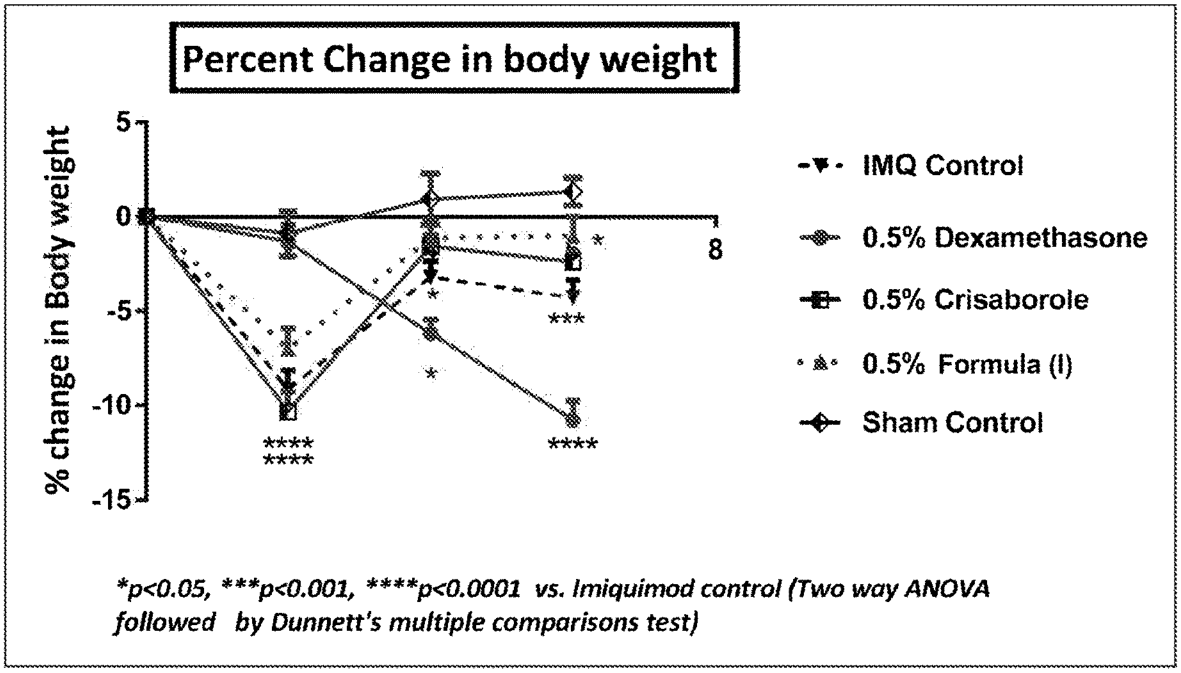
FIG. 28 shows the percent change in body weight by group in Example 2.

Sham control animals show a significant increase in body weight when compared to IMQ control animals. Animals treated with 0.5% Dexamethasone show a significant body weight loss when compared to IMQ control animals. Body weight loss in animals is significantly less with topical treatment of the compound of Formula (I)(0.5%) when compared to IMQ control animals. See FIGS. 27 and 28.

Figure 29:
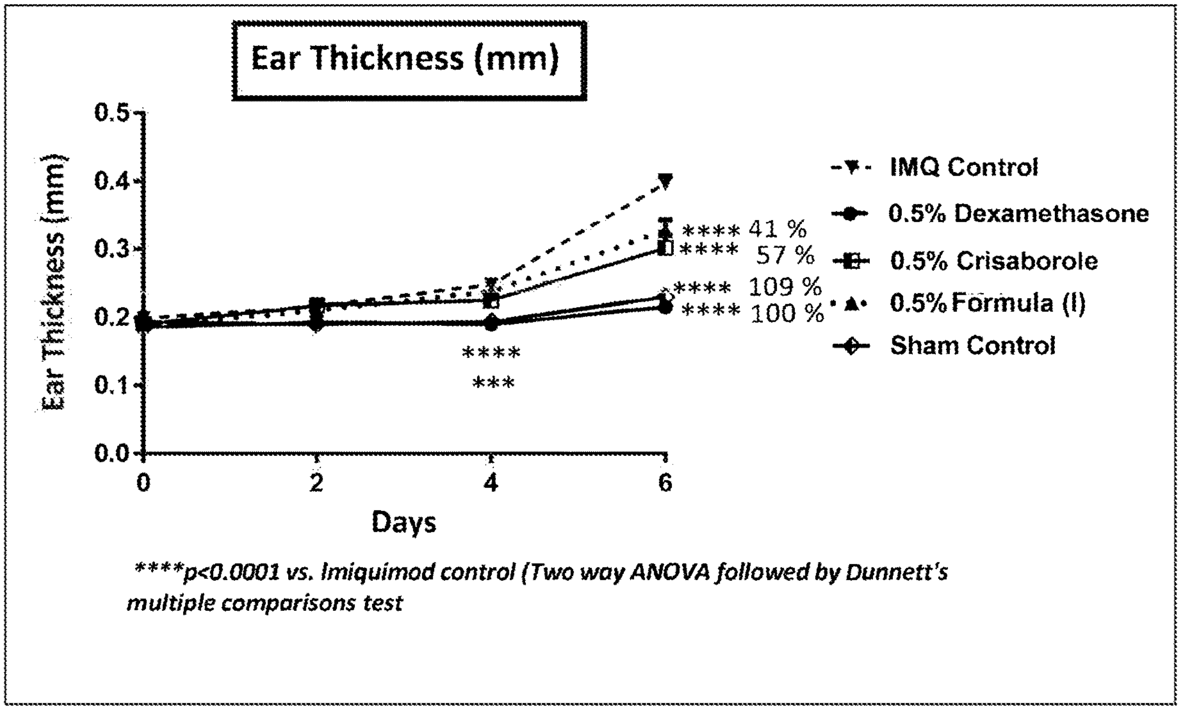
FIG. 29 shows the ear thickness by group in Example 2.

IMQ application increases the ear thickness in the pathological (IMQ control) animals. Dexamethasone (0.5%) application results in a significant reduction in ear thickness ($p<0.001$) on days 4 and 6 respectively. Topical treatment of Crisaborole (0.5%) and the compound of Formula (I)(0.5%) shows significant reduction in ear thickness on day 6. See FIG. 29.

To score the severity of inflammation of the back skin, an objective scoring system is developed. All animals are scored for erythema, scale formation and skin thickness formation independently on a scale of 0 to 4. The cumulative clinical score is calculated by summing up scores of erythema, skin thickness and scales. Hence the maximum score for each animal is 12. The scoring system is based on the clinical Psoriasis Area and Severity Index (PASI) as below: (van der Fits et al.; J Immunol 2009) (0—Normal 1—Mild 2—Moderate 3—Marked 4—Very Marked) 2-3 days after imiquimod application, signs of erythema, skin thickness and scale formation are observed on the back skin of animals. There is significant increase in all the individual scores and the cumulative clinical scores in the IMQ control animals when compared to sham control animals.

IMQ control group shows significant increase in the cumulative clinical scores comprising of erythema, skin thickness and scales. Treatment with dexamethasone shows significant reduction in the extent of erythema, skin thickness and scales and in the overall cumulative clinical scores. Animals treated with Crisaborole (0.5%) show significant reduction in the cumulative clinical scores on day 6 when compared to IMQ control animals ($p<0.05$). Treatment with the compound of Formula (I) does not show any significant reduction in the overall cumulative scores. See FIGS. 31-34.

Figure 35:
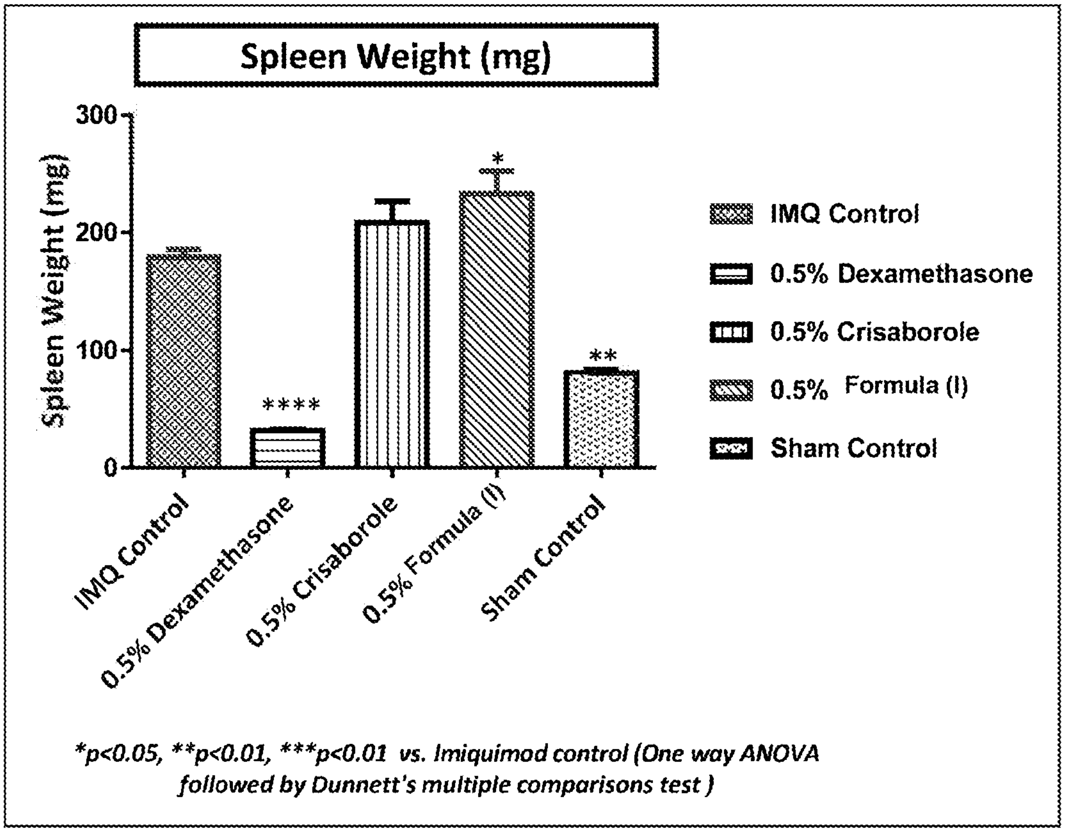
FIG. 35 shows spleen weight by group in Example 2.
Figure 36:
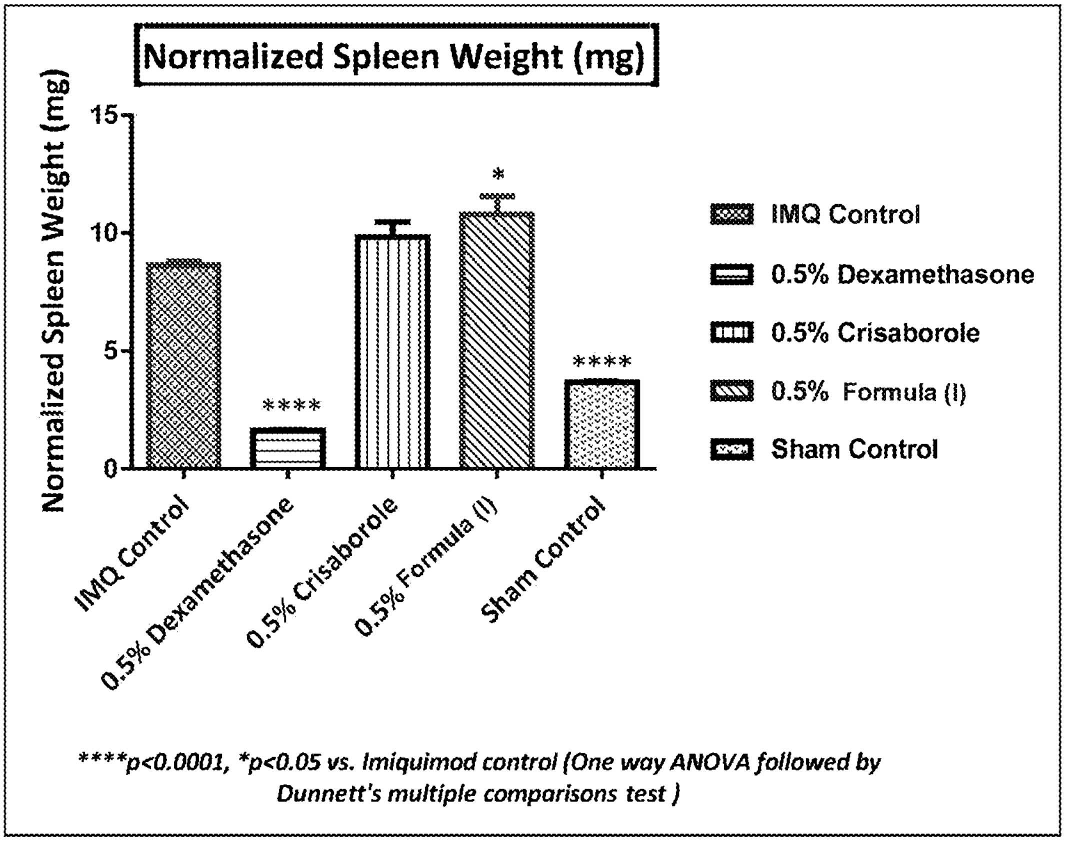
FIG. 36 shows normalized spleen weight by group in Example 2.

Splenomegaly is observed in this model due to differentiation of Th17 cells in the spleen. IMQ control animals show significant increase in spleen weight. Dexamethasone treated animals show significant reduction in spleen weight ($p<0.0001$). Animals treated with Crisaborole and the compound of Formula (I) do not show significant reduction in spleen weight or normalized spleen weight when compared to IMQ control animals. See FIGS. 35 and 36.

Figure 30:
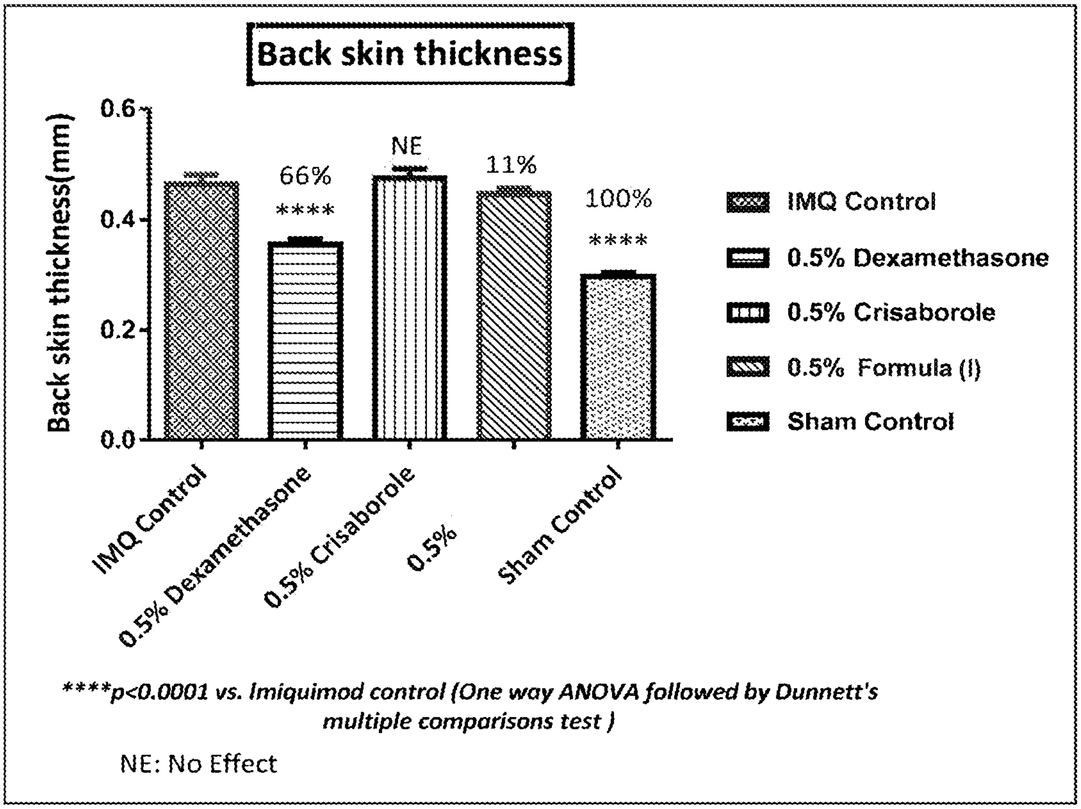
FIG. 30 shows back skin thickness by group in Example 2.
Figure 31:
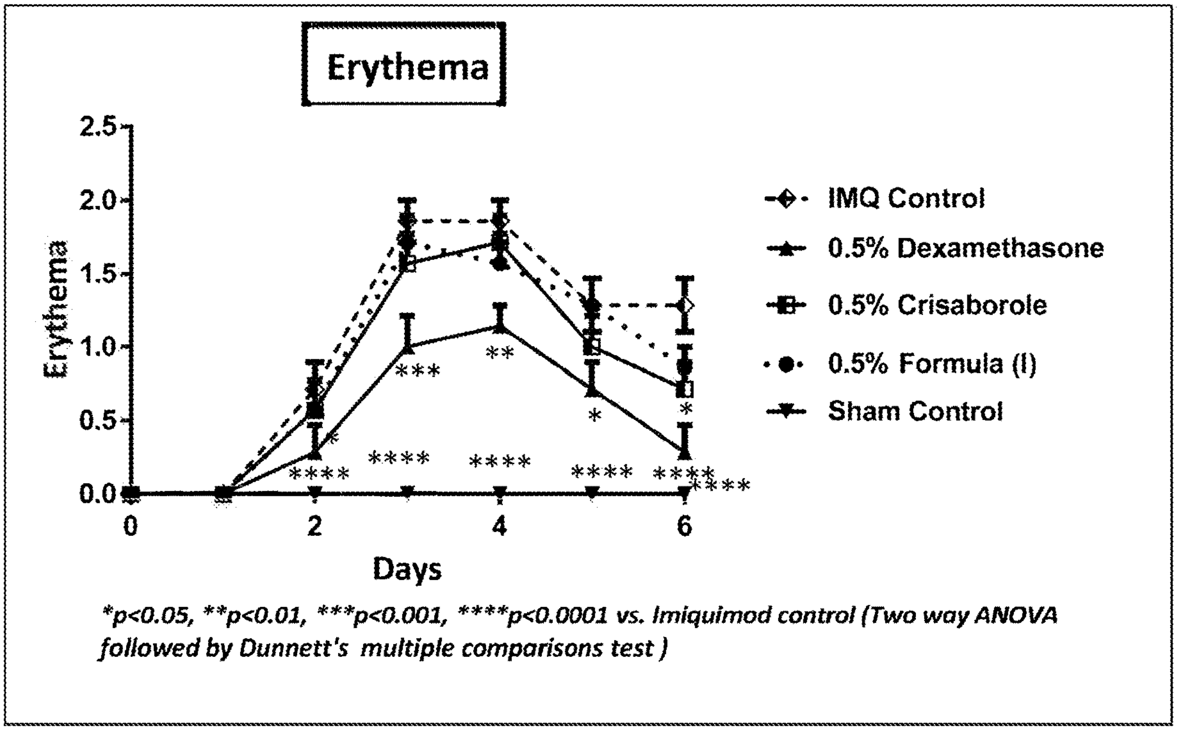
FIG. 31 shows erythema by group in Example 2.
Figure 32:
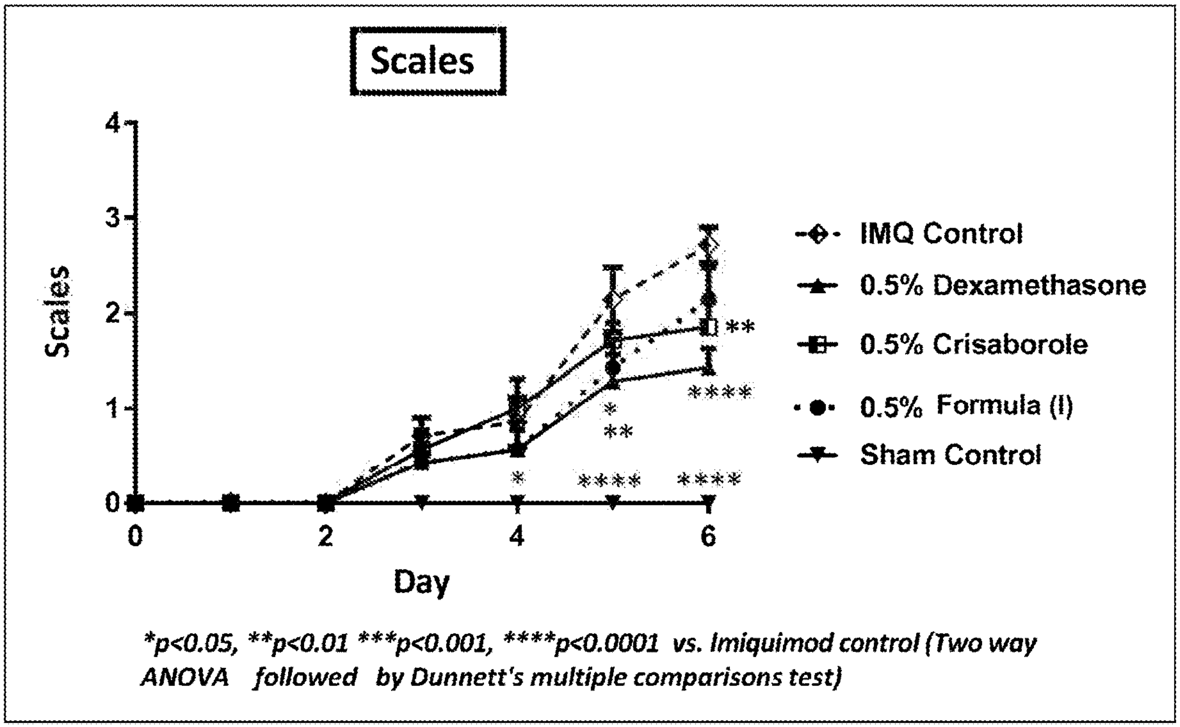
FIG. 32 shows scales by group in Example 2.
Figure 33:
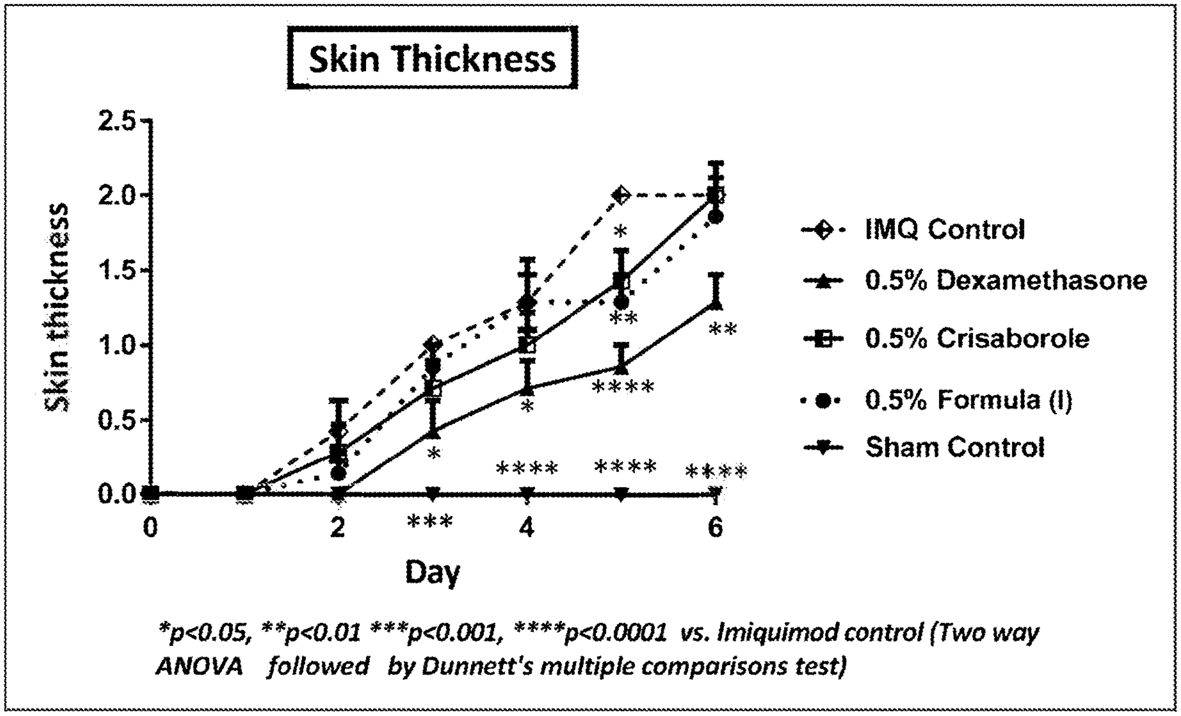
FIG. 33 shows skin thickness by group in Example 2.
Figure 34:
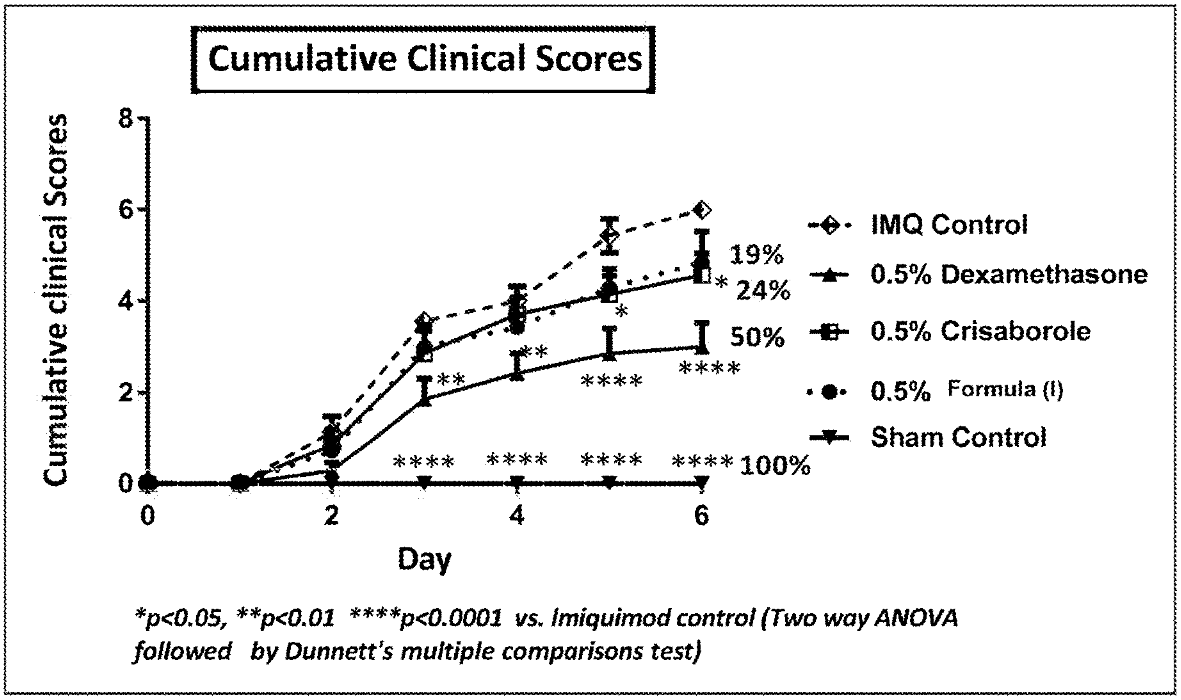
FIG. 34 shows cumulative clinical scores by group in Example 2.

On day 6, at termination, the back-skin thickness of each animal is measured. Significant increase in back skin thickness is observed after imiquimod application in the IMQ control animals when compared to sham control. Dexamethasone treated animals show significant reduction in back skin thickness ($p<0.0001$). Animals treated with Crisaborole and the compound of Formula (I) do not show significant reduction in the back-skin thickness. See FIG. 30.

Figure 41:
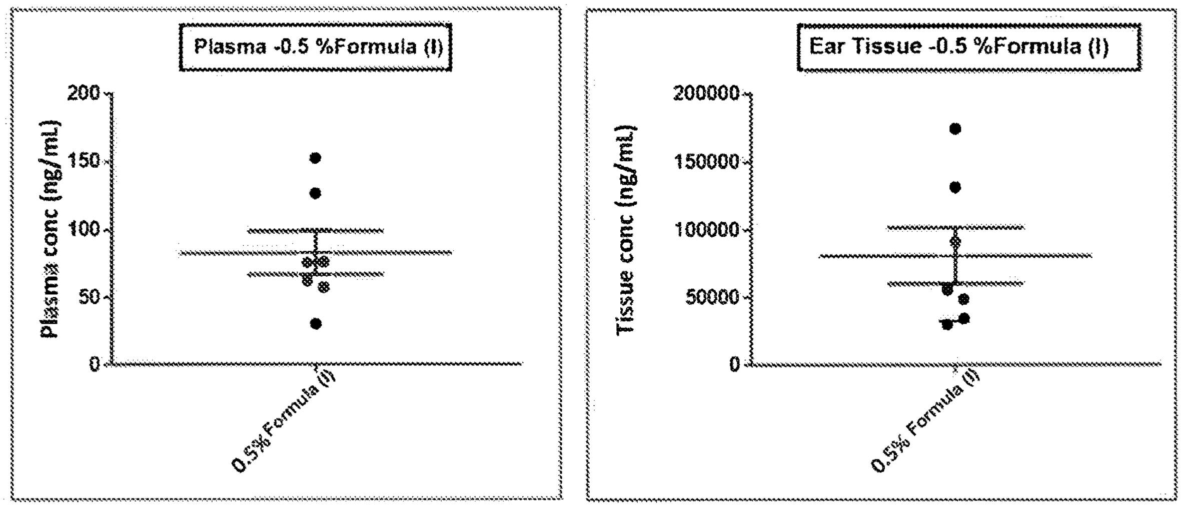
FIG. 41 shows plasma and ear tissue concentrations of the compound of Formula (I) in Example 2.

On day 6, post 2h treatment, plasma and ear skin concentration of animals treated with the compound of Formula (I) are estimated. Significant concentrations of test compound the compound of Formula (I) are observed in plasma and ear skin. The concentration in the ear skin is close to 976-fold more than the plasma levels. See FIG. 41.

Figure 37:
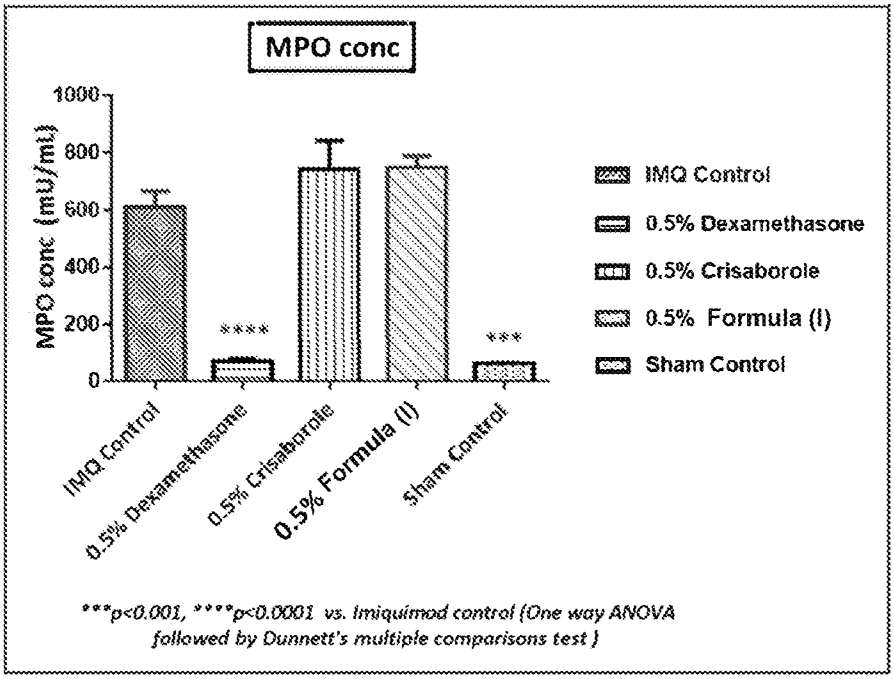
FIG. 37 shows the MPO by group in Example 2.

Myeloperoxidase (MPO) is an oxidative enzyme present in neutrophils. During inflammation, there is an infiltration of neutrophils and other immune mediators in the ear tissue. Increase in MPO activity is observed in ear tissue homogenates in the IMQ control group. Dexamethasone treated animals show significant inhibition of MPO activity ($p<0.001$). Animals treated with Crisaborole and the compound of Formula (I) do not show significant inhibition of MPO activity. See FIG. 37.

A histopathology (HP) score is given for each graded feature considering the percent involvement for each grade. The grading criteria for skin and ear are shown below.

| Histological grading criteria for IMQ induced psoriasis-Skin | | |
|---|---|---|
| Feature graded | Grade | Description |
| Acanthosis | 0 | None |
| | 1 | Increase in epidermal layer (5-5) |
| | 2 | Increase in epidermal layer (6-8) |
| | 3 | Increase in epidermal layer (9-10) |
| | 4 | Increase in epidermal layer (>10) |
| Hyperkeratosis | 0 | None |
| | 1 | Minimal |
| | 2 | Mild |
| | 3 | Moderate |
| | 4 | Severe |
| Parakeratosis | 0 | None |
| | 1 | Minimal (1-2 layers of stratum comeum with retention of nucleus) |
| | 2 | Mild (3-4 layers of stratum corneum with retention of nucleus) |
| | 3 | Moderate (5-6 layers of stratum corneum with retention of nucleus) |
| | 4 | Severe (>6 layers of stratum corneum with retention of nucleus) |
| Infiltration, inflammatory cells | 0 | None |
| | 1 | Minimal |
| | 2 | Mild |
| | 3 | Moderate |
| | 4 | Severe |

Percent Involvement is Scored for Each Graded Feature as Follows:

| | |
|---|---|
| 1 | 1-25% |
| 2 | 26-50% |
| 3 | 51-75% |
| 4 | 75-100% |

| Histological grading criteria for IMQ induced psoriasis-Ear | | |
|---|---|---|
| Feature graded | Grade | Description |
| Acanthosis | 0 | None |
| | 1 | Increase in epidermal layer (1-2) |
| | 2 | Increase in epidermal layer (3-4) |
| | 3 | Increase in epidermal layer (5-6) |
| | 4 | Increase in epidermal layer (>6) |
| Hyperkeratosis | 0 | None |
| | 1 | Minimal |
| | 2 | Mild |
| | 3 | Moderate |
| | 4 | Severe |
| Parakeratosis | 0 | None |
| | 1 | Minimal (1-2 layers of stratum corneum with retention of nucleus) |
| | 2 | Mild (3-4 layers of stratum corneum with retention of nucleus) |
| | 3 | Moderate (5-6 layers of stratum corneum with retention of nucleus) |
| | 4 | Severe (>6 layers of stratum comeum with retention of nucleus) |
| Infiltration, inflammatory cells | 0 | None |
| | 1 | Minimal |
| | 2 | Mild |
| | 3 | Moderate |
| | 4 | Severe |

Percent Involvement is Scored for Each Graded Feature as Follows:

| | |
|---|---|
| 1 | 1-25% |
| 2 | 26-50% |

-continued

| | |
|---|---|
| 3 | 51-75% |
| 4 | 76-100% |

Figure 42:
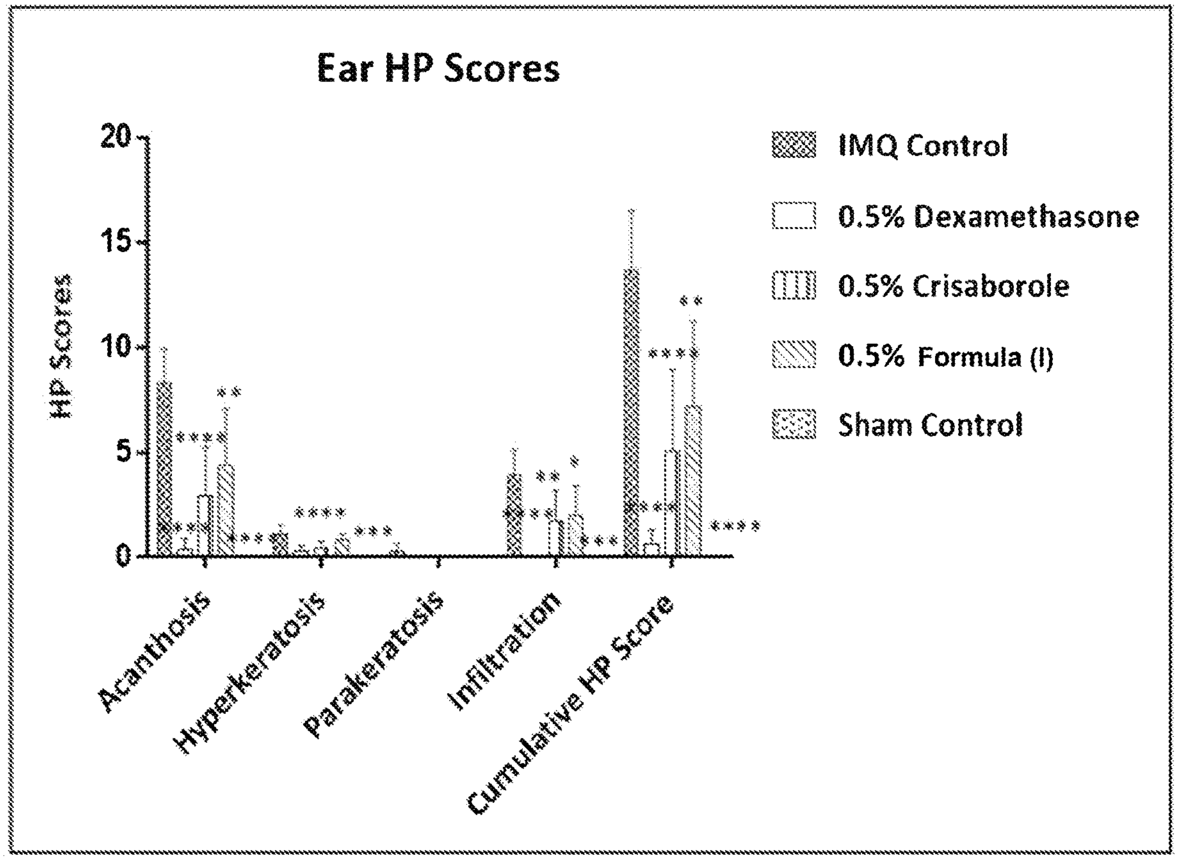
FIG. 42 shows ear histopathology scores in Example 2.
Figure 43:
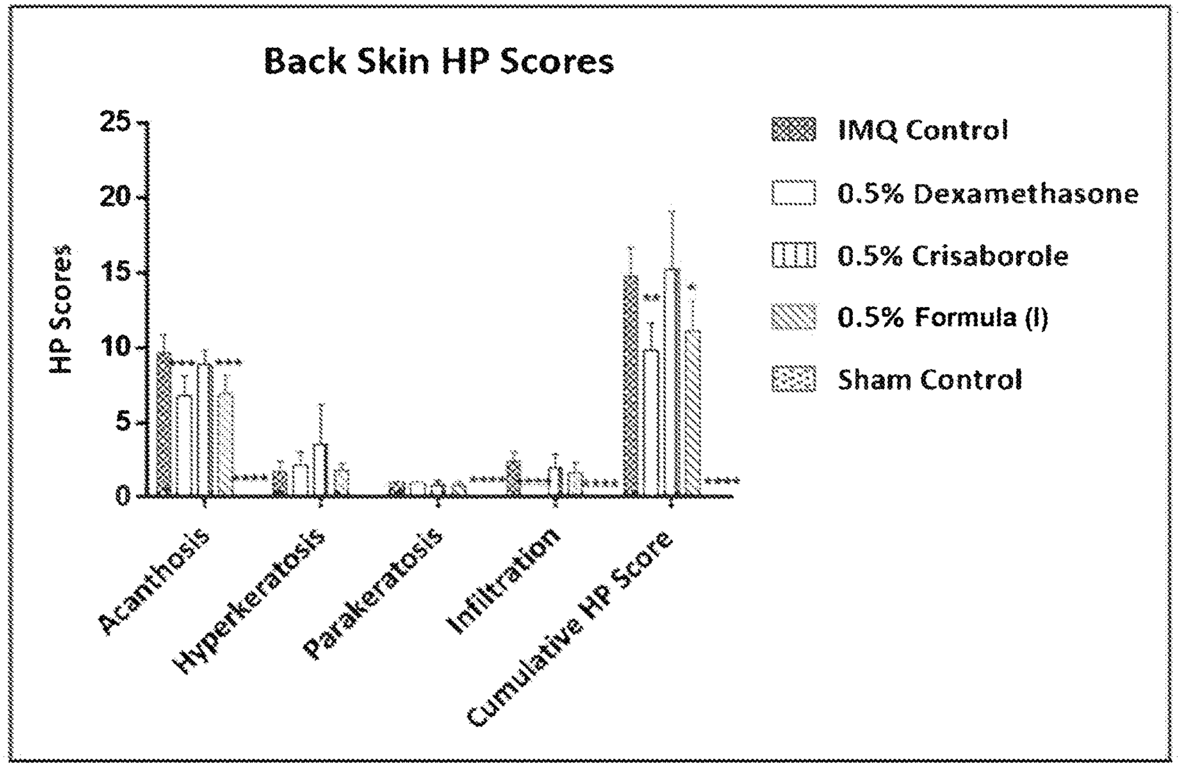
FIG. 43 shows back skin histopathology scores in Example 2.

Back and ear skin sections from IMQ control group show acanthosis, hyperkeratosis, parakeratosis and inflammatory cell infiltration in the dermis and epidermis. Treatment with dexamethasone results in significant reduction in the extent of acanthosis, infiltration and in the overall cumulative HP scores of ear and back skin. Animals treated with Crisaborole (0.5%) show significant reduction in the overall cumulative HP scores of ear skin. Animals treated with the compound of Formula (I)(0.5%) show significant reduction in extent of acanthosis, cellular infiltration in ear and in the overall cumulative HP scores of ear skin. Treatment also shows reduction in the extent of acanthosis of the back skin. A significant reduction in the cumulative HP score of back skin is observed. Overall, animals treated with the compound of Formula (I)(0.5%) show significant reduction in ear thickness and show significant reduction in ear and back skin histopathology scores. See FIGS. 42 and 43.

Figure 38:
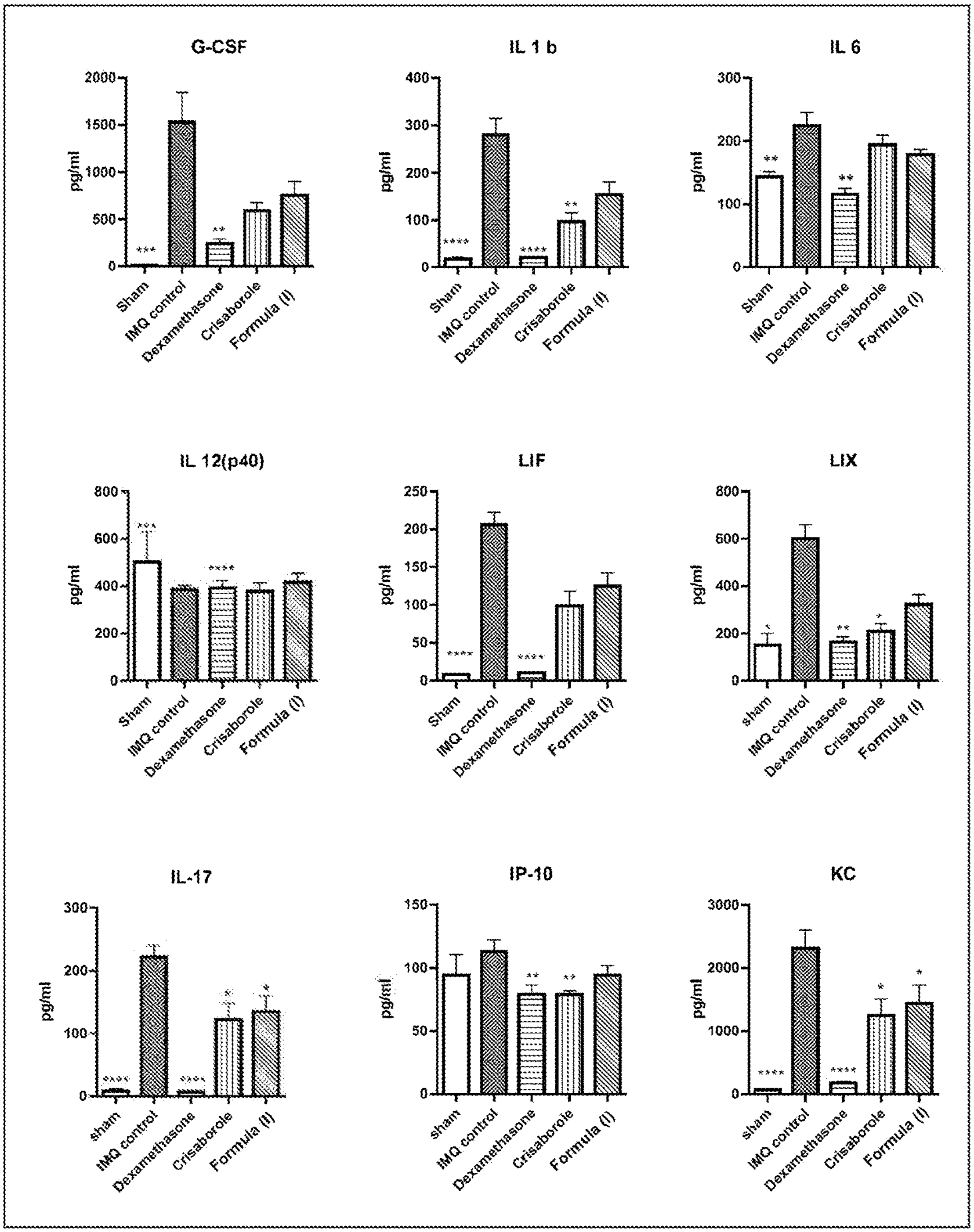
FIG. 38 shows cytokine levels in ear homogenate in Example 2.
Figure 39:
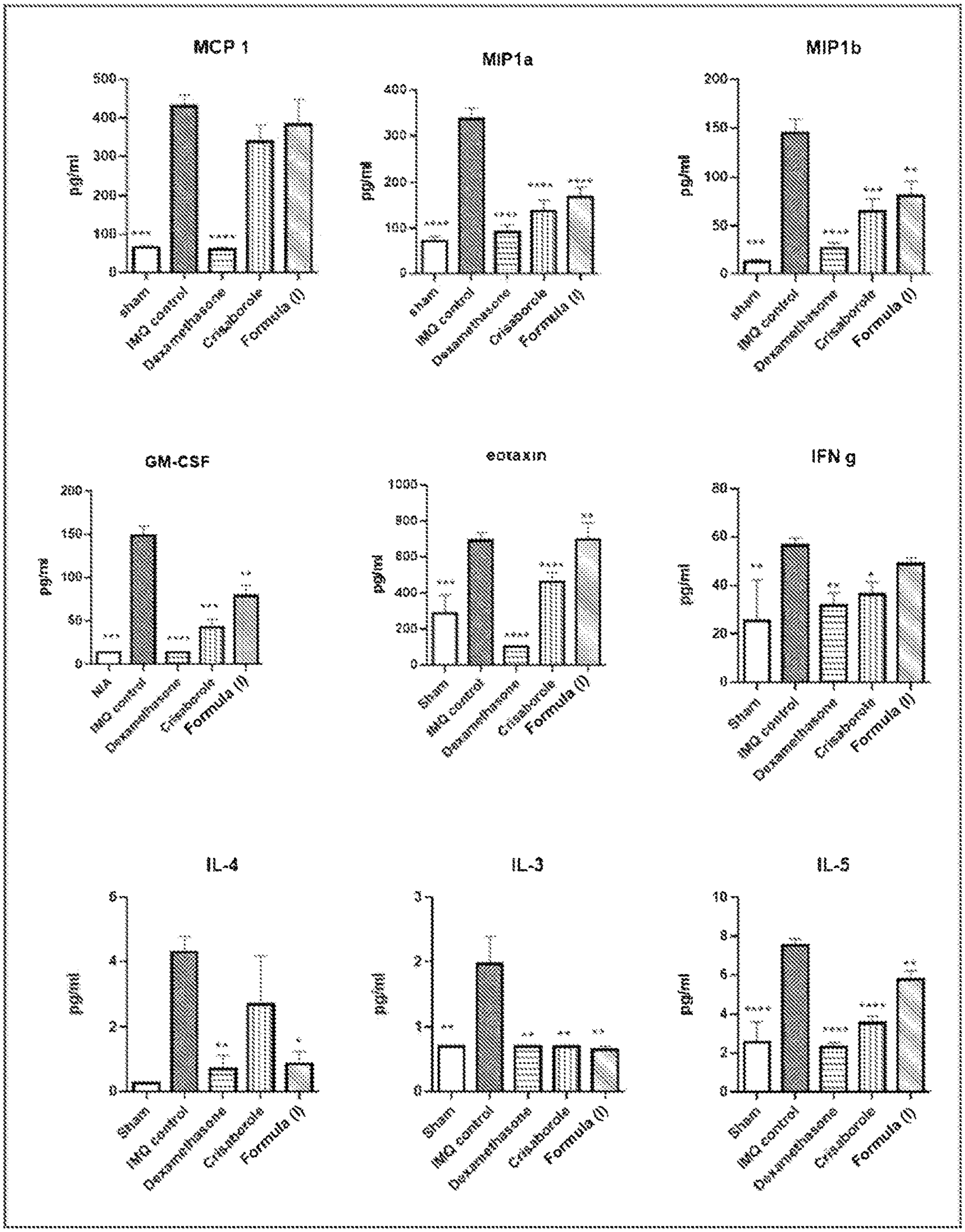
FIG. 39 shows cytokine levels in ear homogenate in Example 2.
Figure 40:
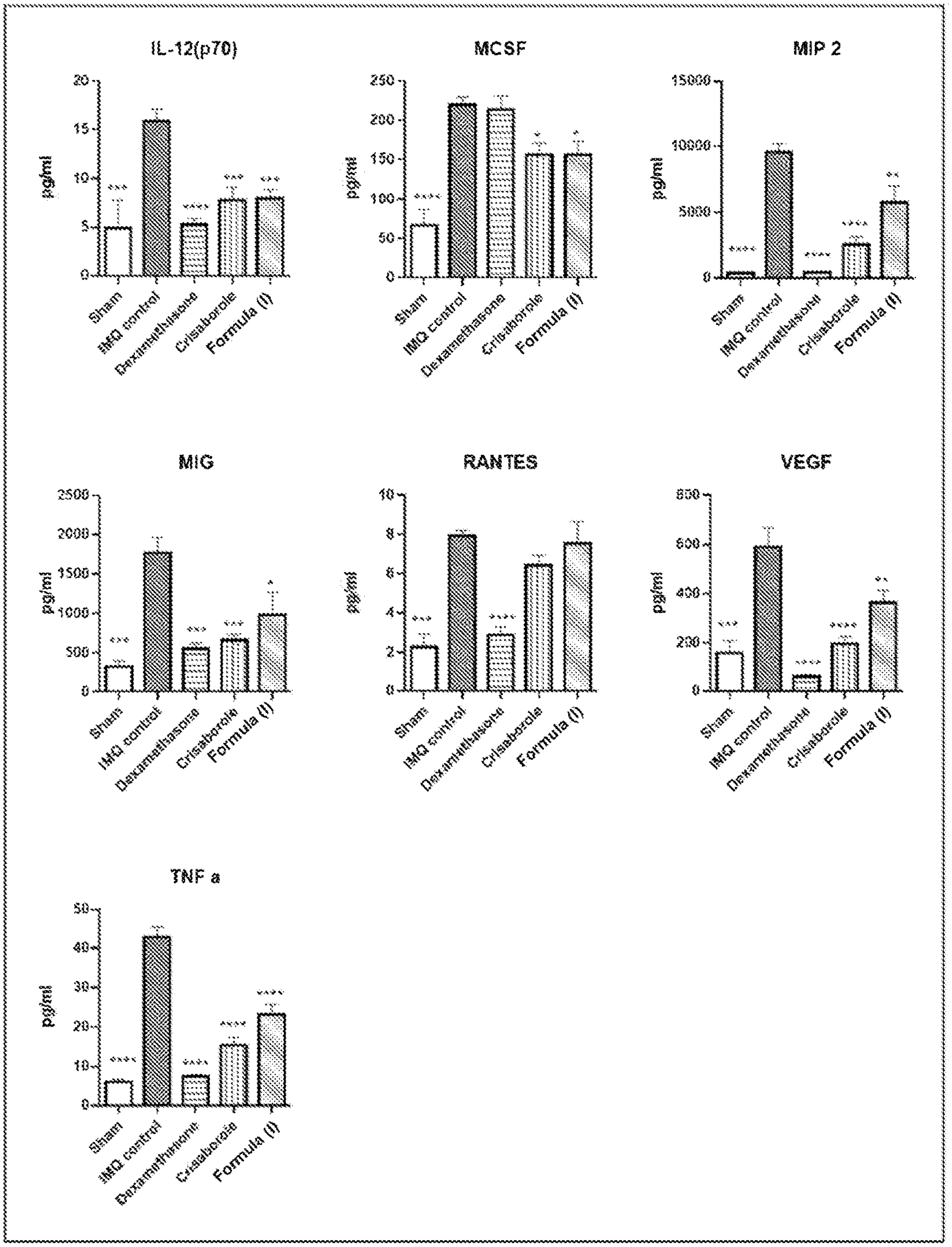
FIG. 40 shows cytokine levels in ear homogenate in Example 2.

Significant increase in the cytokine levels are observed in ear tissue homogenates after IMQ application in the IMQ control animals when compared to normal control animals. A significant increase in various pro-inflammatory cytokines are observed in IMQ control animals when compared to sham control animals. Topical treatment of dexamethasone to animals shows significant reduction in most of the cytokines elevated due to IMQ application in the ear when compared to IMQ control animals. Topical treatment of Crisaborole and the compound of Formula (I) shows significant reduction in few of the proinflammatory cytokines. See FIGS. 38-40.

Example 3

The activity of the compound of Formula (I) in phosphodiesterase IV subtypes is evaluated.

Methods employed in this study are adapted from the scientific literature to maximize reliability and reproducibility.

Reference standards are run as an integral part of each assay to ensure the validity of the results obtained. Reference Compounds:

Phosphodiesterase PDE10A2 Papaverine
Phosphodiesterase PDE11A4 Dipyridamole
Phosphodiesterase PDE1A MMPX
Phosphodiesterase PDE2A EHNA
Phosphodiesterase PDE3A Cilostamide
Phosphodiesterase PDE4A1A Rolipram
Phosphodiesterase PDE4B1 Rolipram
Phosphodiesterase PDE5A Zaprinast
Phosphodiesterase PDE6 Zaprinast
Phosphodiesterase PDE7A IBMX
Phosphodiesterase PDE7B IBMX
Phosphodiesterase PDE8A1 Dipyridamole
Phosphodiesterase PDE9A2 Zaprinast PDE4 assays are performed using methods adapted from the literature. See Richter W, et al. (2001) Identification of inhibitor binding sites of the cAMP-specific phosphodiesterase 4. Cell Signal. 13(4): 287-297; Wang H, et al. (2005) Multiple elements jointly determine inhibitor selectivity of cyclic nucleotide phosphodiesterases 4 and 7. J Biol Chem. 280(35): 30949-30955.

Phosphodiesterase PDE4A1A; Phosphodiesterase PDE4B1; Phosphodiesterase PDE10A2; Phosphodiesterase PDE11A4; Phosphodiesterase PDE2A; Phosphodiesterase PDE3A; Phosphodiesterase PDE7A; Phosphodiesterase PDE7B; and Phosphodiesterase PDE8A1:

Source: Human recombinant insect Sf9 cells
Substrate: 0.10 μM FAM-cAMP
Vehicle: 1.00% DMSO
Significance Crit.: ≥50% of max stimulation or inhibition
Incubation Buffer: 10 mM Tris-HCl, pH 7.2, 10 mM MgCl2, 0.05% NaN3, 0.1% phosphate-free BSA
Quantitation Method: Quantitation of Fluorescein-AMP-IMAP
Pre-Incub. Time/Temp: 15 minutes @25° C.
Incubation Time/Temp: 30 minutes @25° C.

Phosphodiesterase PDE1A; Phosphodiesterase PDE5A; and Phosphodiesterase PDE9A2:

Source: Human recombinant insect Sf9 cells
Substrate: 0.10 μM FAM-cAMP
Vehicle: 1.00% DMSO
Significance Crit.: ≥50% of max stimulation or inhibition
Incubation Buffer: 10 mM Tris-HCl, pH 7.2, 10 mM MgCl2, 0.05% NaN3, 0.1% phosphate-free BSA
Quantitation Method: Quantitation of Fluorescein-GMP-IMAP
Pre-Incub. Time/Temp: 15 minutes @25° C.
Incubation Time/Temp: 30 minutes @25° C.

Phosphodiesterase PDE6:

Source: Bovine retinal rod outer segments
Substrate: 100 μM [$^3$H]cGMP+cGMP
Vehicle: 1.00% DMSO
Significance Crit.: ≥50% of max stimulation or inhibition
Incubation Buffer: 50 mM Tris-HCl, pH 7.5, 5 mM MgCl2
Quantitation Method: Quantitation of [$^3$H]Guanosine
Pre-Incub. Time/Temp: 15 minutes @25° C.
Incubation Time/Temp: 20 minutes @25° C.

IC50 values are determined by a non-linear, least squares regression analysis using MathIQ™ (ID Business Solutions Ltd., UK). Where inhibition constants (Ki) are presented, the Ki values are calculated using the equation of Cheng and Prusoff (Cheng, Y., Prusoff, W. H., Biochem. Pharmacol. 22:3099-3108, 1973) using the observed IC50 of the tested compound, the concentration of radioligand employed in the assay, and the historical values for the KD of the ligand. Where presented, the Hill coefficient (nH), defining the slope of the competitive binding curve, is calculated using MathIQ™. Hill coefficients significantly different than 1.0, may suggest that the binding displacement does not follow the laws of mass action with a single binding site. Where IC50, Ki, and/or nH data are presented without Standard Error of the Mean (SEM), data are insufficient to be quantitative, and the values presented (Ki, IC50, nH) are interpreted with caution.

| Assay | Species | N | Conc. | % Inh. | Reference |
|---|---|---|---|---|---|
| Phosphodiesterase PDEIA | hum | 2 | 10 μM | −8 | Sonnenburg WK, Seger D, Kwak KS, Huang J, Charbonneau H and Beavo JA. (1995) Identification of inhibitory and calmodulin-binding domains of the PDE1A1 and PDE1A2 calmodulin-stimulated cyclic nucleotide phosphodiesterases. J Biol Chem. 270(52): 30989-31000. |
| Phosphodiesterase PDE2A | hum | 2 | 10 μM | 9 | Martinez SE, Wu AY, Glavas NA, Tang XB, Turley S, Hol WG and Beavo JA. (2002) The two GAF domains in phosphodiesterase 2A have distinct roles in dimerization and in cGMP binding. Proc Natl Acad Sci U S A. 99(20): 13260-13265. Seybold J, Thomas D, Witzenrath M, Boral S, Hocke AC, Burger A, Hatzelmann A, Tenor H, Schudt C, Krull M, Schutte H, Hippenstiel S and Suttorp N. (2005) Tumor necrosis factor-alpha-dependent expression of phosphodiesterase 2: role in endothelial hyperpermeability. Blood. 105(9): 3569-3576. |
| Phosphodiesterase PDE3A | hum | 2 | 10 μM | 6 | Hambleton R, Krall J, Tikishvili E, Honeggar M, Ahmad F, Manganiello VC and Movsesian MA. (2005) Isoforms of cyclic nucleotide phosphodiesterase PDE3 and their contribution to cAMP hydrolytic activity in subcellular fractions of human myocardium. J Biol Chem. 280(47): 39168-39174. Hung SH, Zhang W, Pixley RA, Jameson BA, Huang YC, Colman RF and Colman RW. (2006) New insights from the structure-function analysis of the catalytic region of human platelet phosphodiesterase |

-continued

| Assay | Species | N | Conc. | % Inh. | Reference |
|---|---|---|---|---|---|
| | | | | | 3A: a role for the unique 44-amino acid insert. J Biol Chem. 281(39): 29236-29244. |
| Phosphodiesterase PDE4A1A | hum | 2 | 10 µM | 99 | Richter W, Unciuleac L, Hermsdorf, T, Kronbach T and Dettmer D. (2001) Identification of inhibitor binding sites of the cAMP-specific phosphodiesterase 4. Cell Signal. 13(4): 287-297. Wang H, Liu Y, Chen Y, Robinson H and Ke H. (2005) Multiple elements jointly determine inhibitor selectivity of cyclic nucleotide phosphodiesterases 4 and 7. J Biol Chem. 280(35): 30949-30955. |
| Phosphodiesterase PDE4B1 | hum | 2 | 10 µM | 96 | Richter W, Unciuleac L, Hermsdorf T, Kronbach T and Dettmer D. (2001) Identification of inhibitor binding sites of the cAMP-specific phosphodiesterase 4. Cell Signal. 13(4): 287-297. Wang H, Liu Y, Chen Y, Robinson H and Ke H. (2005) Multiple elements jointly determine inhibitor selectivity of cyclic nucleotide phosphodiesterases 4 and 7. J Biol Chem. 280(35): 30949-30955. |
| Phosphodiesterase PDE5A | hum | 2 | 10 µM | 27 | Bruder S, Schultz A and Schultz JE. (2006) Characterization of the tandem GAF domain of human phosphodiesterase 5 using a cyanobacterial adenylyl cyclase as a reporter enzyme. J Biol Chem. 281(29): 19969-19976. Filippi S, Morelli A, Sandner P, Fibbi B, Mancina R, Marini M, Gacci M, Vignozzi L, Vannelli GB, Carini M, Forti G and Maggi M. (2007) Characterization and functional role of androgen-dependent PDE5 activity in the bladder. Endocrinology. 148(3): 1019-1029. |
| Phosphodiesterase PDE6 | bov | 2 | 10 µM | 8 | Baehr W, Devlin MJ and Applebury ML (1979) Isolation and characterization of cGMP phosphodiesterase from bovine rod outer segments. J Biol Chem. 254 (22): 11669-11677. Gillespie PG and Beavo JA (1989) Inhibition and stimulation of photoreceptor phosphodiesterases by dipyridamole and M&B 22, 948. Mol Pharm. 36: 773-781. |
| Phosphodiesterase PDE7A | hum | 2 | 10 µM | 7 | Bender AT and Beavo JA. (2006) Cyclic nucleotide phosphodiesterases: molecular regulation to clinical use. Pharmacol Rev. 58(3): 488-520. Wang H, Liu Y, Chen Y, Robinson H and Ke H. (2005) Multiple elements jointly determine inhibitor selectivity of cyclic nucleotide phosphodiesterases 4 and 7. J Biol Chem. 280(35): 30949-30955. |
| Phosphodiesterase PDE7B | hum | 2 | 10 µM | −1 | Sasaki T, Kotera J, Yuasa K and Omori K. (2000) Identification of human PDE7B, a cAMP-specific phosphodiesterase. Biochem Biophys Res Commun. 271(3): 575-583. Wang H, Liu Y, Chen Y, Robinson H and Ke H. (2005) |

-continued

| Assay | Species | N | Conc. | % Inh. | Reference |
|---|---|---|---|---|---|
| | | | | | Multiple elements jointly determine inhibitor selectivity of cyclic nucleotide phosphodiesterases 4 and 7. J Biol Chem. 280(35): 30949-30955. |
| Phosphodiesterase PDE8A1 | hum | 2 | 10 μM | 0 | Gamanuma M, Yuasa K, Sasaki T, Sakurai N, Kotera J and Omori K. (2003) Comparison of enzymatic characterization and gene organization of cyclic nucleotide phosphodiesterase 8 family in humans. Cell Signal. 15(6): 565-574. |
| Phosphodiesterase PDE9A2 | hum | 2 | 10 μM | −2 | Soderling SH, Bayµga SJ and Beavo JA. (1998) Identification and characterization of a novel family of cyclic nucleotide phosphodiesterases. J Biol Chem. 273(25): 15553-15558. |
| Phosphodiesterase PDE10A2 | hum | 2 | 10 μM | 11 | Gross-Langenhoff M, Hofbauer K, Weber J, Schultz A and Schultz JE. (2006) CAMP is a ligand for the tandem GAF domain of human phosphodiesterase 10 and cGMP for the tandem GAF domain of phosphodiesterase 11. J Biol Chem. 281(5): 2841-2846. |
| Phosphodiesterase PDE11A4 | hum | 2 | 10 μM | 14 | Yuasa K, Kotera J, Fujishige K, Michibata H, Sasaki T and Omori K. (2000) Isolation and characterization of two novel phosphodiesterase PDE11A variants showing unique structure and tissuespecific expression. J Biol Chem. 275(40): 31469-31479. |

Example 4

The activity of the compound of Formula (I) in phosphodiesterase IV subtypes is evaluated.

Methods employed in this study are adapted from the scientific literature to maximize reliability and reproducibility.

Reference standards are run as an integral part of each assay to ensure the validity of the results obtained. Rolipram is used for the PDE4 assays.

PDE4 assays are performed using methods adapted from the literature. See Richter W, et al. (2001) Identification of inhibitor binding sites of the cAMP-specific phosphodiesterase 4. Cell Signal. 13(4): 287-297; Wang H, et al. (2005) Multiple elements jointly determine inhibitor selectivity of cyclic nucleotide phosphodiesterases 4 and 7. J Biol Chem. 280(35): 30949-30955.

Phosphodiesterase PDE4A1A:
Source: Human recombinant insect Sf9 cells
Substrate: 0.10 μM FAM-cAMP
Vehicle: 1.00% DMSO
Significance Crit.: ≥50% of max stimulation or inhibition
Incubation Buffer: 10 mM Tris-HCl, pH 7.2, 10 mM MgCl2, 0.05% NaN3, 0.1% phosphate-free BSA
Quantitation Method: Quantitation of Fluorescein-AMP-IMAP
Pre-Incub. Time/Temp: 15 minutes @25° C.
Incubation Time/Temp: 30 minutes @25° C.

Phosphodiesterase PDE4B1:
Source: Human recombinant insect Sf9 cells
Substrate: 0.10 μM FAM-cAMP
Vehicle: 1.00% DMSO
Significance Crit.: ≥50% of max stimulation or inhibition
Incubation Buffer: 10 mM Tris-HCl, pH 7.2, 10 mM MgCl2, 0.05% NaN3, 0.1% phosphate-free BSA
Quantitation Method: Quantitation of Fluorescein-AMP-IMAP
Pre-Incub. Time/Temp: 15 minutes @25° C.
Incubation Time/Temp: 30 minutes @25° C.

$IC_{50}$ values are determined by a non-linear, least squares regression analysis using MathIQ™ (ID Business Solutions Ltd., UK). Where inhibition constants (Ki) are presented, the Ki values are calculated using the equation of Cheng and Prusoff (Cheng, Y., Prusoff, W.H., Biochem. Pharmacol. 22:3099-3108, 1973) using the observed $IC_{50}$ of the tested compound, the concentration of radioligand employed in the assay, and the historical values for the KD of the ligand. Where presented, the Hill coefficient (nH), defining the slope of the competitive binding curve, is calculated using MathIQ™. Hill coefficients significantly different than 1.0, may suggest that the binding displacement does not follow the laws of mass action with a single binding site. Where $IC_{50}$, Ki, and/or nH data are presented without Standard Error of the Mean (SEM), data are insufficient to be quantitative, and the values presented (Ki, $IC_{50}$, nH) are interpreted with caution.

| Assay | Species | N | Conc. | % Inh. | IC50 |
|---|---|---|---|---|---|
| Phosphodiesterase PDE4A1A | hum | 2 | 10 μM | 96 | 0.063 μM |
| | hum | 2 | 3 μM | 93 | |
| | hum | 2 | 1 μM | 87 | |
| | hum | 2 | 0.3 μM | 75 | |
| | hum | 2 | 0.1 μM | 58 | |
| | hum | 2 | 0.03 μM | 37 | |
| | hum | 2 | 10 nM | 23 | |

| Assay | Species | N | Conc. | % Inh. | IC50 |
|---|---|---|---|---|---|
| Phosphodiesterase PDE4B1 | hum | 2 | 10 μM | 94 | 0.094 μM |
| | hum | 2 | 3 μM | 91 | |
| | hum | 2 | 1 μM | 83 | |
| | hum | 2 | 0.3 μM | 70 | |
| | hum | 2 | 0.1 μM | 49 | |
| | hum | 2 | 0.03 μM | 34 | |
| | hum | 2 | 10 nM | 17 | |

Example 5

The activity of the compound of Formula (I) in PDE4D2 is evaluated.

Methods employed in this study are adapted from the scientific literature to maximize reliability and reproducibility.

Roliprami is used as a reference standard.

PDE4 assays are performed using methods adapted from the literature. See Houslay MD (2005) The long and short of vascular smooth muscle phosphodiesterase-4 as a putative therapeutic target. Mol Pharmacol. 68(3):563-567; MacKenzie S J and Houslay M D (2000) Action of rolipram on specific PDE4 cAMP phosphodiesterase isoforms and on the phosphorylation of cAMP-response element-binding protein (CREB) and p38 mitogen-activated protein (MAP) kinase in U937 monocytic cells. Biochem J. 347(Pt 2): 571-578.

Phosphodiesterase PDE4D2:

Source: Human recombinant insect Sf9 cells

Substrate: 0.10 μM FAM-cAMP

Vehicle: 1.00% DMSO

Significance Crit.: ≥50% of max stimulation or inhibition

Incubation Buffer: 10 mM Tris-HCl, pH 7.2, 10 mM MgCl2, 0.05% NaN3, 0.1% phosphate-free BSA Quantitation Method: Quantitation of Fluorescein-AMP-IMAP Pre-Incub. Time/Temp: 15 minutes @25° C.

Incubation Time/Temp: 15 minutes @25° C.

$IC_{50}$ values are determined by a non-linear, least squares regression analysis using MathIQ™ (ID Business Solutions Ltd., UK). Where inhibition constants (Ki) are presented, the Ki values are calculated using the equation of Cheng and Prusoff (Cheng, Y., Prusoff, W.H., Biochem. Pharmacol. 22:3099-3108, 1973) using the observed $IC_{50}$ of the tested compound, the concentration of radioligand employed in the assay, and the historical values for the KD of the ligand (obtained experimentally at Eurofins Panlabs, Inc.). Where presented, the Hill coefficient (nH), defining the slope of the competitive binding curve, is calculated using MathIQ™. Hill coefficients significantly different than 1.0, may suggest that the binding displacement does not follow the laws of mass action with a single binding site. Where $IC_{50}$, Ki, and/or nH data are presented without Standard Error of the Mean (SEM), data are insufficient to be quantitative, and the values presented (Ki, $IC_{50}$, nH) are interpreted with caution.

| Assay | Species | N | Conc. | % Inh. | IC50 |
|---|---|---|---|---|---|
| Phosphodiesterase PDE4D2 | hum | 2 | 10 μM | 99 | 6.19 nM |
| | hum | 2 | 3 μM | 97 | |
| | hum | 2 | 1 μM | 96 | |
| | hum | 2 | 0.3 μM | 91 | |
| | hum | 2 | 0.1 μM | 83 | |
| | hum | 2 | 0.03 μM | 70 | |
| | hum | 2 | 10 μM | 56 | |

Example 6

In preclinical studies, the compound of Formula (I) does not induce mutations or biologically relevant clastogenic effects in vitro or in vivo. Ocular instillation studies show that the compound of Formula (I) is well tolerated.

The compound of Formula (I) 0.034% ophthalmic solution has the composition:

| Ingredient | % w/v |
|---|---|
| Formula I | 0.034 |
| Polyoxyl 40 stearate | 5.00 |
| PEG-400 | 1.00 |
| Propylene Glycol | 1.00 |
| Sodium Chloride | 0.05 |
| Sodium CMC (Cekol 150) | 0.30 |
| Sodium thiosulfate pentahydrate | 0.20 |
| Disodium EDTA dihydrate | 0.10 |
| Sodium dihydrogen phosphate monohydrate | 0.0262 |
| Disodium phosphate anhydrous | 0.115 |
| Water for injection | QS to 100 mL |

The compound of Formula (I) 0.034% ophthalmic solution may be prepared using conventional techniques. For example, a solution of the compound of Formula I in PEG-400 and propylene glycol is prepared by adding Formula I to a mixture of PEG-400 and propylene glycol with stirring. The resulting solution is mixed with a solution of polyoxyl 40 stearate and a portion of the water used in the composition. The resulting solution is mixed with a solution of water, sodium dihydrogen phosphate monohydrate, disodium phosphate anhydrous, sodium CMC, sodium chloride, sodium thiosulfate pentahydrate, and disodium EDTA dihydrate to give a final solution which sterilized by filtration (0.2 μm PES filter). The filtered solution is filled into vials under aseptic conditions and sealed. The composition is packaged in a 5-mL, 20 mm, USP Type I, clear glass vial (silica coated) with a 20 mm gray stoppers and 20 mm Flip-off Seals.

The clinical model of allergic conjunctivitis used for the study is a conjunctival allergen challenge. See, for example, Abelson M B, Chambers W, Smith L M. Conjunctival allergen challenge. Arch Ophthalmol 1990, 108:84; Abelson M B and Loeffler O. Conjunctival allergen challenge: models in the investigation of ocular allergy. Curr Allergy Asthma Reports. 2003; 3:363-368.

Diagnosis: Allergic Conjunctivitis

Test Product: the compound of Formula (I) 0.034%.

Each qualifying subject undergoes a bilateral conjunctival allergen challenge titration using an allergen if they have a positive reaction to on their skin test. Subjects who elicit a positive reaction post—conjunctival allergen challenge undergo the confirmation conjunctival allergen challenge using the same allergen.

Randomization is used to avoid bias in the assignment of subjects to investigational product, to increase the likelihood that known and unknown subject attributes (e.g. demographics and baseline characteristics) are evenly balanced across treatment groups, and to enhance the validity of statistical comparisons across treatment groups. Finally, blinded treatment is used to reduce potential of bias during data collection and evaluation of clinical endpoints.

Treatment begins after subjects are randomized. Subjects receive an in-office dose of the treatment they are randomized to receive. Approximately 14-18 hours post-instillation of study medication, subjects undergo conjunctival allergen challenge to assess the 16-hour duration of action.

In a subsequent office visit, subjects receive an in-office dose of the same study medication. Approximately 8 hours post-instillation of study medication, subjects undergo conjunctival allergen challenge to assess the 8-hour duration of action.

In a subsequent office visit, subjects receive an in-office dose of the same study medication approximately 15 minutes prior to conjunctival allergen challenge to assess the 15-minute duration of action.

Efficacy Measures:

This clinical study evaluates the efficacy of the compound of Formula (I) 0.034% compared to vehicle for the treatment of the signs and symptoms of allergic conjunctivitis.

Ocular itching is evaluated by the subject at up to 10 minutes post-conjunctival allergen challenge.

Ocular itching is evaluated using a numerical scale ranging from no itch at one extreme to severe itch at the other extreme.

Conjunctival redness is evaluated by the investigator at up to 25 minutes post—conjunctival allergen challenge.

Conjunctival redness is evaluated using a numerical scale ranging from no redness at one extreme to severe redness at the other extreme.

Additional efficacy measures include, for example, ciliary redness, episcleral redness, chemosis, eyelid swelling, tearing, rhinorrhea, nasal pruritus, ear or palate pruritus, and nasal congestion are evaluated using a numerical scale ranging from no sign/symptom at one extreme to severe sign/symptom at the other extreme. Eyelid swelling is evaluated using a numerical scale ranging from no swelling at one extreme to severe swelling at the other extreme.

What is claimed:

1. A method for treatment of a patient with a phosphodiesterase IV (PDEIV)-mediated disease or condition that is psoriasis, atopic dermatitis, contact dermatitis, seborrheic dermatitis, stasis dermatitis, morphea, Behçet's Syndrome, lupus, alopecia, vitiligo, acne, lichen planus, uveitis, Prurigo nodularis, or discoid lupus erythematosus, comprising administering to said patient an amount of a compound of Formula (I):

(I)

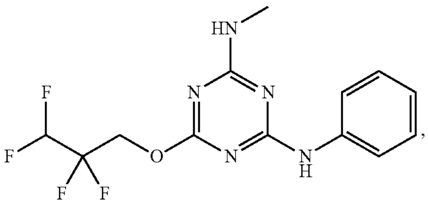

, or a pharmaceutically acceptable salt thereof, effective to treat said disease or condition.

2. The method of claim 1, wherein the PDEIV-mediated disease or condition is psoriasis.

3. The method of claim 2, wherein the PDEIV-mediated disease or condition is plaque psoriasis.

4. The method of claim 1, wherein the PDEIV-mediated disease or condition is atopic dermatitis.

5. The method of claim 1, wherein the PDEIV-mediated disease or condition is contact dermatitis.

6. The method of claim 1, wherein the patient is a human.

7. The method of claim 1, wherein the compound of Formula (I), or a pharmaceutically acceptable salt thereof, is administered as a pharmaceutical composition comprising said compound of Formula (I), or a pharmaceutically acceptable salt thereof, and a pharmaceutically acceptable excipient.

8. The method of claim 1, wherein the compound of Formula (I), or a pharmaceutically acceptable salt thereof, is administered topically, orally, perorally, as a suppository, intravenously, parenterally, intraperitoneally, intramuscularly, intralesionally, intrathecally, intranasally, or subcutaneously.

9. The method of claim 1, wherein the compound of Formula (I), or a pharmaceutically acceptable salt thereof, is administered topically.

10. The method of claim 1, wherein the compound of Formula (I), or a pharmaceutically acceptable salt thereof, is administered orally.

11. The method of claim 1, wherein the PDEIV-mediated disease or condition is seborrheic dermatitis.

12. The method of claim 1, wherein the PDEIV-mediated disease or condition is stasis dermatitis.

13. The method of claim 1, wherein the PDEIV-mediated disease or condition is morphea.

14. The method of claim 1, wherein the PDEIV-mediated disease or condition is Behçet's Syndrome.

15. The method of claim 1, wherein the PDEIV-mediated disease or condition is lupus.

16. The method of claim 1, wherein the PDEIV-mediated disease or condition is alopecia.

17. The method of claim 16, wherein the PDEIV-mediated disease or condition is frontal fibrosing alopecia.

18. The method of claim 1, wherein the PDEIV-mediated disease or condition is vitiligo.

19. The method of claim 1, wherein the PDEIV-mediated disease or condition is acne.

20. The method of claim 1, wherein the PDEIV-mediated disease or condition is lichen planus.

21. The method of claim 1, wherein the PDEIV-mediated disease or condition is uveitis.

22. The method of claim 1, wherein the PDEIV-mediated disease or condition is Prurigo nodularis.

23. The method of claim 1, wherein the PDEIV-mediated disease or condition is discoid lupus erythematosus.

* * * * *